United States Patent
Kim et al.

(10) Patent No.: US 9,969,698 B2
(45) Date of Patent: May 15, 2018

(54) QUINOXALINYL-PIPERAZINAMIDE METHODS OF USE

(71) Applicant: REXAHN PHARMACEUTICALS, INC., Rockville, MD (US)

(72) Inventors: Deog Joong Kim, Rockville, MD (US); Young Bok Lee, Clarksburg, MD (US); Reza Mazhari, Towson, MD (US); Daniel Edward Emrich, Frederick, MD (US)

(73) Assignee: REXAHN PHARMACEUTICALS, INC., Rockville, MD (US)

( * ) Notice: Subject to any disclaimer, the term of this patent is extended or adjusted under 35 U.S.C. 154(b) by 0 days. days.

(21) Appl. No.: 15/255,910

(22) Filed: Sep. 2, 2016

(65) Prior Publication Data
US 2017/0066726 A1    Mar. 9, 2017

Related U.S. Application Data

(60) Provisional application No. 62/214,678, filed on Sep. 4, 2015, provisional application No. 62/289,820, filed on Feb. 1, 2016.

(51) Int. Cl.
| | |
|---|---|
| *A61K 31/498* | (2006.01) |
| *A61K 45/06* | (2006.01) |
| *C07D 241/44* | (2006.01) |
| *A61K 9/14* | (2006.01) |
| *A61K 47/02* | (2006.01) |
| *A61K 9/08* | (2006.01) |

(52) U.S. Cl.
CPC .............. *C07D 241/44* (2013.01); *A61K 9/14* (2013.01); *A61K 31/498* (2013.01); *A61K 45/06* (2013.01); *A61K 9/08* (2013.01); *A61K 47/02* (2013.01)

(58) Field of Classification Search
CPC ... A61K 31/498; A61K 45/06; A61K 2300/00
See application file for complete search history.

(56) References Cited

U.S. PATENT DOCUMENTS

| | | | |
|---|---|---|---|
| 4,369,174 A | 1/1983 | Nagai et al. | |
| 4,842,866 A | 6/1989 | Horder et al. | |
| 5,217,720 A | 6/1993 | Sekigawa et al. | |
| 6,569,457 B2 | 5/2003 | Ullah et al. | |
| 6,638,534 B1 | 10/2003 | Ishibashi et al. | |
| 8,314,100 B2 | 11/2012 | Gong et al. | |
| 8,598,173 B2 | 12/2013 | Gong et al. | |
| 2013/0053390 A1 | 2/2013 | Gong et al. | |
| 2014/0341917 A1 | 11/2014 | Nastri et al. | |
| 2015/0004234 A1 | 1/2015 | Lee et al. | |

FOREIGN PATENT DOCUMENTS

WO    WO 2006054830 A1 *    5/2006    ........... C07D 241/44

OTHER PUBLICATIONS

Moreno et al. British Journal of Cancer, 2015, vol. 112, pp. 1421-1427.*
Lee et al. Bioorganics & Medicinal Chemistry, 2010, vol. 18, pp. 7966-7994.*
Teo et al. British Journal of Clinical Pharmacology, Aug. 14, 2014, vol. 79, No. 2, pp. 241-253.*
Coombs et al., Proc. Natl. Acad. Sci. USA, 75:5291-5295 (1978).
Shin et al., Cancer Res., 67:7572-7578 (2007).
Yang et al., Cell, 127:139-155 (2006).
Lomenick et al., Proc. Natl. Acad. Sci. USA, 106:21984-21989 (2009).
Simon et al., J. Natl. Cancer inst., 89(15):1138-47 (1997).
Eckhardt et al., "A Phase 1 study of RX-5902 (Supinoxin) an Oral Agent Targeting Phosphorylated p68 to Treat Subjects with Advanced Solid Tumors," Presented at the 2015 American Society of Clinial Oncology (ASCO) Annual Meeting, Chicago, Illinois, (Jun. 29, 2015).
Gluck et al., "Single Agent Supinoxin Targeting Phosphorylated p-68 Preliminary Phase 1 Data," Presented at the 2015 The European Cancer Congress (ECC 2015) Annual Meeting, Vienna, Austria, (Sep. 25, 2015).
Lee et al., "Synthesis, anticancer activity and pharmacokinetic analysis of 1-[(substituted 2-alkoxyquinoxalin-3-y)aminocarbonyl]-4-(hetero)arylpiperazine derivatives," Bioorganic & Medicinal Chemistry, vol. 20, No. 3, pp. 1303-1309 (2012).
Kost et al., "A Novel Anti-Cancer Agent, 1-(3,5-Dimethoxyphenyl)-4-[(6-Fluoro-2-Methoxyquinoxalin-3-yl)Aminocarbonyl] Piperazine (RX-5902), Interferes with [beta]-Catenin Function Through Y593 Phospho-p68 RNA Helicase," Journal of Cellular Biochemistry, vol. 116, No. 8, pp. 1595-1601 (2015).
International Search Report in International Application No. PCT/US2016/050172, dated Apr. 13, 2017.
Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, Jul. 2005.

* cited by examiner

*Primary Examiner* — Samira Jean-Louis
(74) *Attorney, Agent, or Firm* — Venable LLP; Keith G. Haddaway; Annette K. Kwok

(57) ABSTRACT

The disclosed subject matter provides methods using and kits comprising a compound of formula (I)

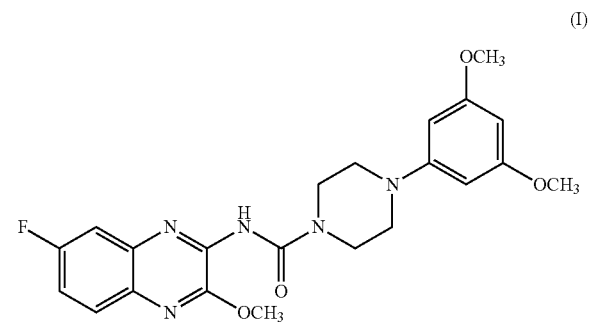

or a pharmaceutically acceptable salt thereof.

13 Claims, 35 Drawing Sheets

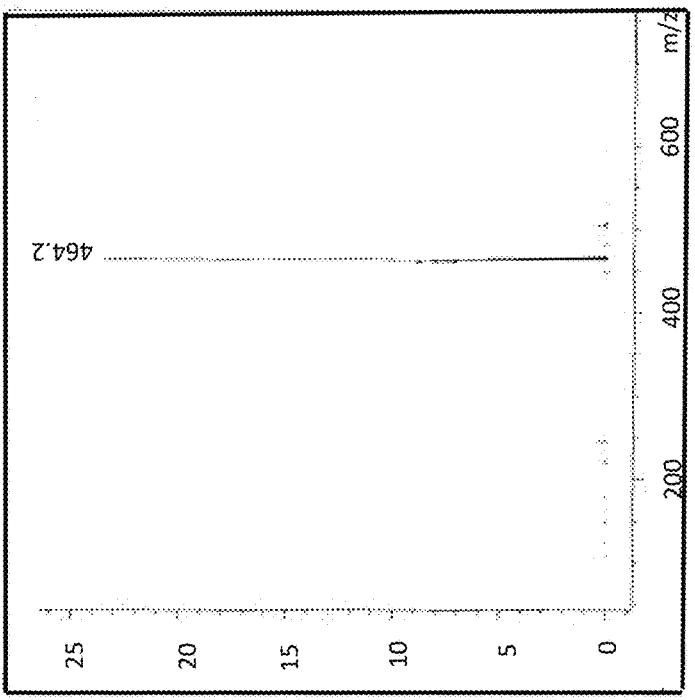
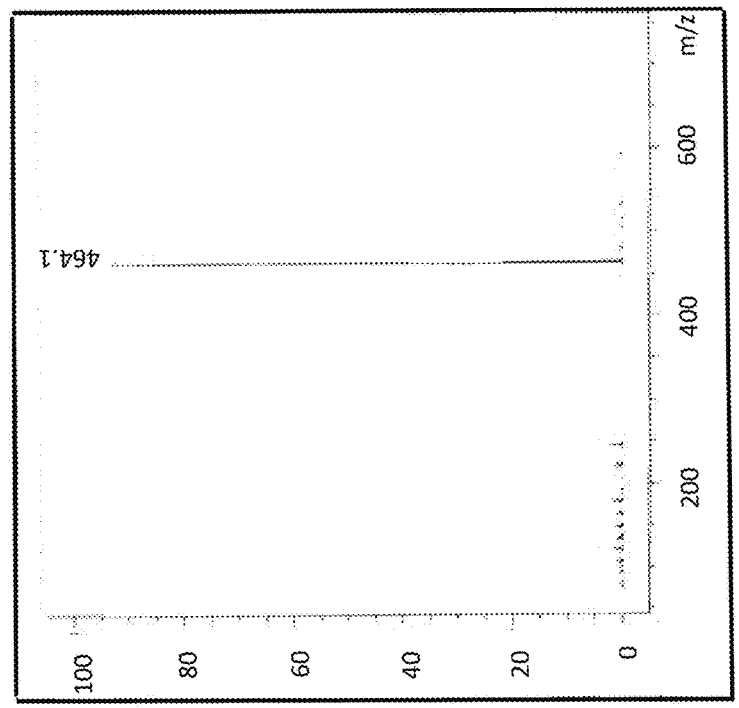
FIG. 32

QUINOXALINYL-PIPERAZINAMIDE METHODS OF USE

1. PRIORITY

This application claims priority to U.S. Provisional Application No. 62/214,678, filed Sep. 4, 2015; and U.S. Provisional Application No. 62/289,820 filed Feb. 1, 2016, the contents of which are hereby incorporated by reference in the entirety.

2. SUMMARY OF THE INVENTION

The following summary is presented for illustrative purposes and should not serve to limit the scope of the claimed subject matter.

U.S. Pat. No. 8,314,100 (issued Nov. 20, 2012), incorporated by reference herein in its entirety, discloses a compound of formula (I)

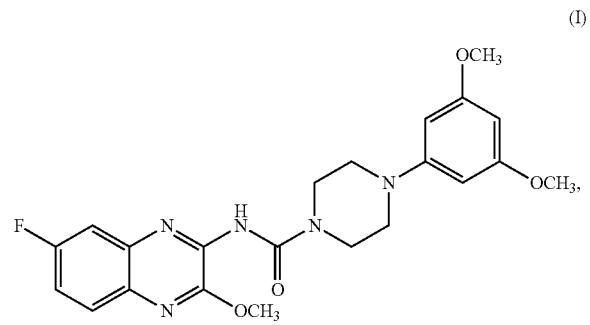 [SMILES: COc1cc(OC)cc(N2CCN(C(=O)Nc3nc4cc(F)ccc4nc3OC)CC2)c1]

(I)

also referred to elsewhere as RX-5902, 4-(3, 5-dimethoxyphenyl)-N-(7-fluoro-3-methoxyquinoxalin-2-yl)piperazine-1-carboxamide, 1-[(6-fluoro-2-methoxyquinoxalin-3-yl)aminocarbonyl]-4-(3,5-dimethoxyphenyl)piperazine, and 1-(3,5-dimethoxyphenyl)-4-[(6-fluoro-2-methoxyquinoxalin-3-yl)aminocarbonyl]piperazine.

Other aspects of RX-5902 are described in U.S. Pat. No. 8,598,173 (issued Dec. 3, 2013) and U.S. Publish Application No. 2015/0004234 (published Jan. 1, 2015), both of which are incorporated by reference herein in its entirety.

One aspect of the disclosure provides a method of treating a tumor by administering to a subject in need thereof a solid, oral dosage form comprising a compound of formula (I) or pharmaceutically acceptable salt thereof, wherein the solid, oral dosage form provides an $AUC_{0-t}$ (0-24 hours) of about 800-15,000 hr·ng/mL after a single administration. In an embodiment, the solid, oral dosage form provides an $AUC_{0-t}$ (0-24 hours) of about 2,500-9,300 hr·ng/mL after a single administration. In an embodiment, the solid, oral dosage form provides an $AUC_{0-t}$ (0-24 hours) of about 2,500-9,500 hr·ng/mL after a single administration. In an embodiment, the solid, oral dosage form may provide a $C_{max}$ of about 200-1,200 ng/mL after a single administration.

Another aspect of the disclosure provides a method of treating a tumor by administering to a subject in need thereof a solid, oral dosage form comprising a compound of formula (I) or pharmaceutically acceptable salt thereof, at a dosage of about 100-1,200 mg/day 1-7 days per week, up to about 2,800 mg/week. In an embodiment, the dosage may be about 150-400 mg/day 3-7 days per week. In another embodiment, the dosage may be about 150-400 mg/day 5-7 days per week. In an embodiment, the solid, oral dosage form may be a tablet or capsule.

In any embodiment, the subject may be a human. In any embodiment, the tumor may be selected from skin, colorectal, ovarian, lung, breast, pancreatic, stomach and renal cancer. In embodiments the tumor may be triple negative (TN) breast cancer. In embodiments, the tumor may be platinum-resistant or refractory ovarian cancer.

Another aspect of the disclosure, the method of treating a tumor, further includes administering radiation or an anti-tumor agent to the subject. In another aspect of the disclosure, the method of treating a tumor, further includes administering to the subject an anti-tumor agent selected from antimetabolites, DNA-fragmenting agents, DNA-crosslinking agents, intercalating agents, protein synthesis inhibitors, topoisomerase I poisons, topoisomerase II poisons, microtubule-directed agents, kinase inhibitors, polyphenols, hormones, hormone antagonists, death receptor agonists, immune checkpoint inhibitors, anti-programmed cell death 1 (PD-1) receptor antibodies and anti-programmed cell death ligand 1 (PD-L1) antibodies. In an embodiment, the method comprises administering to the subject a PD-L1 antibody or PD-1 antibody.

Another aspect of the disclosure provides a method of treating a tumor in a subject in need thereof, including the steps of: (a) determining whether the subject is undergoing treatment with a CYP3A4 or CYP3A5 inhibitor or inducer; and (b) if the subject is not undergoing treatment with a CYP3A4 or CYP3A5 inhibitor or inducer, then administering to the subject an effective amount of a compound of formula (I) or pharmaceutically acceptable salt thereof. In embodiments, the method further includes the steps of (c) monitoring the subject for an adverse event.

Another aspect of the disclosure provides a method of inhibiting β-catenin dependent ATPase activity of Y593 phosphorylated p68, by administering to a subject in need thereof an effective amount of a compound of formula (I) or pharmaceutically acceptable salt thereof.

Another aspect of the disclosure provides a kit for testing potential efficacy of a compound of formula (I) or pharmaceutically acceptable salt thereof in treating a tumor, that includes an assay that determines whether the tumor expresses Y593 phosphorylated p68.

Another aspect of the disclosure provides a method of treating a tumor in a subject in need thereof, by the steps of (a) collecting a sample of the tumor from the subject; (b) determining whether the tumor expresses Y593 phosphorylated p68; and (c) if the tumor expresses the Y593 phosphorylated p68, then administering to the subject an effective amount of a compound of formula (I) or pharmaceutically acceptable salt thereof.

Another aspect of the disclosure provides a method for preparing 4-(3, 5-dimethoxyphenyl)-N-(7-fluoro-3-methoxyquinoxalin-2-yl)piperazine-1-carboxamide (RX-5902) on a commercial scale, for example, in one or more fixed reactors. In embodiments, the preparation of RX-5902 on a commercial scale can include the steps of reacting 3-amino-6-fluoro-2-methoxyquinoxaline with ethyl chloroformate in an organic solvent in the presence of a base to form a mixture; distilling the mixture while adding ethyl acetate to form a suspension; filtering the suspension to isolate ethyl-N-(6-fluoro-2-methoxyquinoxaline-3-yl) carbonate; and reacting the ethyl-N-(6-fluoro-2-methoxyquinoxaline-3-yl) carbonate with 1-(3,5-dimethoxyphenyl) piperazine hydrochloride in a second organic solvent in the presence of a second base. In embodiments, the commercial scale production can further include the steps of reacting 3-amino-2-chloro-6-fluoroquinoxaline with sodium methoxide in an organic solvent in the presence of a base to form a mixture; adding water to the mixture to form a solution; cooling the solution to a temperature of about 15-20° C. to form a suspension; and filtering the suspension to isolate 3-amino-6-fluoro-2-methoxyquinoxaline. In embodiments, one or more of the organic solvents can be dichloromethane. In embodiments, the base can be pyridine. In embodiments, one or more of the distilling steps can be conducted under atmospheric pressure. In embodiments, filtering can be by vacuum filtration. In embodiments, the second organic solvent can be tetrahydrofuran. In embodiments, the second base can be 1,8-diazabicycloundec-7-ene (DBU).

New nanoformulations providing improved oral bioavailability of RX-5902 have also been discovered. The present invention is directed to new uses and methods of using the compound of formula (I) and nanoformulations thereof. The present invention also provides an improved process to reduce impurities and significantly reduce the cost of manufacturing by, among other things, removing solvent using distillation and filtering of the final product. The present invention also provides new nanoformulations for improved bioavailability of RX-5902. In addition, the present invention provides dosage and exposure levels for using the compound of formula (I) and its nanoformulations in a subject. Another aspect of the disclosure provides a method for preparing a mixture of particles of a compound of formula (1), or pharmaceutically acceptable salt thereof; under conditions sufficient to provide a suspension. In an embodiment, the suspension may be made by a milling process. In an embodiment the milling process may be high-energy agitator milling or roller milling. In an embodiment, the milling process is high-energy agitator milling. In an embodiment, the suspension may have a D50 particle size of about 200 nm or less.

Embodiments of the method can include spray drying the suspension to form a powder.

An aspect of the disclosure provides a product prepared by the method of making RX-5902 by a process described herein.

3. BRIEF DESCRIPTION OF FIGURES

FIG. 32 shows RX-5902 and the RRT 0.975 Impurity having the exact $[M+Na]^+$ mass of 464.

4. DETAILED DESCRIPTION

Figure 1:
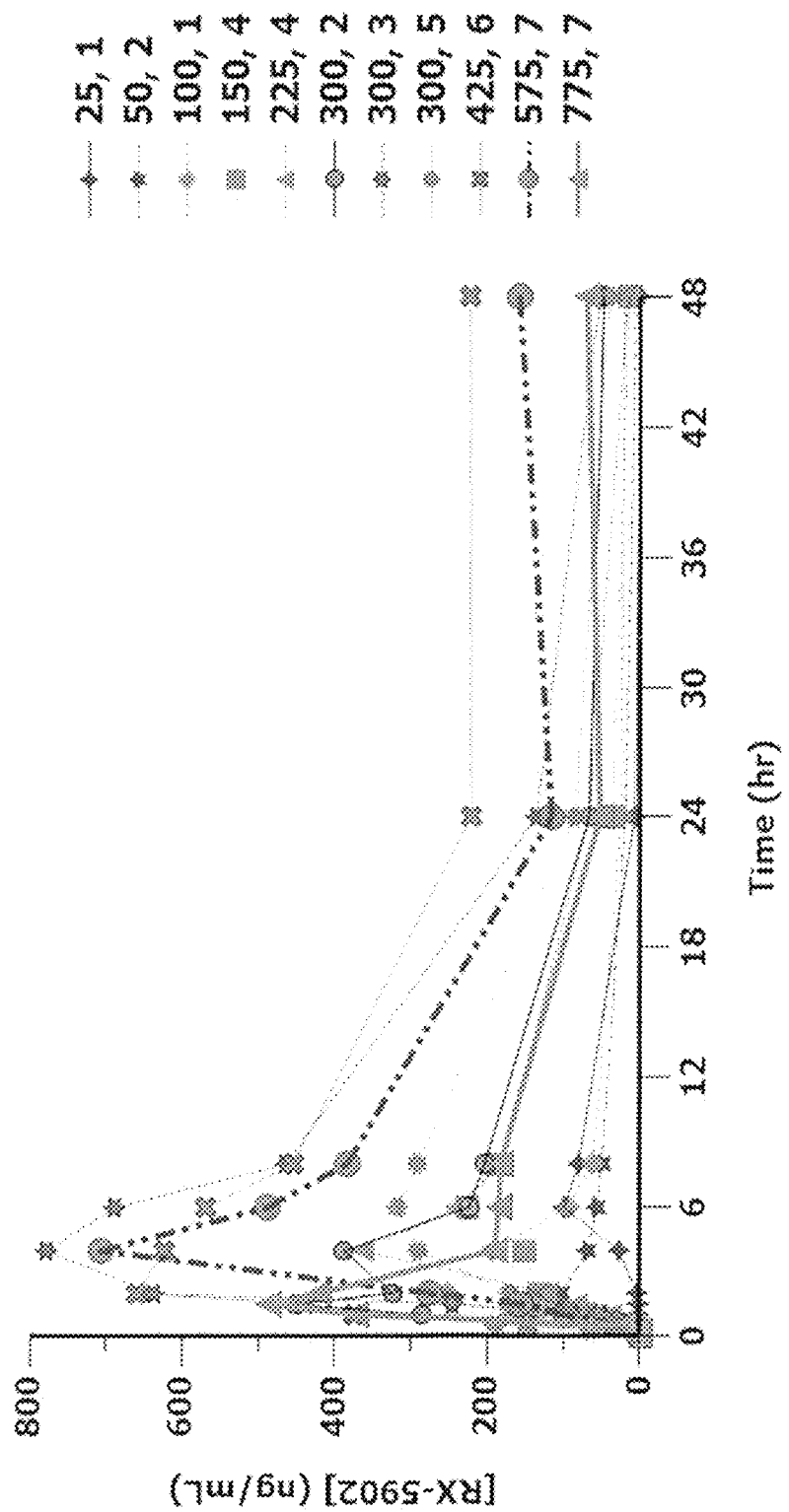
FIG. 1 is a graph showing the plasma concentration of RX-5902 in subjects with advanced or metastatic solid tumors after a single oral administration of RX-5902 at various doses under fasted conditions.

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention.

4.1 Definitions

Unless indicated otherwise, the following terms as used herein have the meanings indicated below. These meanings are intended to supplement, rather than alter, the meanings of these terms as understood in the art.

"$C_{max}$" refers to the maximum observed plasma concentration.

"$T_{max}$" refers to the time at which $C_{max}$ is attained.

"$T_{1/2}$" refers to the time required for the plasma concentration of a drug to reach half of its original value. "Terminal $T_{1/2}$" refers to $T_{1/2}$ in the terminal phase.

"$AUC_{0-t}$" refers to the area under the plasma concentration versus time curve (AUC) from time zero to time t, wherein "t" is the last sampling time point with measurable concentration. For example, $AUC_{0-24}$ or $AUC_{0-t}$ (0-24 hours) refers to the AUC from time zero to 24 hours, while $AUC_{0-48}$ or $AUC_{0-t}$ (0-48 hours) refers to the AUC from time zero to 48 hours.

"Oral dosage form" refers to a pharmaceutical composition formulated for oral administration. The oral dosage form can be formulated to provide immediate, sustained, extended, delayed or controlled release. Examples of an oral dosage form include tablets, capsules, granulations and gel-caps.

"Effective amount" refers to an amount of a compound or pharmaceutical composition that, based on its parameters of efficacy and potential for toxicity and the knowledge of one skilled in the art, produces a desired effect, such as treating or preventing a condition. An effective amount can be administered in one or more doses.

"Contacting" refers to causing, either directly or indirectly, a compound and a cell to be in sufficient proximity as to produce a desired effect, such as inducing apoptosis or modulating protein kinase. The contacting may be performed in vitro or in vivo. For example, contacting a cell with a compound may involve delivering the compound directly into the cell using known techniques such as micro-injection, administering the compound to a subject carrying the cell, or incubating the cell in a medium that includes the compound.

"Treating" refers to attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a subject suffering from the condition, decreasing the dose of another medication required to treat the condition, enhancing the effect of another medication a subject is taking for the condition, and prolonging the survival of a subject having the condition.

"Preventing" refers to reducing the probability that a subject develops a condition which the subject does not have but is at risk of developing. "At risk" denotes that a subject has one or more risk factors, which are measurable parameters that correlate with the development of a condition and are known in the art. A subject having one or more of risk factors has a higher probability of developing the condition than a subject without such risk factors.

"Subject" refers to an animal, such as a mammal, including but not limited to, a human. Hence, the methods disclosed herein can be useful in human therapy and veterinary applications. In one embodiment, the subject is a mammal. In another embodiment, the subject is a human.

"Fasted" refers to a subject that has fasted from food for at least 8 hours prior to treatment.

"CYP3A4 or CYP3A5 inhibitor or inducer" refers to an agent that increases or decreases, respectively, plasma AUC values of substrates for the cytochrome P450 3A4 (CYP3A4) or P450 3A5 (CYP3A5) enzyme by at least about 30 percent. Examples of a CYP3A4 or CYP3A5 inhibitor or inducer include amprenavir, aprepitant, atazanavir, barbiturate, boceprevir, bosentan, carbamazepine, chloramphenicol, ciprofloxacin, clarithromycin, cobicistat, conivaptan, darunavir, diltiazem, efavirenz, elvitegravir, erythromycin, etravirine, fluconazole, fosamprenavir, grapefruit juice, imatinib, indinavir, itraconazole, ketoconazole, lopinavir, mibefradil, modafinil, nafcillin, nefazodone, nelfinavir, phenytoin, posaconazole, rifampin, ritonavir, saquinavir, St. John's Wort, telaprevir, telithromycin, tenofovir, tipranavir, verapamil and voriconazole.

"Adverse event" refers to any undesirable effect associated with the use of a compound or pharmaceutical composition. An adverse event may be assessed and graded according to the National Cancer Institute Common Terminology Criteria for Adverse Events (NCI-CTCAE) version 4.03. Examples of an adverse event include febrile neutropenia, anemia, thrombocytopenia, coagulation abnormality associated with clinical hemorrhage, diarrhea, fatigue, nausea and vomiting.

"Sensitizing" refers to increasing a cell's sensitivity to, or reducing a cell's resistance in responding to, an apoptotic signal.

"Modifying" a treatment or administration refers to reducing or increasing the dose of an active agent, ceasing to administer the active agent to a subject, or substituting the active agent with a different active agent.

"Inhibition" refers to a decrease in the expression level (such as of a gene) or activity (such as of an enzyme) in the presence of an agent (such as a compound of formula (I)), relative to the expression level or activity in the absence of that agent. The decrease can be, for example, 5% or more, 10% or more, 20% or more, 25% or more, 30% or more, 40% or more, 50% or more, 60% or more, 70% or more, 75% or more, 80% or more, 90% or more, or 95% or more. The expression level or activity can be measured as described herein or by techniques generally known in the art.

"Tumor cell" refers to a cell derived from a tumor.

"Tumor" refers to an abnormal growth of tissue or cells, whether benign or malignant. Examples include tumors found in prostate, lung, brain, breast, kidney, liver, lung, intestines, lymph, muscle, bone, bone marrow, uterus, ovary, vagina, vulva, pancreas, adrenal gland, central nervous system, peripheral nervous system, cervix, bladder, endometrium, throat, esophagus, larynx, thyroid, blood, penal, testicular, thymus, skin, spine, stomach, bile duct, small bowel, hepatobiliary tract, colorectal, colon, rectum, anus, endocrine, eye, and gall bladder.

"Cancer" refers to a malignant tumor. Cancer cells may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type.

"Anti-tumor agent" refers to any agent useful for treating or preventing tumor. Examples of an anti-tumor agent include the active agents described in Pharmaceutical Compositions, infra. In embodiments, the anti-tumor agent in addition to RX-5902 is selected from antimetabolites, DNA-fragmenting agents, DNA-crosslinking agents, intercalating agents, protein synthesis inhibitors, topoisomerase I poisons, topoisomerase II poisons, microtubule directed agents, kinase inhibitors, polyphenols, hormones, hormone antagonists, death receptor agonists, immune checkpoint inhibitors, anti-programmed cell death 1 (PD-1) receptor antibodies and anti-programmed cell death ligand 1 (PD-L1) antibodies. In other embodiments, the additional anti-tumor agent is a PD-1 receptor antibody. In other embodiments, the additional anti-tumor agent is pembrolizumab. In other embodiments, the additional anti-tumor agent is nivolumab. In other embodiments, the additional anti-tumor agent is duryalumab. In other embodiments, the additional anti-tumor agent is combination of nivolumab and pembrolizumab.

"Radiation" refers to any radiation useful for treating or preventing tumor. Examples of radiation include X-rays, gamma rays, and charged particles. The radiation may be delivered by any form of radiation therapy, such as external beam radiotherapy (EBRT, XBRT or teletherapy), brachytherapy (internal radiation therapy or sealed source therapy), intraoperative radiotherapy, or systemic radiation therapy.

"Y593 phosphorylated p68" or "Y593 phospho-p68" refers to the p68 RNA helicase (DDX5) phosphorylated at the tyrosine 593 residue.

"p68 RNA helicase," also known as "ATP-dependent RNA helicase DDX5" or "DEAD box protein 5," refers to an enzyme that in humans is encoded by the DDX5 gene.

"Commercial scale" refers to the preparation of a product in a quantity that would be suitable for its manufacture for sale and distribution to the public. Commercial scale is distinguished from laboratory or bench scale in which the quantity produced is suitable for research purposes. Commercial scale is also distinguished from laboratory or bench scale synthesis in using reagents and methods that minimize use or waste of hazardous substances to minimize disposal and clean-up costs. In certain embodiments, the commercial scale methods disclose herein yield a single batch quantity of at least about 0.5 kg, 1.0 kg or 1.5 kg.

"Reacting" refers to combining two or more reagents under appropriate conditions (e.g., temperature, pressure, pH, concentration) to produce a desired product. The desired product may not necessarily result directly from the combination of the two or more reagents; i.e., one or more intermediates may be produced which ultimately lead to the formation of the desired product.

"Distillation" or "distilling" refers to separating compounds based on their different volatilities, such as by vaporization or subsequent condensation.

"Filtration" or "filtering" refers to separating solids from a liquid, such as by vacuum, gravity or pressure. "Vacuum filtration" refers to a technique for extracting solids from a liquid mixture, in which vacuum suction is applied to draw the mixture through a filter, such as filter paper in a Buchner funnel.

"Atmospheric pressure" refers to open air pressure, as opposed to the pressure in a vacuum or enclosed chamber. Atmospheric pressure is typically about 760 Torr, but it can vary depending inter alia on the evaluation of the manufacturing facility.

"Vacuum filtration" refers to a technique for extracting solids from a liquid mixture, in which vacuum suction is applied to draw the mixture through a filter, such as filter paper in a Buchner funnel.

"Fixed reactor" refers to a reactor that is fixed in place and does not move.

"Particle size" refers to the particle dimension of an active pharmaceutical ingredient (API), such as the compound of formula (I) or pharmaceutically acceptable salt thereof, as determined by any particle size measuring technique known in the art. Non limiting examples of such technique include laser diffraction, dynamic light scattering and image analysis performed, for example, using an analyzer, such as one available from Malvern, Sympatec, Microtac or Horiba.

"D10" refers to the particle size at 10% in the cumulative distribution, meaning that 10% of the particles have a particle size of less than D10, and 90% of the particles have a particle size of more than D10. "D50" refers to the median particle size or the particle size at 50% in the cumulative distribution, meaning that 50% of the particles have a particle size of less than D50, and 50% of the particles have a particle size of more than D50. "D90" refers to the median particle size or the particle size at 90% in the cumulative distribution, meaning that 90% of the particles have a particle size of less than D90, and 10% of the particles have a particle size of more than D90. The cumulative distribution may be based on the volume, mas, number or surface area of the particles. Unless otherwise specified, the cumulative distribution is based on the volume of the particles.

"Lyophilizing" refers to using a freeze-drying process to remove substantially one or more solvents from a product by freezing the product and then reducing the surrounding pressure to allow the frozen solvent(s) in the product to sublimate directly from the solid phase to the gas phase.

"Spray drying" refers to a method of producing a dry powder from a liquid or slurry by rapidly drying with a hot gas.

"Such as" has the same meaning as "such as but not limited to." Similarly, "include" has the same meaning as "include but not limited to," while "including" has the same meaning as "including but not limited to."

The singular forms "a," "or," and "the" include plural referents unless the context dictates otherwise. Thus, for example, a reference to "a compound" may include one or more compound(s) and/or equivalent(s) thereof.

Any numerical range disclosed herein encompasses the upper and lower limits and each intervening value, unless otherwise specified.

Other than in the working examples, or where otherwise indicated, numerical values (such as numbers expressing quantities of ingredients, reaction conditions) as used in the specification and claims are modified by the term "about". Accordingly, unless indicated to the contrary, such numbers are approximations that may vary depending upon the desired properties sought to be obtained. At the very least, and not as an attempt to limit the application of the doctrine of equivalents to the scope of the claims, each numerical parameter should be construed in light of the number of significant digits and ordinary rounding techniques.

While the numerical parameters setting forth the scope of the disclosed subject matter are approximations, the numerical values set forth in the working examples are reported as precisely as possible. Any numerical value, however, inherently contains certain errors necessarily resulting from the standard deviation found in its respective testing measurements.

Unless defined otherwise, the meanings of technical and scientific terms as used herein are those commonly understood by one of ordinary skill in the art to which the disclosed subject matter belongs.

4.2 Methods of Treating or Preventing a Tumor

One aspect of the disclosure provides a method of treating or preventing a tumor, by administering to a subject in need thereof an effective amount of a compound of formula (I) or pharmaceutically acceptable salt thereof, after the subject has fasted from food for at least about 8 hours. In another embodiment, the subject continues to fast from food for at least about 3 hours after administration.

Another aspect of the disclosure provides a method of treating or preventing a tumor, by administering to a subject in need thereof a solid, oral dosage form including a compound of formula (I) or pharmaceutically acceptable salt thereof, wherein the solid, oral dosage form provides an $AUC_{0-t}$ (0-24 hours) of about 800-15,000 hr·ng/mL after a single administration.

Another aspect of the disclosure provides a method of treating or preventing a tumor, comprising administering to a subject in need thereof a solid, oral dosage form including a compound of formula (I) or pharmaceutically acceptable salt thereof, wherein the solid, oral dosage form provides an $AUC_{0-t}$ (0-168 hours; i.e., one week) of about 1,000-70,000 hr·ng/mL after one week, 1-7 days per week, of administration.

Another aspect of the disclosure provides a method of treating or preventing a tumor, by administering to a subject in need thereof a solid, oral dosage form including a compound of formula (I) or pharmaceutically acceptable salt thereof, at a dosage of about 100-1,200 mg/day 1-7 days per week. In embodiments, the compound of formula (I) or pharmaceutically acceptable salt thereof may be administered in an amount of up to about 3,000 mg/week. In embodiments, the compound of formula (I) or pharmaceutically acceptable salt thereof may be administered in an amount of up to about 2,800 mg/week. In one embodiment, the dosage is about 100-500 mg/day 3-7 days per week. In another embodiment, the dosage is about 100-500 mg/day 5-7 days per week. In another embodiment, the dosage is about 150-400 mg/day 3-7 days per week. In another embodiment, the dosage is about 150-400 mg/day 5-7 days a week Another aspect of the disclosure provides a method of treating or preventing a tumor in a subject in need thereof, by: (a) determining whether the subject is undergoing treatment with a CYP3A4 or CYP3A5 inhibitor or inducer; and (b) if the subject is not undergoing treatment with a CYP3A4 or CYP3A5 inhibitor or inducer, then administering to the subject an effective amount of a compound of formula (I) or pharmaceutically acceptable salt thereof. In one embodiment, the subject is undergoing treatment with a CYP3A4 or CYP3A5 inhibitor. In another embodiment, the subject is undergoing treatment with a CYP3A4 or CYP3A5 inducer.

Another aspect of the disclosure provides a method of treating or preventing a tumor in a subject in need thereof, by: (a) determining whether the subject is undergoing treatment with a CYP3A4 or CYP3A5 inhibitor or inducer; (b) if the subject is undergoing treatment with a CYP3A4 or CYP3A5 inhibitor or inducer, then administering to the subject an effective amount of a compound of formula (I) or pharmaceutically acceptable salt thereof; and (c) monitoring the subject for an adverse event. In another embodiment, the method further comprises modifying the treatment with CYP3A4 or CYP3A5 inhibitor or inducer or the administration of the compound of formula (I) or pharmaceutically acceptable salt thereof if an adverse event is detected. In one embodiment, the subject is undergoing treatment with a CYP3A4 or CYP3A5 inhibitor. In another embodiment, the subject is undergoing treatment with a CYP3A4 or CYP3A5 inducer.

Modifying treatment may include, for example, reducing or increasing the dose of the CYP3A4 or CYP3A5 inhibitor or inducer, or reducing or increasing the dose of RX-5902. In some embodiments, modifying includes one or more of the following: reducing the dose of the CYP3A4 or CYP3A5 inhibitor, increasing the dose of the CYP3A4 or CYP3A5 inducer, increasing the dose of RX-5902 if the subject is undergoing treatment with a CYP3A4 or CYP3A5 inhibitor, and decreasing the dosage of RX-5902 if the subject is undergoing treatment with a CYP3A4 or CYP3A5 inducer.

In one embodiment, the CYP3A4 or CYP3A5 inhibitor or inducer is a barbiturate, bosentan, carbamazepine, efavirenz, etravirine, modafinil, nafcillin, phenytoin, rifampin, St. John's Wort, glucocorticoid, nevirapine, oxcarbazepine, phenobarbital, pioglitazone, rifabutin, troglitazone and grapefruit juice. In another embodiment, the CYP3A4 or CYP3A5 inhibitor or inducer is grapefruit juice. In another embodiment, the CYP3A4 or CYP3A5 inhibitor or inducer is St. John's Wort.

Another aspect of the disclosure provides a method of treating a tumor in a subject in need thereof by the steps of:
(a) collecting a sample of the tumor from the subject;
(b) determining whether the tumor expresses Y593 phosphorylated p68; and
(c) if the tumor expresses the Y593 phosphorylated p68, then administering to the subject an effective amount of a compound of formula (I) or pharmaceutically acceptable salt thereof.

Additional embodiments of the methods disclosed herein are described below.

In one embodiment, the compound of formula (I) or pharmaceutically acceptable salt thereof is administered 5-7 days per week. In another embodiment, the compound of formula (I) or pharmaceutically acceptable salt thereof is administered 5-7 days per week for 4 consecutive weeks or for 3 consecutive weeks followed by 1 off-week during which the compound of formula (I) or pharmaceutically acceptable salt thereof is not administered. In another embodiment, the compound of formula (I) or pharmaceutically acceptable salt thereof is administered for up to 12 dosing cycles, wherein each dosing cycle consists of either 3 consecutive weeks of treatment followed by 1 off-week, or 4 consecutive weeks of treatment.

In another embodiment, the compound of formula (I) or pharmaceutically acceptable salt thereof is formulated as a solid, oral dosage form. In another embodiment, the solid, oral dosage form is a tablet. In another embodiment, the solid, oral dosage form is a capsule. In another embodiment, the oral, solid dosage form is a tablet or capsule comprising nanoparticles of the compound of formula (I) or pharmaceutically acceptable salt thereof.

In another embodiment, the solid, oral dosage form, compound of formula (I) or pharmaceutically acceptable salt thereof is administered after the subject has fasted from food for at least about 8 hours. In another embodiment, the subject fasts from food for at least about 3 hours after administration. In another embodiment, the solid, oral dosage form, compound of formula (I) or pharmaceutically acceptable salt thereof is administered with food.

In another embodiment, the solid, oral dosage form provides a $T_{max}$ of about 1-6 hours after a single administration. In another embodiment, the solid, oral dosage form provides a $T_{max}$ of about 2-6 hours after a single administration. In another embodiment, the solid, oral dosage form provides a $T_{max}$ of about 2 hours after a single administration. In another embodiment, the solid, oral dosage form provides a $T_{max}$ of about 3 hours after a single administration. In another embodiment, the solid, oral dosage form provides a $T_{max}$ of about 4 hours after a single administration. In another embodiment, the solid, oral dosage form provides a $T_{max}$ of about 5 hours after a single administration. In another embodiment, the solid, oral dosage form provides a $T_{max}$ of about 6 hours after a single administration.

In another embodiment, the solid, oral dosage form provides a $C_{max}$ of about 90-1,200 ng/mL after a single administration. In an embodiment, the solid, oral dosage form may provide a $C_{max}$ of about 200-1200 ng/mL after a single administration. In another embodiment, the solid, oral dosage form provides a $C_{max}$ of about 200-800 ng/mL after a single administration. In another embodiment, the solid, oral dosage form provides a $C_{max}$ of about 300-700 ng/mL after a single administration. In another embodiment, the solid, oral dosage form provides a $C_{max}$ of about 200-300 ng/mL after a single administration. In another embodiment, the solid, oral dosage form provides a $C_{max}$ of about 300-400 ng/mL after a single administration. In another embodiment, the solid, oral dosage form provides a $C_{max}$ of about 400-500 ng/mL after a single administration. In another embodiment, the solid, oral dosage form provides a $C_{max}$ of about 500-600 ng/mL after a single administration. In another embodiment, the solid, oral dosage form provides a $C_{max}$ of about 600-700 ng/mL after a single administration. In another embodiment, the solid, oral dosage form provides a $C_{max}$ of about 700-800 ng/mL after a single administration.

In another embodiment, the solid, oral dosage form provides an $AUC_{0-t}$ (0-24 hours) of about 800-15,000 h·ng/mL after a single administration. In another embodiment, the solid, oral dosage form provides an $AUC_{0-t}$ (0-24 hours) of about 2,000-15,000 hr·ng/mL after a single administration. In another embodiment, the solid, oral dosage form provides an $AUC_{0-t}$ (0-24 hours) of about 2,000-8,500 h·ng/mL after a single administration. In another embodiment, the solid, oral dosage form provides an $AUC_{0-t}$ (0-24 hours) of about 2,000-10,000 h·ng/mL after a single administration. In an embodiment, the solid, oral dosage form provides an $AUC_{0-t}$ (0-24 hours) of about 2,500-9,500 hr·ng/mL after a single administration. In an embodiment, the solid, oral dosage form provides an $AUC_{0-t}$ (0-24 hours) of about 2,500-9,300 hr·ng/mL after a single administration. In another embodiment, the solid, oral dosage form provides an $AUC_{0-t}$ (0-24 hours) of about 3,000-7,500 hr·ng/mL after a single administration. In another embodiment, the solid, oral dosage form provides an $AUC_{0-t}$ (0-24 hours) of about 3,500-7,000 hr·ng/mL after a single administration. In another embodiment, the solid, oral dosage form provides an $AUC_{0-t}$ (0-24 hours) of about 3,000-5,000 hr·ng/mL after a single administration. In another embodiment, the solid, oral dosage form provides an $AUC_{0-t}$ (0-24 hours) of about 4,000-6,500 h·ng/mL after a single administration. In another embodiment, the solid, oral dosage form provides an $AUC_{0-t}$ (0-24 hours) of about 4,500-6,000 h·ng/mL after a single administration. In another, embodiment, the solid, oral dosage form provides an $AUC_{0-t}$ (0-24 hours) of about 2,000-3,000 hr·ng/mL after a single administration. In another embodiment, the solid, oral dosage form provides an $AUC_{0-t}$ (0-24 hours) of about 3,000-4,000 hr·ng/mL after a single administration. In another embodiment, the solid, oral dosage form provides an $AUC_{0-t}$ (0-24 hours) of about 4,000-5,000 hr·ng/mL after a single administration. In another embodiment, the solid, oral dosage form provides an $AUC_{0-t}$ (0-24 hours) of about 5,000-6,000 hr·ng/mL after a single administration. In another embodiment, the solid, oral dosage form provides an $AUC_{0-t}$ (0-24 hours) of about 6,000-7,000 hr·ng/mL after a single administration. In another embodiment, the solid, oral dosage form provides an $AUC_{0-t}$ (0-24 hours) of about 7,000-8,000 hr·ng/mL after a single administration. In another embodiment, the solid, oral dosage form provides an $AUC_{0-t}$ (0-24 hours) of about 8,000-9,000 hr·ng/mL after a single administration. In another embodiment, the solid, oral dosage form provides an $AUC_{0-t}$ (0-24 hours) of about 9,000-10,000 h·ng/mL after a single administration. In another embodiment, the solid, oral dosage form provides an $AUC_{0-t}$ (0-24 hours) of about 10,000-11,000 h·ng/mL after a single administration. In another embodiment, the solid, oral dosage form provides an $AUC_{0-t}$ (0-24 hours) of about 11,000-12,000 h·ng/mL after a single administration. In another embodiment, the solid, oral dosage form provides an $AUC_{0-t}$ (0-24 hours) of about 12,000-13,000 h·ng/mL after a single administration. In another embodiment, the solid, oral dosage form provides an $AUC_{0-t}$ (0-24 hours) of about 13,000-14,000 hr ng/mL after a single administration. In another embodiment, the solid, oral dosage form provides an $AUC_{0-t}$ (0-24 hours) of about 15,000-16,000 h·ng/mL after a single administration. In another embodiment, the solid, oral dosage form provides an $AUC_{0-t}$ (0-24 hours) of about 4,000 h·ng/mL after a single administration. In another embodiment, the solid, oral dosage form provides an $AUC_{0-t}$ (0-24 hours) of about 4,500 h·ng/mL after a single administration. In another embodiment, the solid, oral dosage form provides an $AUC_{0-t}$ (0-24 hours) of about 5,000 h·ng/mL after a single administration. In another embodiment, the solid, oral dosage form provides an $AUC_{0-t}$ (0-24 hours) of about 5,500 h·ng/mL after a single administration. In another embodiment, the solid, oral dosage form provides an $AUC_{0-t}$ (0-24 hours) of about 6,000 h·ng/mL after a single administration. In another embodiment, the solid, oral dosage form provides an $AUC_{0-t}$ (0-24 hours) of about 6,500 h·ng/mL after a single administration. In another embodiment, the solid, oral dosage form provides a $C_{max}$ of about 90-1100 ng/mL and an $AUC_{0-t}$ (0-24 hours) of about 800-15,000 h·ng/mL after a single administration. In another embodiment, the solid, oral dosage form provides a $C_{max}$ of about 200-1,200 ng/mL and an $AUC_{0-t}$ (0-24 hours) of about 2,500-9,500 h·ng/mL after a single administration. In another embodiment, the solid, oral dosage form provides a $C_{max}$ of about 200-1,200 ng/mL and an $AUC_{0-t}$ (0-24 hours) of about 2,500-9,300 h·ng/mL after a single administration. In another embodiment, the solid, oral dosage form provides a $C_{max}$ of about 200-800 ng/mL and an $AUC_{0-t}$ (0-24 hours) of about 2,000-15,000 h·ng/mL after a single administration. In another embodiment, the solid, oral dosage form provides a $C_{max}$ of about 200-300 ng/mL and an $AUC_{0-t}$ (0-24 hours) of about 2,000-4,000 h·ng/mL after a single administration. In another embodiment, the solid, oral dosage form provides a $C_{max}$ of about 300-400 ng/mL and an $AUC_{0-t}$ (0-24 hours) of about 4,000-7,000 h·ng/mL after a single administration. In another embodiment, the solid, oral dosage form provides a $C_{max}$ of about 400-500 ng/mL and an $AUC_{0-t}$ (0-24 hours) of about 5,000-6,000 hr·ng/mL after a single administration.

In another embodiment, the solid, oral dosage form provides a $C_{max}$ of about 600-700 ng/mL and an $AUC_{0-t}$ (0-24 hours) of about 14,000-15,000 h·ng/mL after a single administration. In another embodiment, the solid, oral dosage form provides a $C_{max}$ of about 700-800 ng/mL and an $AUC_{0-t}$ (0-24 hours) of about 10,000-11,000 hr·ng/mL after a single administration.

In another embodiment, the solid, oral dosage form provides an $AUC_{0-t}$ (0-168 hours) of about 1,000-70,000 hr·ng/mL after one week, 1-7 days per week, of administration. In another embodiment, the solid, oral dosage form provides an $AUC_{0-t}$ (0-168 hours) of about 10,000-70,000 hr·ng/mL after one week, 3-7 days per week, of administration. In another embodiment, the solid, oral dosage form provides an $AUC_{0-t}$ (0-168 hours) of about 20,000-60,000 h·ng/mL after one week, 3-7 days per week, of administration. In another embodiment, the solid, oral dosage form provides an $AUC_{0-t}$ (0-168 hours) of about 20,000-70,000 hr·ng/mL after one week, 5-7 days per week, of administration. In another embodiment, the solid, oral dosage form provides an $AUC_{0-t}$ (0-168 hours) of about 30,000-60,000 hr·ng/mL after one week, 5-7 days per week, of administration. In another embodiment, the solid, oral dosage form provides an $AUC_{0-t}$ (0-168 hours) of about 4,000-10,000 hr·ng/mL after one week, one day per week, of administration. In another embodiment, the solid, oral dosage form provides an $AUC_{0-t}$ (0-168 hours) of about 6,000-8,000 hr·ng/mL after one week, one day per week, of administration. In another embodiment, the solid, oral dosage form provides an $AUC_{0-t}$ (0-168 hours) of about 6,500-7,500 hr·ng/mL after one week, one day per week, of administration. In another embodiment, the solid, oral dosage form provides an $AUC_{0-t}$ (0-168 hours) of about 7,000 hr·ng/mL after one week, one day per week, of administration. In another embodiment, the solid, oral dosage form provides an $AUC_{0-t}$ (0-168 hours) of about 10,000-35,000 hr·ng/mL after one week, 3 days per week, of administration. In another embodiment, the solid, oral dosage form provides an $AUC_{0-t}$ (0-168 hours) of about 15,000-30,000 hr·ng/mL after one week, 3 days per week, of administration. In another embodiment, the solid, oral dosage form provides an $AUC_{0-t}$ (0-168 hours) of about 20,000-25,000 hr·ng/mL after one week, 3 days per week, of administration. In another embodiment, the solid, oral dosage form provides an $AUC_{0-t}$ (0-168 hours) of about 20,000-60,000 hr·ng/mL after one week, 5 days per week, of administration. In another embodiment, the solid, oral dosage form provides an $AUC_{0-t}$ (0-168 hours) of about 25,000-55,000 hr·ng/mL after one week, 5 days per week, of administration. In another embodiment, the solid, oral dosage form provides an $AUC_{0-t}$ (0-168 hours) of about 30,000-50,000 hr·ng/mL after one week, 5 days per week, of administration. In another embodiment, the solid, oral dosage form provides an $AUC_{0-t}$ (0-168 hours) of about 30,000-75,000 hr·ng/mL after one week, 7 days per week, of administration. In another embodiment, the solid, oral dosage form provides an $AUC_{0-t}$ (0-168 hours) of about 35,000-70,000 hr·ng/mL after one week, 7 days per week, of administration. In another embodiment, the solid, oral dosage form provides an $AUC_{0-t}$ (0-168 hours) of about 40,000-65,000 hr·ng/mL after one week, 7 days per week, of administration.

In another embodiment, the compound of formula (I) or pharmaceutically acceptable salt thereof is administered at a dosage of about 100-1,200 mg/day 1-7 days per week, up to about 3,000 mg/week. In another embodiment, the dosage is about 100-1,200 mg/day 1-7 days per week, up to about 2,800 mg/week. In another embodiment, the dosage is about 100-1,200 mg/day 1-7 days per week, up to about 2,000 mg/week. In another embodiment, the dosage is about 100-600 mg/day 1-7 days per week. In another embodiment, the dosage is about 100-600 mg/day 3-7 days per week. In another embodiment, the dosage is about 100-600 mg/day 5-7 days per week. In another embodiment, the dosage is about 100-600 mg/day 3 days per week. In another embodiment, the dosage is about 100-600 mg/day 4 days per week. In another embodiment, the dosage is about 100-600 mg/day 5 days per week. In another embodiment, the dosage is about 100-600 mg/day 6 days per week. In another embodiment, the dosage is about 100-600 mg/day 7 days per week.

In another embodiment, the dosage is about 200-500 mg/day 1-7 days per week. In another embodiment, the dosage is about 200-500 mg/day 3-7 days per week. In another embodiment, the dosage is about 200-500 mg/day 5-7 days per week. In another embodiment, the dosage is about 200-500 mg/day 3 days per week. In another embodiment, the dosage is about 200-500 mg/day 4 days per week. In another embodiment, the dosage is about 200-500 mg/day 5 days per week. In another embodiment, the dosage is about 200-500 mg/day 6 days per week. In another embodiment, the dosage is about 200-500 mg/day 7 days per week.

In another embodiment, the dosage is about 150-400 mg/day 1-7 days per week. In another embodiment, the dosage is about 150-400 mg/day 3-7 days per week. In another embodiment, the dosage is about 150-400 mg/day 5-7 days per week. In another embodiment, the dosage is about 150-400 mg/day 3 days per week. In another embodiment, the dosage is about 150-400 mg/day 4 days per week. In another embodiment, the dosage is about 150-400 mg/day 5 days per week. In another embodiment, the dosage is about 150-400 mg/day 6 days per week. In another embodiment, the dosage is about 150-400 mg/day 7 days per week.

In another embodiment, the dosage is about 200 mg/day 1-7 days per week. In another embodiment, the dosage is about 200 mg/day 3-7 days per week. In another embodiment, the dosage is about 200 mg/day 5-7 days per week. In another embodiment, the dosage is about 200 mg/day 3 days per week. In another embodiment, the dosage is about 200 mg/day 4 days per week. In another embodiment, the dosage is about 200 mg/day 5 days per week. In another embodiment, the dosage is about 200 mg/day 6 days per week. In another embodiment, the dosage is about 200 mg/day 7 days per week.

In another embodiment, the dosage is about 250 mg/day 1-7 days per week. In another embodiment, the dosage is about 250 mg/day 3-7 days per week. In another embodiment, the dosage is about 250 mg/day 5-7 days per week. In another embodiment, the dosage is about 250 mg/day 3 days per week. In another embodiment, the dosage is about 250 mg/day 4 days per week. In another embodiment, the dosage is about 250 mg/day 5 days per week. In another embodiment, the dosage is about 250 mg/day 6 days per week. In another embodiment, the dosage is about 250 mg/day 7 days per week.

In another embodiment, the dosage is about 300 mg/day 1-7 days per week. In another embodiment, the dosage is about 300 mg/day 3-7 days per week. In another embodiment, the dosage is about 300 mg/day 5-7 days per week. In another embodiment, the dosage is about 300 mg/day 3 days per week. In another embodiment, the dosage is about 300 mg/day 4 days per week. In another embodiment, the dosage is about 300 mg/day 5 days per week. In another embodiment, the dosage is about 300 mg/day 6 days per week. In another embodiment, the dosage is about 300 mg/day 7 days per week.

In another embodiment, the dosage is about 350 mg/day 1-7 days per week. In another embodiment, the dosage is about 350 mg/day 3-7 days per week. In another embodiment, the dosage is about 350 mg/day 5-7 days per week. In another embodiment, the dosage is about 350 mg/day 3 days per week. In another embodiment, the dosage is about 350 mg/day 4 days per week. In another embodiment, the dosage is about 350 mg/day 5 days per week. In another embodiment, the dosage is about 350 mg/day 6 days per week. In another embodiment, the dosage is about 350 mg/day 7 days per week.

In another embodiment, the dosage is about 400 mg/day 1-7 days per week. In another embodiment, the dosage is about 400 mg/day 3-7 days per week. In another embodiment, the dosage is about 400 mg/day 5-7 days per week. In another embodiment, the dosage is about 400 mg/day 3 days per week. In another embodiment, the dosage is about 400 mg/day 4 days per week. In another embodiment, the dosage is about 400 mg/day 5 days per week. In another embodiment, the dosage is about 400 mg/day 6 days per week. In another embodiment, the dosage is about 400 mg/day 7 days per week.

Daily dosage is based upon an adult human having a weight or body mass of about 60-80 kg. Thus, for a range of about 100-1,200 mg/day, the dosage can range from about 1-20 mg/kg/day up to about 50 mg/kg/week. Additional dosages based on subject weight may be readily calculated from these values. Similarly, persons skilled in the art will be able to calculate dosages for other species based on known correlations to human dosages.

The total daily dose can be administered in one or more doses. In one embodiment, the oral dosage form is administered once daily. In another embodiment, the oral dosage form is administered twice daily. In another embodiment, the oral dosage form is administered three times daily. In another embodiment, the oral dosage form is administered four times daily.

In embodiments, the oral dosage form is administered at a dosage of up to about 12,000 mg/month. The total monthly dose can be administered 1-7 days per week either for three weeks followed by one week of rest, or for four weeks without rest. For each week of treatment, the oral dosage form may be administered 1-7 days per week. In one embodiment, the oral dosage form is administered for three weeks followed by one week of rest. In another embodiment, the oral dosage form is administered 3-7 days per week for three weeks followed by one week of rest. In another embodiment, the oral dosage form is administered 5-7 days per week for three weeks followed by one week of rest. In another embodiment, the oral dosage form is administered daily for three weeks followed by one week of rest. In another embodiment, the oral dosage form is administered daily for 28 days. Each dosing cycle consists of either 3 weeks of treatment followed by 1 week of rest, or 4 continuous weeks of treatment. The dosing cycle may be repeated as often as necessary as determined by a person skilled in the art. In one embodiment, the oral dosage form is administered for up to 12 dosing cycles. In one embodiment, the oral dosage form is administered for up to 6 dosing cycles.

In any embodiment, the tumor is selected from gastrointestinal, genitourinary, skin, colorectal (colon or rectal), ovarian, lung, breast, pancreatic, stomach and renal cancer. In another embodiment, the tumor is gastrointestinal cancer. In some embodiments, the tumor is genitourinary cancer. In another embodiment, the tumor is skin cancer. In another embodiment, the tumor is melanoma. In another embodiment, the tumor is colorectal cancer. In another embodiment, the tumor is colon cancer. In another embodiment, the tumor is rectal cancer. In another embodiment, the tumor is K-Ras mutant colon cancer. In another embodiment, the tumor is ovarian cancer. In another embodiment, the tumor is platinum-resistant or -refractory (e.g., cisplatin- or carboplatin-resistant) ovarian cancer. In another embodiment, the tumor is lung cancer. In another embodiment, the tumor is non-small cell lung cancer. In another embodiment, the tumor is breast cancer. In another embodiment, the tumor is triple-negative (TN) breast cancer. In another embodiment, the tumor is metastatic breast cancer. In another embodiment, the tumor is pancreatic cancer. In another embodiment, the tumor is stomach cancer. In another embodiment, the tumor is renal cancer.

In another embodiment, the subject is a mammal. In another embodiment, the subject is a human.

4.3 Methods of Inhibiting β-Catenin Dependent ATPase Activity of Y593 Phosphorylated p68

Another aspect of the disclosure provides a method of inhibiting β-catenin dependent ATPase activity of Y593 phosphorylated p68, comprising administering to a subject in need thereof an effective amount of a compound of formula (I) or pharmaceutically acceptable salt thereof.

4.4 Methods of Predicting Efficacy of Treatment

Another aspect of the disclosure provides a method of predicting efficacy of treatment of a subject in need thereof with a compound of formula (I) or pharmaceutically acceptable salt thereof, comprising:

(a) collecting a sample of the tumor from the subject;

(b) determining whether the tumor expresses Y593 phosphorylated p68.

In one embodiment, the method also includes administering the compound of formula (I) or pharmaceutically acceptable thereof to the subject if the tumor expresses Y593 phosphorylated p68.

In another embodiment, the method also includes determining whether the compound of formula (I) or pharmaceutically acceptable salt thereof inhibits β-catenin dependent ATPase activity of the Y593 phosphorylated p68. In another embodiment, the method includes administering the compound of formula (I) or pharmaceutically acceptable thereof to the subject if inhibition of β-catenin dependent ATPase activity and expression of Y593 phosphorylated p68 are detected.

In another embodiment, the method also includes the step of determining whether the compound of formula (I) or pharmaceutically acceptable thereof inhibits RNA-dependent ATPase activity of the Y593 phosphorylated p68. In another embodiment, the method includes administering the compound of formula (I) or pharmaceutically acceptable salt thereof to the subject only if inhibition of RNA-dependent ATPase activity is not detected.

In another embodiment, method also includes determining whether the compound of formula (I) or pharmaceutically acceptable salt thereof inhibits translocation of β-catenin into the tumor's cell nucleus. In another embodiment, the method includes determining whether the compound of formula (I) or pharmaceutically acceptable salt thereof decreases intracellular levels of β-catenin. In another embodiment, the method includes determining whether the compound of formula (I) or pharmaceutically acceptable salt thereof inhibits expression of one or more genes regulated by β-catenin. In another embodiment, the method also includes administering the compound of formula (I) or pharmaceutically acceptable salt thereof to the subject only if inhibition of the expression of the one or more genes regulated by β-catenin is detected. In another embodiment, the method also includes administering the compound of formula (I) or pharmaceutically acceptable salt thereof to the subject only if inhibition of the β-catenin-TCF-4 mediated transcription activity is detected. In another embodiment, the method also includes administering the compound of formula (I) or pharmaceutically acceptable salt thereof to the subject only if inhibition of the Wnt signaling activity is detected. In another embodiment, the one or more genes are selected from cyclin D1, c-Myc, Axin2, Surviv1, and p-c-Jun.

In embodiments, the subject is a mammal. In another embodiment, the subject is a human.

In any embodiment, the tumor is selected from gastrointestinal, genitourinary, skin, colorectal (colon or rectal), ovarian, lung, breast, pancreatic, stomach and renal cancer. In another embodiment, the tumor is gastrointestinal cancer. In some embodiments, the tumor is genitourinary cancer. In another embodiment, the tumor is skin cancer. In another embodiment, the tumor is melanoma. In another embodiment, the tumor is colorectal cancer. In another embodiment, the tumor is colon cancer. In another embodiment, the tumor is rectal cancer. In another embodiment, the tumor is K-Ras mutant colon cancer. In another embodiment, the tumor is ovarian cancer. In another embodiment, the tumor is platinum-resistant or -refractory (e.g., cisplatin- or carboplatin-resistant) ovarian cancer. In another embodiment, the tumor is lung cancer. In another embodiment, the tumor is non-small cell lung cancer. In another embodiment, the tumor is breast cancer. In another embodiment, the tumor is triple-negative (TN) breast cancer. In another embodiment, the tumor is metastatic breast cancer. In another embodiment, the tumor is pancreatic cancer. In another embodiment, the tumor is stomach cancer. In another embodiment, the tumor is renal cancer.

4.5 Kits for Testing Efficacy of Treatment

Another aspect of the disclosure provides a kit for testing potential efficacy of a compound of formula (I) or pharmaceutically acceptable salt thereof in treating a tumor, where the kit includes an assay that determines whether the tumor expresses Y593 phosphorylated p68.

In one embodiment, the kit also includes an assay that detects inhibition of β-catenin dependent ATPase activity of the Y593 phosphorylated p68. In another embodiment, the kit further includes an assay that detects intracellular levels (e.g., cytosolic and nuclear levels) of β-catenin. In another embodiment, the kit includes an assay that detects inhibition of the expression of one or more genes regulated by β-catenin. In another embodiment, the one or more genes are selected from cyclin D41, c-Myc and p-c-Jun.

4.6 Pharmaceutical Compositions

In any of the methods and kits provided herein, the compound of formula (I) or pharmaceutically acceptable salt thereof may be in a pharmaceutical composition. Such pharmaceutical composition can be prepared as any appropriate unit dosage form. For example, the pharmaceutical compositions can be formulated for administration in solid or liquid form, including those adapted for the following: (1) oral administration, for example, as drenches, tablets (such as those targeted for buccal, sublingual and systemic absorption, including over-encapsulation tablets), capsules (such as hard, soft, dry-filled, liquid-filled, gelatin, non-gelatin or over-encapsulation capsules), caplets, boluses, powders, sachets, granules, pastes, mouth sprays, troches, lozenges, pellets, syrups, suspensions, elixirs, liquids, liposomes, emulsions and microemulsions; or (2) parenteral administration by, for example, subcutaneous, intramuscular, intravenous or epidural injection as, for example, a sterile solution or suspension. Additionally, the pharmaceutical compositions can be formulated for immediate, sustained, extended, delayed or controlled release.

In one embodiment, the pharmaceutical composition is formulated for oral administration. In another embodiment, the pharmaceutical composition is a solid, oral dosage form. In another embodiment, the pharmaceutical composition is a solid, oral dosage form that provides a $T_{max}$, $C_{max}$, $AUC_{0-t}$ or combination thereof as described herein (see Section 4.2). In another embodiment, the pharmaceutical composition is a tablet or capsule. In another embodiment, the pharmaceutical composition is a tablet. In another embodiment, the pharmaceutical composition is a capsule. In another embodiment, the tablet or capsule is formulated for immediate release. In another embodiment, the tablet or capsule is formulated for sustained, extended, delayed or controlled release.

In another embodiment, the tablet or capsule also include at least one pharmaceutically acceptable carrier. Carriers include any substance that may be administered with the pharmaceutical composition with the intended purpose of facilitating, assisting, or helping the administration or other delivery of the pharmaceutical composition and/or improve the bioavailability of the pharmaceutical composition. Carriers may include any liquid, solid, semisolid, gel aerosol or others substances that may be combined with the pharmaceutical composition to aid in its administration. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers may include polyethylene glycol, cyclodextrin, oils, or any other similar liquid carrier that may be formulated into a capsule. Examples of suitable carriers may include diluents, adjuvants, excipients, water, lipidic formulations and oils, such as petroleum, animal, vegetable or synthetic oils. Suitable excipients may include water-insoluble surfactants, water-soluble surfactants, and hydrophilic cosolvents. Suitable oils may include tri, di or monoglycerides.

In another embodiment, nanoparticles of RX-5902 can be prepared and formulated as suspensions, tablets, capsules or other dosage forms, such as disclosed in U.S. Pat. Pub. No. US20150004234 (published Jan. 1, 2015). In one embodiment, the nanoparticles have a median particle size (D50) of less than about 1,000 nm. In another embodiment, the nanoparticles have a median particle size (D50) of less than about 500 nm. In another embodiment, nanoparticles of RX-5902 are formulated as a suspension. In another embodiment, the suspension is dried, such as by lyophilization, to form a powder. In another embodiment, the powder is combined with one or more pharmaceutically acceptable excipients. In another embodiment, the powder is encapsulated into capsules.

The composition and preparation of capsules are well known in the art. For example, capsules may be prepared from gelatin (e.g., Type A, Type B), carrageenan (e.g., kappa, iota, lambda) and/or modified cellulose (e.g., hydroxypropyl methyl cellulose, methyl cellulose, hydroxypropyl methyl cellulose acetate succinate, hydroxypropyl methyl cellulose phthalate, cellulose acetate phthalate), and optionally one or more excipients such as oils (e.g., fish oil, olive oil, corn oil, soybean oil, coconut oil, tri-, di- and monoglycerides), plasticizers (e.g., glycerol, glycerin, sorbitol, polyethylene glycol, citric acid, citric acid esters such as triethylcitrate, polyalcohols), co-solvents (e.g., triacetin, propylene carbonate, ethyl lactate, propylene glycol, oleic acid, dimethylisosorbide, stearyl alcohol, cetyl alcohol, cetostearyl alcohol, glyceryl behenate, glyceryl palmitostearate), surfactants, buffering agents, lubricating agents, humectants, preservatives, colorants and flavorants. Capsules may be hard or soft. Examples of hard capsules include Coni-Snap®, DRcaps™, OceanCaps®, Pearlcaps®, Plantcaps®, DUOCAP™, Vcaps® and Vcaps® Plus capsules available from Capsugel®. Hard capsules may be prepared, for example, by forming two telescoping capsule halves, filling one of the halves with a fill comprising a compound of formula (I) or pharmaceutically acceptable salt thereof, and sealing the capsule halves together. The fill may be in any suitable form, such as dry powder, granulation, suspension or liquid. Examples of soft capsules include soft gelatin (also called softgel or soft elastic) capsules, such as SGcaps®. Soft capsules may be prepared, for example, by rotary die, plate, reciprocating die or Accogel® machine method. In embodiments, the capsule may be a liquid-filled hard capsule or a soft-gelatin capsule.

Tablets can be made by compression or molding, optionally with one or more accessory ingredients. Compressed tablets can be prepared by compressing in a suitable machine a compound of formula (I) or pharmaceutically acceptable salt thereof in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide sustained, extended, delayed or controlled release. Methods of formulating such sustained, extended, delayed or controlled release compositions are known in the art and disclosed in issued U.S. patents, including but not limited to U.S. Pat. Nos. 4,369,174, 4,842,866, and the references cited therein. Coatings, for example enteric coatings, can be used for delivery of compounds to the intestine (see, e.g., U.S. Pat. Nos. 6,638,534, 5,217,720, 6,569,457, and the references cited therein). In addition to tablets, other dosage forms, such as capsules, granulations and gel-caps, can be formulated to provide sustained, extended, delayed or controlled release.

In another embodiment, the pharmaceutical composition is formulated for parenteral administration. Examples of a pharmaceutical composition suitable for parenteral administration include aqueous sterile injection solutions and non-aqueous sterile injection solutions, each containing, for example, anti-oxidants, buffers, bacteriostats and/or solutes that render the formulation isotonic with the blood of the intended recipient; and aqueous sterile suspensions and non-aqueous sterile suspensions, each containing, for example, suspending agents and/or thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use. In one embodiment, the pharmaceutical composition is formulated for intravenous administration.

In embodiments, the pharmaceutical composition further includes a pharmaceutically acceptable excipient. A pharmaceutically acceptable excipient may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in *Remington: The Science and Practice of Pharmacy*, 21$^{st}$ Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropyl methylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In embodiments, the pharmaceutical composition can include at least one additional active agent. The active agent may be an antineoplastic, chemotherapeutic, cytotoxic, immunomoduloar, radiotherapeutic or any other agent capable of inducing apoptosis, sensitizing a cell to apoptosis, modulating protein kinase or treating neoplasm, tumor or cancer. Examples of the active agent include: (1) antimetabolites, such as cytarabine, fludarabine, 5-fluoro-2'-deoxyuiridine, gemcitabine, 4-amino-1-((1S,4R,5S)-2-fluoro-4,5-dihydroxy-3-hydroxymethyl-cyclopent-2-enyl)-1H-pyrimidin-2-one (RX-3117), hydroxyurea or methotrexate; (2) DNA-fragmenting agents, such as bleomycin, (3) DNA-crosslinking agents, such as chlorambucil, cisplatin, cyclophosphamide and nitrogen mustard; (4) intercalating agents such as adriamycin (doxorubicin) and mitoxantrone; (5) protein synthesis inhibitors, such as L-asparaginase, cycloheximide, puromycin and diphtheria toxin; (6) topoisomerase I poisons, such as camptothecin and topotecan; (7) topoisomerase II poisons, such as etoposide (VP-16) and teniposide; (8) microtubule-directed agents, such as colcemid, colchicine, paclitaxel, vinblastine and vincristine; (9) kinase inhibitors such as flavopiridol, staurosporin and 7-hydroxystaurosporine; (10) enzyme poly ADP ribose polymerase (PARP) inhibitors such as olaparib, veliparib, rucaparib, niraparib, and talazoparib (11) polyphenols such as quercetin, resveratrol, piceatannol, epigallocatechine gallate, theaflavins, flavanols, procyanidins, betulinic acid and derivatives thereof; (12) hormones such as glucocorticoids and fenretinide; (13) hormone antagonists, such as tamoxifen, finasteride and LHRH antagonists; (14) death receptor agonists, such as tumor necrosis factor α (TNF-α), tumor necrosis factor 13 (TNF-β), LT-β (lymphotoxin-β), TRAIL (Apo2L, DR4 ligand), CD95 (Fas, APO-1) ligand, TRAMP (DR3, Apo-3) ligand, DR6 ligand and fragments; (15) immune checkpoint inhibitors; (16) anti-programmed cell death 1 (PD-1) receptor antibodies or anti-programmed cell death ligand 1 (PD-L1) antibodies; (17) immune checkpoint inhibitors (CTLA-4); and derivatives thereof.

In another embodiment, the amount of the compound of formula (I) or pharmaceutically acceptable salt in the pharmaceutical composition is between about 0.1% and about 5% by weight. In another embodiment, the amount is between about 0.5% and about 2.5% by weight.

4.7 Methods of Administration

In any of the methods provided herein, administration of the compound or pharmaceutical composition may be via any accepted mode known in the art, such as orally or parenterally. The term "parenterally" includes without limitation subcutaneously, intravenously, intramuscularly, intraperitoneally, intrathecally, intraventricularly, intrasternally, intracranially, by intraosseous injection and by infusion techniques. In one embodiment, the compound or pharmaceutical composition is administered orally. In another embodiment, the compound or pharmaceutical composition is administered parenterally. In another embodiment, the compound or pharmaceutical composition is administered intravenously. In another embodiment, the compound or pharmaceutical composition is administered intratumorally.

In one embodiment, the compound or pharmaceutical composition is administered orally at a dose or dosage as disclosed herein, such as in Section 4.2.

The dose level can be adjusted for intravenous administration. In such case, the compound or pharmaceutical composition can be administered in an amount of between about 0.01 µg/kg/min to about 100 µg/kg/min.

4.8 Combination Therapy

In any of the methods of treating or preventing a tumor provided herein, the method may also include the step of administering one or more additional anti-tumor agent or radiation to the subject. In one embodiment, the method includes administering radiation to the subject. In another embodiment, the method further includes administering one or more additional anti-tumor agent to the subject.

The additional anti-tumor agent or radiation may be administered before, after, or during administration of the compound of formula (I) or pharmaceutically acceptable salt thereof. In one embodiment, the additional anti-tumor agent or radiation is administered before administration of the compound of formula (I) or pharmaceutically acceptable salt thereof. In another embodiment, the additional anti-tumor agent or radiation is administered after administration of the compound of formula (I) or pharmaceutically acceptable salt thereof. In another embodiment, the additional anti-tumor agent or radiation is administered during administration of the compound of formula (I) or pharmaceutically acceptable salt thereof. In another embodiment, the additional anti-tumor agent and the compound of formula (I) or pharmaceutically acceptable salt thereof are formulated into a pharmaceutical composition for concurrent administration.

The term "anti-tumor agent," as used herein, refers to any agent useful for treating or preventing tumor. Examples of an anti-tumor agent include the active agents described in Section 4.6. In one embodiment, the additional anti-tumor agent is selected from antimetabolites, DNA-fragmenting agents, DNA-crosslinking agents, intercalating agents, protein synthesis inhibitors, topoisomerase I inhibitors, topoisomerase II inhibitors, microtubule-directed agents, kinase inhibitors (e.g.; tyrosine kinase inhibitors), polyphenols, hormones, hormone antagonists, death receptor agonists, enzyme poly ADP ribose polymerase (PARD) inhibitor, immune checkpoint inhibitors, anti-programmed cell death 1 (PD-1) receptor antibodies and anti-programmed cell death ligand 1 (PD-L1) antibodies. In another embodiment, the additional anti-tumor agent is a PD-1 receptor antibody. In another embodiment, the additional anti-tumor agent is pembrolizumab. In another embodiment, the additional anti-tumor agent is nivolumab. In another embodiment, the additional anti-tumor agent is tremelimumab. In another embodiment, the additional anti-tumor agent is ipilinumab. In another embodiment, the additional anti-tumor agent is a combination of nivolumab and ipilinumab. In another embodiment, the additional anti-tumor agent is a combination of pembrolizumab and tremelimumab.

4.9. Process of Making RX-5902

U.S. Pat. No. 8,314,100 discloses a process of converting 3-amino-2-chloro-6-fluoroquinoxaline to RX-5902 in 3 steps, through intermediates 3-amino-6-fluoro-2-methoxyquinoxaline and ethyl N-(6-fluoro-2-methoxyquinoxaline-3-yl)carbamate.

During the small batch process of the reaction, a demethylated impurity (based on Mass Spec data) was detected and purification was required for its removal. Furthermore, the small batch process requires intermediates to be concentrated to dryness. Thus, the process is unsatisfactory for commercial scale production. Therefore, there is a need to provide an improved process amenable to scale up in fixed equipment to allow for efficient commercial production. For example, the process was improved by removing the concentration to dryness, substituting some of the halogenated solvents with non-halogenated solvents and by improving the volume inefficient recrystallization of Compound 1 in the small batch manufacturing process.

Below details the small batch production and the improved production process of RX-5902.

4.9.1 Small Batch Production of 1.5 kg of RX-5902 Drug Substance

Scheme 1. Small Batch Synthetic Process for the Production of RX-5902

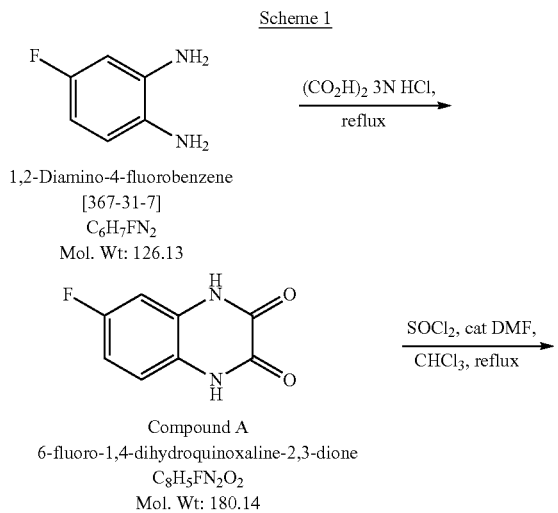

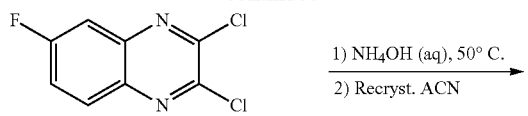

Compound B
2,3-dichloro-6-fluoroquinoxaline
C$_8$H$_3$Cl$_2$FN$_2$
Mol. Wt: 217.02

1) NH$_4$OH (aq), 50° C.
2) Recryst. ACN

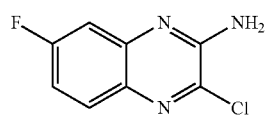

Compound 1
3-amino-2-chloro-6-fluoroquinoxaline
[888480-65-7]
C$_8$H$_5$ClFN$_3$
Mol. Wt: 197.60

25% NaOMe/MeOH
THF, RT

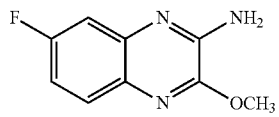

Compound 2
3-amino-6-fluoro-2-methoxyquinoxaline
[88480-37-3]
C$_9$H$_8$FN$_3$O
Mol. Wt: 193.18

ClCO$_2$CH$_2$CH$_3$, DCM,
pyriine, RT

Compound 3
E-116
Ethyl-N-(6-fluoro-
2-methoxyquinoxaline-3-yl)
carbonate
C$_{12}$H$_{12}$FN$_3$O$_3$
Mol. Wt: 265.24

1-(3,5-dimethoxyphenyl)
piperazine HCl (DMPP)
C$_{12}$H$_{19}$ClN$_2$O$_2$
Mol. Wt: 258.75
DBU, THF, 70° C.

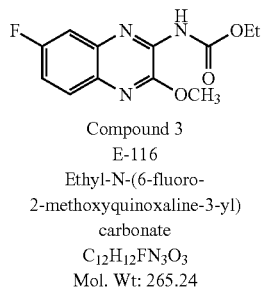

RX-5902 (D-158)
[888478-45-3]
C$_{22}$H$_{24}$FN$_5$O$_4$
Mol. Wt: 441.46

The present invention provides a method of preparing a compound of formula (I).

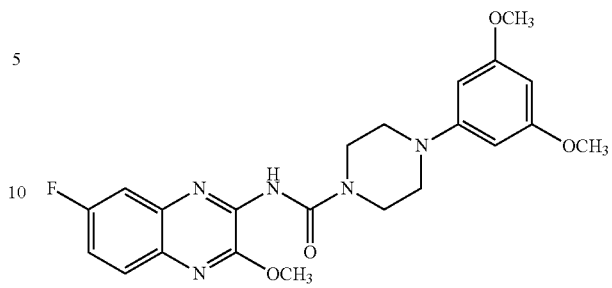

(I)

or pharmaceutically acceptable salt thereof on a commercial scale, by: (a) reacting 3-amino-6-fluoro-2-methoxyquinoxaline with ethyl chloroformate in an organic solvent in the presence of a base to form a mixture; (b) distilling the mixture while adding ethyl acetate to form a suspension; (c) filtering the suspension to isolate ethyl-N-(6-fluoro-2-methoxyquinoxaline-3-yl) carbonate; and (d) reacting the ethyl-N-(6-fluoro-2-methoxyquinoxaline-3-yl) carbonate with 1-(3,5-dimethoxyphenyl) piperazine hydrochloride in a second organic solvent in the presence of a second base.

A 1.5 kg scale current good manufacturing practice (cGMP) production of 4-(3, 5-dimethoxyphenyl)-N-(7-fluoro-3-methoxyquinoxalin-2-yl)piperazine-1-carboxamide (RX-5902) was conducted. The initial production afforded 1.318 kg of RX-5902. However, when release testing was performed, an unspecified impurity at RRT 0.57 was found to be out of specification (result: 0.82% vs. limit≤0.50%). The impurity was later identified by mass spectrometry to correspond to what is believed to be demethylated RX-5902. A base wash rework procedure was successfully developed and implemented, ultimately affording 1.128 kg (designated as batch 35444A).

Embodiments of the method may include: (e) reacting 3-amino-2-chloro-6-fluoroquinoxaline with sodium methoxide in an organic solvent in the presence of a base to form a mixture; (f) adding water to the mixture of step (e) to form a solution; (g) cooling the solution to a temperature of about 15-20° C. to form a suspension; and (h) filtering the suspension of step (g) to isolate 3-amino-6-fluoro-2-methoxyquinoxaline.

In embodiments, the organic solvent in step (a) may be dichloromethane. In embodiments, the base in step (a) may be pyridine. In embodiments, the distilling step (b) may be conducted under atmospheric pressure. In embodiments, step (c) may be by vacuum filtration. In embodiments, the second organic solvent in step (d) may be tetrahydrofuran. In embodiments, the second base in step (d) may be 1,8-diazabicycloundec-7-ene. In embodiments, the steps may be performed in one or more fixed reactors.

4.9.2 Large Scale Synthetic Production of 11 kg of RX-5902

The present invention provides an improved process of preparing RX-5902, which is commercially viable for large scale production. The process improves the small batch manufacturing process of RX-5902 to allow scale up in fixed equipment for commercial scale production to significantly reduce the cost of manufacture. The inventive process removed the concentration to dryness step, replaced some of the halogenated solvents and improved the volume inefficient recrystallization of Compound 1 used in the small batch manufacturing process.

Scheme 2 illustrates an improved process for fixed reactors/large scale production of RX-5902. As shown in Scheme 2, Embodiments of the method can include preparing RX-5902 by reacting ethyl-N-(6-fluoro-2-methoxyquinoxaline-3-yl)carbonate (Compound 3) with 1-(3,5-dimethoxyphenyl) piperazine hydrochloride in an organic solvent in the presence of a base until the reaction is complete as indicated by HPLC. In an embodiment, the organic solvent may be tetrahydrofuran. In an embodiment, the base may be 1,8-diazabicycloundec-7-ene (DBU).

Embodiments of the method can include reacting Compound 2 with ethyl chloroformate in an organic solvent in the presence of a base to form Compound 3. In an embodiment, Compound 2 may be dissolved in the organic solvent in the presence of the base before ethyl chloroformate is slowly added to the solution. In an embodiment, the organic phase may be extracted with DI water and the organic phase may be distilled under atmospheric pressure to remove the organic solvent. In an embodiment, ethyl acetate may be added during the distillation process. In an embodiment, Compound 3 in solid form may be collected by vacuum filtration and washed with ethyl acetate and dried. In an embodiment, the organic solvent may be dichloromethane. In an embodiment, the base may be pyridine.

Embodiments of the method can include converting Compound 1 to 3-amino-6-fluoro-2-methoxyquinoxaline (Compound 2) with sodium methoxide in tetrahydrofuran until completion. In an embodiment, water may be added to the solution mixture. In an embodiment, the solution may be cooled to a temperature of about 15-20° C. In an embodiment, the reaction mixture may be concentrated through atmospheric distillation to remove tetrahydrofuran and reduce the volume to less than half. In an embodiment, Compound 2 may be washed with water and collected by filtering.

Embodiments of the method can include a six-step process of making RX-5902 with 1,2-diamino-4-fluorbenzene as the starting material. In an embodiment, the process utilizes fixed equipment for a scale up process suitable for cGMP production of RX-5902.

Embodiments of the method can include converting 1,2-diamino-4-fluorbenzene to 6-fluoro-1,4-dihdryoquinoxaline-2,3-dione (Compound A) by reacting 1,2-diamino-4-fluorbenzene with oxalic acid. Compound A may be precipitated and collected by vacuum filtration.

Embodiments of the method can include converting Compound A to 2,3-dichloro-6-fluoroquinoxaline (Compound B) by refluxing compound A with excess thionyl chloride in chloroform until completion. In an embodiment, the reaction may be quenched with sodium hydroxide and stirred until the remaining thionyl chloride are decomposed. In an embodiment, chloroform may be distilled away via atmospheric distillation. In an embodiment, heptane may be added during distillation. In an embodiment, Compound B may be filtered and washed with heptane and dried in a vacuum. In an embodiment, the filtrate (i.e. mother liquor) may be distilled under vacuum to recover additional Compound B.

Embodiments of the method can include converting Compound B to 3-amino-2-chloro-6-fluoroquinoxaline (Compound 1) with ammonium hydroxide until completion. In an embodiment, Compound 1 may be purified by filtering the reaction mixture warm, i.e. at an elevated temperature of 45±5° C.

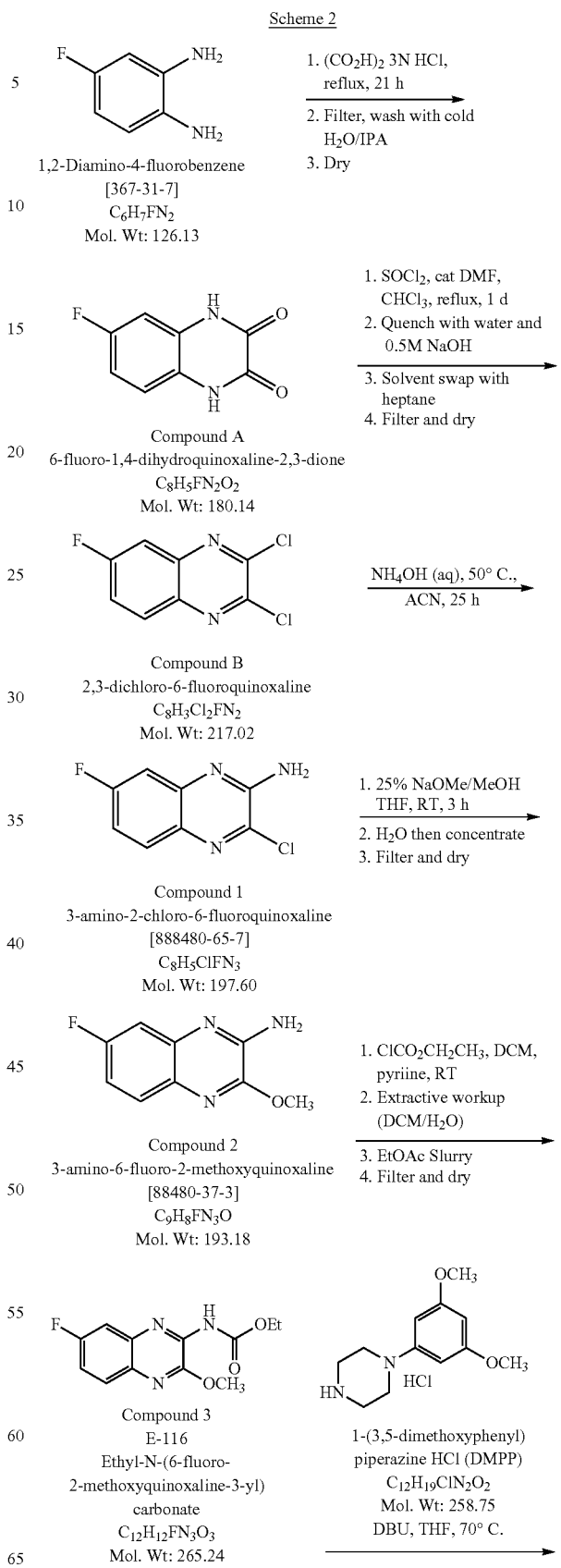

Scheme 2

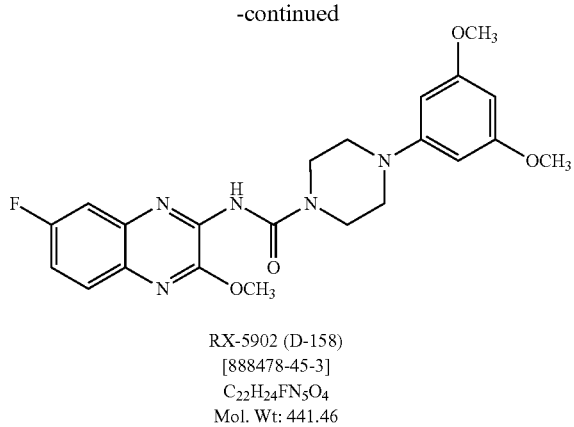

RX-5902 (D-158)
[888478-45-3]
$C_{22}H_{24}FN_5O_4$
Mol. Wt: 441.46

In particular, the present invention of the process improvements removed the concentrate to dryness operations in Steps 2, 4 and 5 (for the production of Compound B, Compound 2 and Compound 3, respectively) and improved the volume efficiency in the purification of Compound 1. The present invention also replaced the chlorinated solvents in Steps 2, 4, and 5 with non-chlorinated solvents.

As detailed below, the procedures to avoid concentrating to dryness were successful.

For Step 2, most of the chloroform was distilled away and then replaced with heptane which provided a filterable suspension of Compound B.

For Step 3, the purification of Compound 1 was also improved. Specifically, the purification was accomplished by filtering the reaction mixture warm (45±5° C.), which resulted in an improved yield of 72.6% in comparison to a yield of 62% using the small batch procedure. Furthermore, the undesired regioisomer was surprisingly reduced to acceptable levels. (See Table 1.)

TABLE 1

Level of Regioisomer Impurity Levels in Various Batches of RX-5902

| Batch | Compound 1 Regioisomer | Compound 2 Regioisomer | Compound 3 Regioisomer | RX-5092 Regioisomer (7-F) |
|---|---|---|---|---|
| 35444A† | 0.9% | 0.7% | NT* | 0.6% |
| 35686A† | 0.7% | 0.35% | NT* | 0.3% |
| 35921A† | 1.83% | ND** | ND** | 0.08% |

†Batches 35444A and 35686A were made by the prior small batch process as described below in Example 13, and Batch 35921A was prepared by the improved fixed reactor/large scale process as described below in Example 14.
NT*—Not Tested
ND**—Not Detected For Step 4, two improvements were realized in making Compound 2. First, the removal of the concentrate to dryness step was accomplished by quenching the reaction into water and then distilling off the tetrahydrofuran followed by filtering of the product. This new work up also reduced halogenated solvents. The work up avoided the use of dichloromethane in product extraction.

For Step 5, the concentration to dryness step was removed by atmospheric distillation of dichloromethane and replacing it with ethyl acetate in situ. The solvent swap provided another easily filterable slurry to isolate the desired product in high purity and better yield.

4.10 Nanoformulations of RX-5902

The present invention provides new nanoformulations of RX-5902 having improved oral bioavailability and methods of making nanoformulations of RX-5902. For example, the present invention provides a method for reducing the particle size of the compound of formula (I), or pharmaceutically acceptable salt thereof, under conditions sufficient to provide a suspension. In embodiments, the suspension may be made by a milling process. In embodiments, the milling process can be a low-energy milling process, for example, roller milling. In embodiments, the milling process can be a high-energy milling process, for example, high-energy agitator milling. In embodiments, the milling process may be high-energy agitator milling or roller milling. In embodiments, the milling process may be high-energy agitator milling. In embodiments, the suspension may have a D50 particle size of about 200 nm or less. In embodiments, the method may include lyophilization of the suspension to form a powder. In embodiments, the method may include spray drying the suspension to form a powder.

4.10.1 Reprocessing of RX-5902 Nanosuspension by Low-Energy Milling and Lyophilization Reprocessing of RX-5902 nanosuspension from previous preparations can be used to produce a nanosuspension of RX-5902 for non-GLP use. Prior to processing, the nanosuspension was analyzed to determine if extended storage had adversely affected either the chemical or the physical properties of the Active Pharmaceutical Ingredient (API), in this case, RX-5902, particles. The suspension was processed by roller milling to reduce observed agglomeration to a more acceptable particle-size distribution and then lyophilized to produce a dry powder.

Reprocessing the aged suspension successfully produces a dry powder with a particle-size distribution comparable to that of a clinical bath, which had been milled from unprocessed API and immediately lyophilized. Previously manufactured batches were able to be milled to more uniform particle-size distributions without agglomeration, which indicated that the age of the reprocessed nanosuspension might adversely affect the milling efficiency. For example, the milled material that had been used to make a clinical batch had been reduced to a monomodal, submicron distribution with a D90 of about 200 nm; whereas, the D90 of the reprocessed material had a lower limit of ~800 nm.

Lyophilization conditions appear to play a role in the final particle-size distribution of the dry powder as well. Research and development batches that had been dried using a lyophilizer with a −0.80° C. condenser resulted in more favorable particle-size distributions than did either the clinical batch or the reprocessed batch. Both were dried with a condenser of −53° C. The latter two batches were also made in larger quantities than was the research material, which may indicate that freezing time is also relevant to the formation of aggregates in the dry powder formulation.

4.10.2 RX-5902 High-Energy Nanomilling Process Development and Spray Drying Feasibility Alternative techniques were tested in both the milling and drying of RX-5902 nanosuspension to enhance the efficiency and scalability of the production of the final dried powder. Previously prepared nanosuspension can alternatively be reprocessed by high-energy milling and dried using lyophilization or spray-drying. High-energy agitator milling can be used instead of roller milling to prepare the starting nanosuspension. Spray drying can be used instead of lyophilization to prepare the dry powder. Agitator milling produces a similar nanoparticle size distribution with only minor adjustment to the suspension formulation. No apparent API degradation was observed. Spray drying produced a narrow particle-size distribution in the micron-size range, but does not appear to affect the API nanoparticle either physically or chemically.

RX-5902 appears to be amendable to both agitator milling and lyophilization or spray drying with no appreciable degradation or loss attributable to either process. The only major change needed to transition the nanosuspension preparation to agitator milling was the dilution of the starting preparation. This is not expected to have any deleterious effect on dry powder production because the concentration of the API in the diluted agitator-milled material is greater than that of the final concentration obtained from the original roller milling process. Further dilution should be allowable if necessary to affect efficient extraction of the API from the media.

The original dry powder formulation had been developed using 10% RX-5902 that had been modified by the addition of poloxamer to provide protection against aggregation during the freeze drying. Using spray drying to product the final powder allows for the omission of the dilution, assay, and poloxamer-addition steps of the process. While the particle-size distribution of the spray-dried powder was significantly larger than that of the lyophilized material, the measurement reflected the size of the microspheres and not of the nanocrystals, which appear to be unaffected by the process.

4.10.3 Alternative RX-5902 Nanoformulations and Processes

Extended milling times caused foaming during the 1.5 kg manufacture of RX-5902 nanoformulation. The foaming was mitigated by intermittent refrigeration of the sub-batches during production. The extended milling times and intermittent refrigeration produced the same quality of RX-5902 nanoformulation as produced in smaller-scale batches.

4.10.4 Milling Operations for RX-5902

As particle size reduction is a key parameter for bioavailability of RX-5902, various methods of reducing particle size can be utilized and optimized. These methods include Mirconization, Mechanical Milling, Cryogenic Milling, Wet Milling methods (Agitator and Rolling Mills), Microfluidization, and, High Pressure Homogenization. Wet-milling methods can be followed by either a lyophilization or spray drying method to provide solid form.

An amorphous formulation prepared by methods including Holt Melt Extrusions, Spray Dried Dispersions with an excipient present and Spray Congealing can also be used. All these methods can form an amorphous form that is anticipated to possess improved bioavailability.

A lipid formulation of RX-5902 can also be utilized. The lipid formulation may benefit RX-5902 providing a pre-solubilized or pre-suspended API in an oil phase. A lipid based formulation would also be expected to have improved bioavailability.

4.11 RX-5902. Crystal Structure 4.11.1 XRPD Study of RX-5902 Crystals

An X-Ray Powder Diffraction (XRPD) analysis of RX-5902 crystals provided the major peaks are shown in Table 2. A complete listing of peaks and other parameters is provided in the working examples.

TABLE 2

Major peaks in XRPD of RX-5902

| Pos. [°2Th.] | d-spacing [Å] | Rel. Int. [%] |
| --- | --- | --- |
| 8.558004 | 10.33244 | 92.11 |
| 14.346660 | 6.17385 | 38.83 |
| 15.328680 | 5.78046 | 33.92 |
| 15.574780 | 5.68967 | 79.32 |
| 15.850830 | 5.59121 | 62.55 |
| 16.970760 | 5.22467 | 44.44 |
| 18.141790 | 4.88998 | 67.28 |
| 21.479630 | 4.13705 | 69.54 |
| 21.837050 | 4.07014 | 31.41 |
| 23.658390 | 3.76076 | 66.17 |
| 24.417090 | 3.64560 | 33.76 |
| 24.852430 | 3.58272 | 100.00 |
| 27.474790 | 3.24643 | 93.49 |

As shown above, the crystalline form of RX-5902 (designated Form 1) has characteristic peaks (degrees 2Theta) is characterized by peaks at 8.56, 15.57, 15.85, 18.14, 21.48, 23.66, 24.85, and 27.47. Form 1 RX-5902 can be further characterized by peaks (degrees 2Theta) at 8.56, 14.35, 15.33, 15.57, 15.85, 16.97, 18.14, 21.48, 21.83, 23.66, 24.41, 24.85, and 27.47. The XRPD of Form 1 RX-5902 is also characterized by a trace having d-spacing (Å) of 10.33, 5.69, 5.59, 4.89, 4.14, 3.76, 3.58, and 3.25. The XRPD of Form 1 RX-5902 is further characterized by a trace having d-spacing (A) of 10.33, 6.17, 5.78, 5.69, 5.59, 5.22, 4.89, 4.14, 4.07, 3.76, 3.65, 3.58, and 3.25.

4.11.2 Polymorph Study

A batch of RX-5902 was characterized by various solid state techniques. The supplied material was a crystalline solid, denoted as Form 1. This material is non-hygroscopic, stable to exposure to humidity and represents a viable form for further development. XRPD analysis of a formulation containing RX-5902 showed peaks consistent with Form 1, suggesting that no form change had occurred during the formulation process.

Polymorph screening experiments performed using crystalline and amorphous RX-5902 identified multiple crystalline forms of the API. Many of these were poorly crystalline in nature and difficult to reproduce for full evaluation. XRPD diffractograms of several of these forms show similarities, suggesting them to be structurally related, whilst the varying amounts of solvent present raise the possibility that these are channel solvate type structures.

The difficulties encountered in re-preparing various observed solids meant that it was not possible to gain a full understanding of the polymorphic landscape of RX-5902. The propensity of the API to crystallize in differing forms means that a rigorous crystallization protocol will be required in order to ensure reliable preparation of Form 1. Studies aimed at identifying suitable solvents for such a procedure suggested diethyl ether, 2-methyl-1-propanol, ethanol and MIBK as good candidates.

5. EXAMPLES

The following examples are presented for illustrative purposes and should not serve to limit the scope of the disclosed subject matter.

Example 1: In Vitro Metabolism Studies on RX-5902

Two in vitro studies were performed to examine the involvement of specific cytochrome P450 (CYP450) isozymes in the in vitro metabolism of RX-5902. In the first study, the loss of RX-5902 was measured after incubation with expressed CYP450 isozymes (1A2, 2A6, 2B6, 2C8, 2C9, 2C19, 2D6, 3A4 and 3A5). The results indicate loss of RX-5902 after 30-minute incubations with CYPs 3A4 (87% loss) and 3A5 (54% loss), but little loss with any other CYP isozyme. In the second study, RX-5902 was incubated with pooled human liver microsomes in the presence of CYP450 isozyme-selective chemical inhibitors. The inhibitors tested were selective for 1A2, 2A6, 2B6, 2C8, 2C9, 2C19, 2D6, and 3A4/5. Marked inhibition of RX-5902 metabolism was observed in the presence of a CYP3A4/5-selective inhibitor (ketoconazole), but no significant inhibition was observed with inhibitors of the other isozymes. Together, these studies suggest that the CYP450-mediated metabolism of RX-5902 is primarily due to the CYP3A4/5 isozymes, with little metabolism via other CYP450 isozymes.

The data indicate that RX-5902 metabolism and exposure may be particularly sensitive to drug-drug interactions with drugs that alter CYP3A4/5 activity. Thus, co-administration of RX-5902 with CYP3A4/5 inhibitors may increase plasma concentrations of RX-5902, while co-administration with CYP3A4/5 inducers may reduce plasma concentrations of RX-5902. Thus, there is the potential that subjects receiving CYP3A4/3A5 inhibitors may have exaggerated pharmacological or toxic responses to RX-5902 or that those receiving CYP3A4 inducers may have reduced RX-5902 activity.

Example 2: Pharmacokinetics, Safety and Tolerability of RX-5902 in Humans

In a dose-ranging study, the pharmacokinetics (PK), safety and tolerability of RX-5902 at various oral doses were evaluated. Subjects with advanced or metastatic solid tumors were administered capsules containing RX-5902 at daily doses of 25-775 mg once weekly, 250-300 mg three times a week, 150-300 mg five times a week, or 300-350 mg seven times a week of RX-5902 for up to 6 dosing cycles. Each cycle consisting of 1-5 doses of RX-5902 per week for 3 weeks followed by 1 week of rest, or 5-7 doses of RX-5902 per week for 4 weeks without any rest per 4-week cycle. All but one subject had fasted from food for at least 8 hours before administration. One subject received 300 mg RX-5902 in fed state. Plasma concentrations were measured on Days 1 and 15, for 48 hrs, using a validated LC-MS/MS assay, and noncompartmental pharmacokinetic parameters were calculated using Phoenix WinNonlin, Version 6.4.

Pharmacokinetics (PK)

Preliminary PK data after a single administration is presented in FIG. 1 (for Subjects #1-11) and Table 3.

TABLE 3

Human PK Data

| Dose mg | Subject # | Frequency Per week | Day | Food | $C_{max}$ ng/mL | $T_{max}$ hr | $T_{1/2}$ Hr | $AUC_{0-24}$ hr*ng/mL | $AUC_{0-48}$ hr*ng/mL |
|---|---|---|---|---|---|---|---|---|---|
| 25 | 1 | 1 | 1 | Fasted | 99.1 | 6 | 5.8 | 830 | 894 |
| 50 | 2 | 1 | 1 | Fasted | 109 | 1.5 | 13.2 | 1027 | 1308 |
| 100 | 3 | 1 | 1 | Fasted | 252 | 2 | 27.6 | 1783 | 2341 |
| 150 | 4 | 1 | 1 | Fasted | 226 | 6 | 11.5 | 2689 | 3280 |
| 225 | 5 | 1 | 1 | Fasted | 364 | 4 | 12.0 | 3425 | 4312 |
| 300 | 6 | 1 | 1 | Fasted | 318 | 6 | 14.6 | 4679 | 6141 |
| 300 | 7 | 1 | 1 | Fasted | 452 | 1.5 | 15.6 | 4170 | 5552 |
| 425 | 8 | 1 | 1 | Fasted | 660 | 2 | — | 9321 | 14673 |
| 575 | 9 | 1 | 1 | Fasted | 707 | 4 | — | 6825 | 10098 |
| 775 | 10 | 1 | 1 | Fasted | 487 | 1.5 | — | 3541 | 5012 |
| 775 | 11 | 1 | 1 | Fasted | 654 | 4 | 9.7 | 6925 | 8126 |
| 300 | 12 | 1 | 1 | Fed | 779 | 4 | 11.9 | 8615 | 10749 |
| 250 | 13 | 3 | 1 | Fasted | 394 | 2 | 14.0 | 3975 | 5211 |
| 250 | 13 | 3 | 15 | Fasted | 403 | 2 | — | 4812 | 7774 |
| 300 | 14 | 3 | 1 | Fasted | 288 | 6 | 10.3 | 3848 | 4555 |
| 300 | 14 | 3 | 15 | Fasted | 301 | 2 | — | 3049 | 4143 |
| 150 | 15 | 5 | 1 | Fasted | 227 | 2 | — | 2152 | — |
| 150 | 15 | 5 | 15 | Fasted | 347 | 1 | — | 3721 | — |
| 200 | 16 | 5 | 1 | Fasted | 337 | 4 | 8.5 | 2752 | — |
| 200 | 16 | 5 | 15 | Fasted | 440 | 2 | — | 4034 | — |
| 300 | 17 | 5 | 1 | Fasted | 317 | 2 | — | 3798 | — |
| 300 | 17 | 5 | 15 | Fasted | 460 | 1.5 | — | 3840 | — |
| 300 | 18 | 5 | 1 | Fasted | 549 | 1.5 | — | 4607 | — |
| 300 | 18 | 5 | 15 | Fasted | 536 | 1 | — | 4878 | — |
| 300 | 19 | 5 | 1 | Fasted | 419 | 4 | — | 3855 | — |
| 300 | 19 | 5 | 15 | Fasted | 190 | 2 | — | — | — |
| 300 | 20 | 5 | 1 | Fasted | 624 | 2 | | | |
| 300 | 21 | 7 | 1 | Fasted | 713 | 4 | — | — | — |
| 300 | 21 | 7 | 15 | Fasted | 1250 | 6 | — | — | — |
| 300 | 22 | 7 | 1 | Fasted | 374 | 2 | — | 2986 | 3178 |
| 300 | 23 | 7 | 1 | Faasted | 276 | 4 | — | — | — |
| 300 | 24 | 7 | 1 | Fasted | 391 | 1.5 | — | — | — |
| 350 | 25 | 7 | 1 | Fasted | 750 | 1.5 | — | 4819 | 4957 |

Compared to the subject dosed with 300 mg in the fasted state, significantly higher exposure was observed in the subject dosed with 300 mg in a fed state (Table 3).

RX-5902 sometimes displayed an apparent, short lag time (0.25 hour), usually followed by a steep, rising plasma phase. $T_{max}$ was somewhat variable, being observed from 1 to 6 hours after dosing. After $T_{max}$, a short distribution phase was often observed, followed by the apparent terminal phase. Usually, over 75% of $AUC_{0-t}$ (0-48 hours) was observed by 24 hours. Apparent terminal $T_{1/2}$ ranged from 5.8 to 27.6 hours, but most individual values were near the mean value of 13.0 hours. $C_{max}$ and $AUC_{0-t}$ (0-48 hours) increased fairly linearly with dose. $AUC_{last}$ increased in a dose-proportional manner overall, but $C_{max}$ increased in a less than proportional manner. Clinical $C_{max}$ and AUC ranges for various doses and dose frequencies are shown in Table 3.

Safety and Tolerability

The most frequently reported adverse events were mild nausea, vomiting and fatigue. The results show that at the tested dose levels, RX-5902 is well tolerated.

Example 3: Protocol for Evaluating Efficacy of RX-5902 in Xenograft Models of Cancer The efficacy of RX-5902 in human cancer xenograft mouse models is examined. Female nude mice (nu/nu, Harlan or CRL: NU(NCr)-Foxn1$^{nu}$, Charles River), 9-10 weeks old, with a body weight (BW) range of 15-30 g on day 1 of the study, are fed ad libitum water (reverse osmosis, 1 ppm C1), and NIH 31 Modified and Irradiated Lab Diet® consisting of 18.0% crude protein, 5.0% crude fat, and 5.0% crude fiber. The mice are housed on irradiated Enrich-o'Cobs™ Laboratory Animal Bedding in static microisolators on a 12-hour light cycle at 20-22° C. (68-72° F.) and 40-60% humidity. The study complies with the recommendations of the Guide for, Care and Use of Laboratory Animals with respect to restraint, husbandry, surgical procedures, feed and fluid regulation, and veterinary care.

Various human tumor cell lines (e.g., HCT116, HT29, H460, H69, Caki-1, CaSki, MiaPaca2, BxPC3 and Colo 205 cells [ATCC, Manassas, Va., USA]) are cultured according to ATCC's instruction. The tumor cells are cultured in tissue culture flasks in a humidified incubator at 37° C., in an atmosphere of 5% $CO_2$ and 95% air.

The cells are harvested during exponential growth and re-suspended with phosphate buffered saline. Each test animal receives a subcutaneous (s.c.) injection of 5×10$^6$ tumor cells into the right flank and tumor growth is monitored as the average tumor size approaches the target range of 80-300 mm$^3$. When tumors reach the target size mice are randomized into several groups (n=10-20) and treatment with various regimens of RX-5902 or a positive (e.g., gemcitabine) or negative control (e.g.; vehicle, saline) is initiated. Tumors and body weights are measured regularly until the study is terminated.

Tumors are measured in two dimensions using calipers, and volume is calculated using the formula:

$$\text{Tumor Volume (mm}^3\text{)} = \frac{w^2 \times l}{2}$$

where w=width and l=length, in mm, of the tumor. Tumor weight may be estimated with the assumption that 1 mg is equivalent to 1 mm$^3$ of tumor volume.

Treatment begins on Day 1 in eight groups of mice (n=10-20/group) with established subcutaneous tumors of a particular cell line. Each group is treated according to the study design. All doses are adjusted per body weight. Animals in each group are divided for efficacy and sampling purposes. There are also groups designated to vehicle control and no treatment for sampling purposes.

On Day 1 of the study, all animals from no-treatment group are sampled for tumor and whole blood. Additionally, four animals from other groups are sampled 2, 8 and 24 hours post first dose and 24 hours post second dose. Mice are sacrificed by terminal cardiac puncture under isofluorane anesthesia. Full blood volume is collected into a tube containing lithium heparin anticoagulant. Each blood sample is processed individually for plasma using lithium heparin as anticoagulant for PBMC. The tumors are collected and divided in halves where one part is fixed for 24 hours in 10% neutral buffered formalin (NBF), and then transferred to 70% ethanol and the other half is snap frozen. The plasma and tumor frozen samples are stored at −80° C.

Treatment efficacy is determined using data from Day 15. The MTV (n), the median tumor volume for the number of animals, n, on Day 15, is determined for each group. Percent tumor growth inhibition (% TGI) is defined as the difference between the MTV of the designated control group (vehicle administration) and the MTV of the drug-treated group, expressed as a percentage of the MTV of the control group:

% TGI=[1−(MTV$_{drug\ treated}$/MTV$_{control}$)]×100

The data set for TGI analysis includes all animals in a group, except those that die due to treatment-related (TR) or non-treatment-related (NTR) causes. An agent that produces at least 60% TGI in this assay is considered to be potentially therapeutically active.

Animals are monitored individually for tumor growth until Day 71. The study protocol specifies a tumor growth delay assay based on the median time to endpoint (TTE) in a treated group versus the control group. Each animal is euthanized for tumor progression (TP) when its tumor reaches the 2000 mm$^3$ volume endpoint. The time to endpoint (TTE) for each mouse is calculated with the following equation:

$$TTE = \frac{\log_{10}\ (\text{endpoint volume}) - b}{m}$$

where b is the intercept and m is the slope of the line obtained by linear regression of a log-transformed tumor growth data set. The data set is comprised of the first observation that exceeds the study endpoint volume and the three consecutive observations that immediately precede the attainment of the endpoint volume. Any animal that does not reach endpoint is euthanized at the end of the study and assigned a TTE value equal to the last day of the study (71 days). In instances in which the log-transformed calculated TTE precedes the day prior to reaching endpoint or exceeds the day of reaching tumor volume endpoint, a linear interpolation is performed to approximate TTE. Any animal determined to have died from treatment-related (TR) causes is assigned a TTE value equal to the day of death. Any animal that dies from non-treatment-related (NTR) causes is excluded from TTE analysis.

On Day 71, MTV (n) is defined as the median tumor volume of the number of animals, n, that survives to the last day and whose tumors has not reached the volume endpoint. Any animal determined to have died from treatment-related (TR) causes is to be assigned a TTE value equal to the day of death. Any animal that dies from nontreatment-related (NTR) causes is to be excluded from the analysis. Treatment outcome is evaluated from tumor growth delay (TGD), which is defined as the increase in the median TTE for a treatment group compared to the control group:

TGD=T−C expressed in days, or as a percentage of the median TTE of the control group:

$$\%\ TGD = \frac{T-C}{C} \times 100$$

where T=median TTE for a treatment group, and C=median TTE for the control group.

Treatment efficacy is also determined from the number of regression responses. Treatment may cause partial regression (PR) or complete regression (CR) of the tumor in an animal. In a PR response, the tumor volume is 50% or less of its D1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. Any animal with a CR response on the last day of the study is additionally classified as a tumor-free-survivor.

For toxicity assessments, animals are weighed daily for the first five days of the study and twice weekly thereafter. The mice are observed frequently for overt signs of any adverse, treatment-related side effects, and clinical signs of toxicity are recorded when observed.

Acceptable toxicity is defined as a group mean bodyweight loss of less than 20% during the study and not more than one treatment-related (TR) death among ten treated animals. Any dosing regimen resulting in greater toxicity is considered above the maximum tolerated dose (MTD). A death is classified as TR if attributable to treatment side effects as evidenced by clinical signs and/or necropsy, or if due to unknown causes during the dosing period or within fourteen days of the last dose. A death is classified as non-treatment-related (NTR) if there is no evidence that death was related to treatment side effects.

Prism 6.05 (GraphPad) for Windows is employed for statistical and graphical analyses. MTV values for multiple groups are compared with the non-parametric Kruskal-Wallis test and a post hoc Dunn's multiple comparison test. The two-tailed statistical analyses are conducted at P=0.05. Prism reports results as non-significant (ns) at P>0.05, significant (symbolized by "*") at 0.01<P≤0.05, very significant ("") at 0.001<P<0.01 and extremely significant ("*") at P≤0.001. Because statistical tests are tests of significance and do not provide an estimate of the size of the difference between groups, all levels of significance are described as either significant or non-significant within the text of this report.

Survival is analyzed by the Kaplan-Meier method, based on TTE values. The log rank (Mantel-Cox) and Gehan-Breslow-Wilcoxon tests determine the significance of the difference between the overall survival experiences (survival curves) of two groups, based on TTE values. The Kaplan-Meier plot and statistical tests share the same data sets, and exclude any animals that are recorded as NTR deaths. A scatter plot is constructed to show TTE values for individual mice, by group; this plot shows NTR deaths, which are excluded from all other figures. Group mean tumor volumes are plotted as functions of time. When an animal exits the study because of tumor size or TR death, its final recorded tumor volume is included with the data used to calculate the median volume at subsequent time points. Tumor growth curves are truncated after two TR deaths occur in the same group. Group mean Body Weight (BW) changes over the course of the study are graphed as percent change, ±SEM, from D1. Tumor growth and BW change curves are truncated after more than half the assessable mice in a group exits the study.

Example 4: Efficacy of RX-5902 in Renal Cell Carcinoma Xenograft Model

Figure 2:
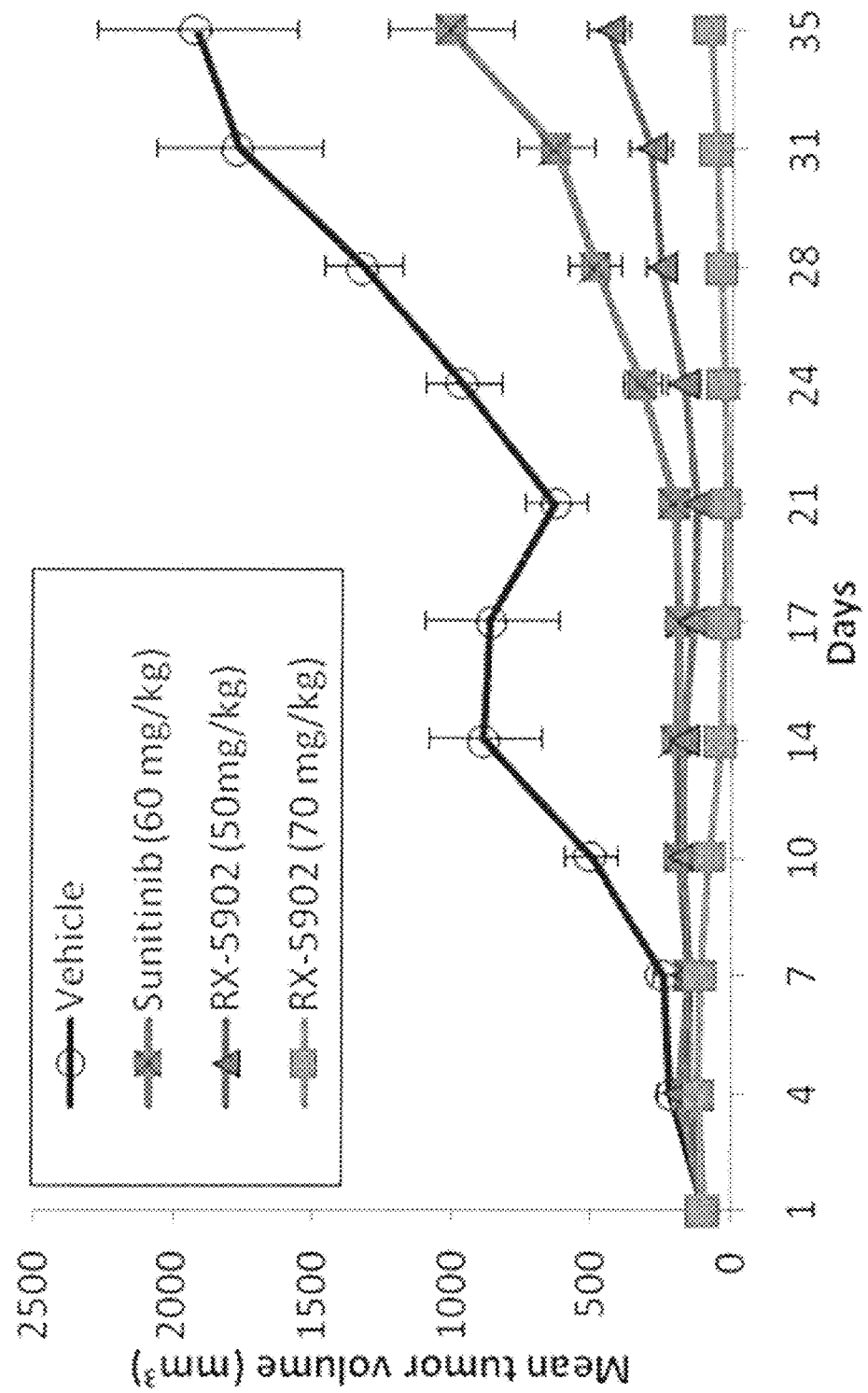
FIG. 2 is graph showing the mean tumor volume in mice with human renal tumor (Caki-1) xenografts following oral administration of RX-5902 at 50 mg/kg and 70 mg/kg 5 days a week.
Figure 3:
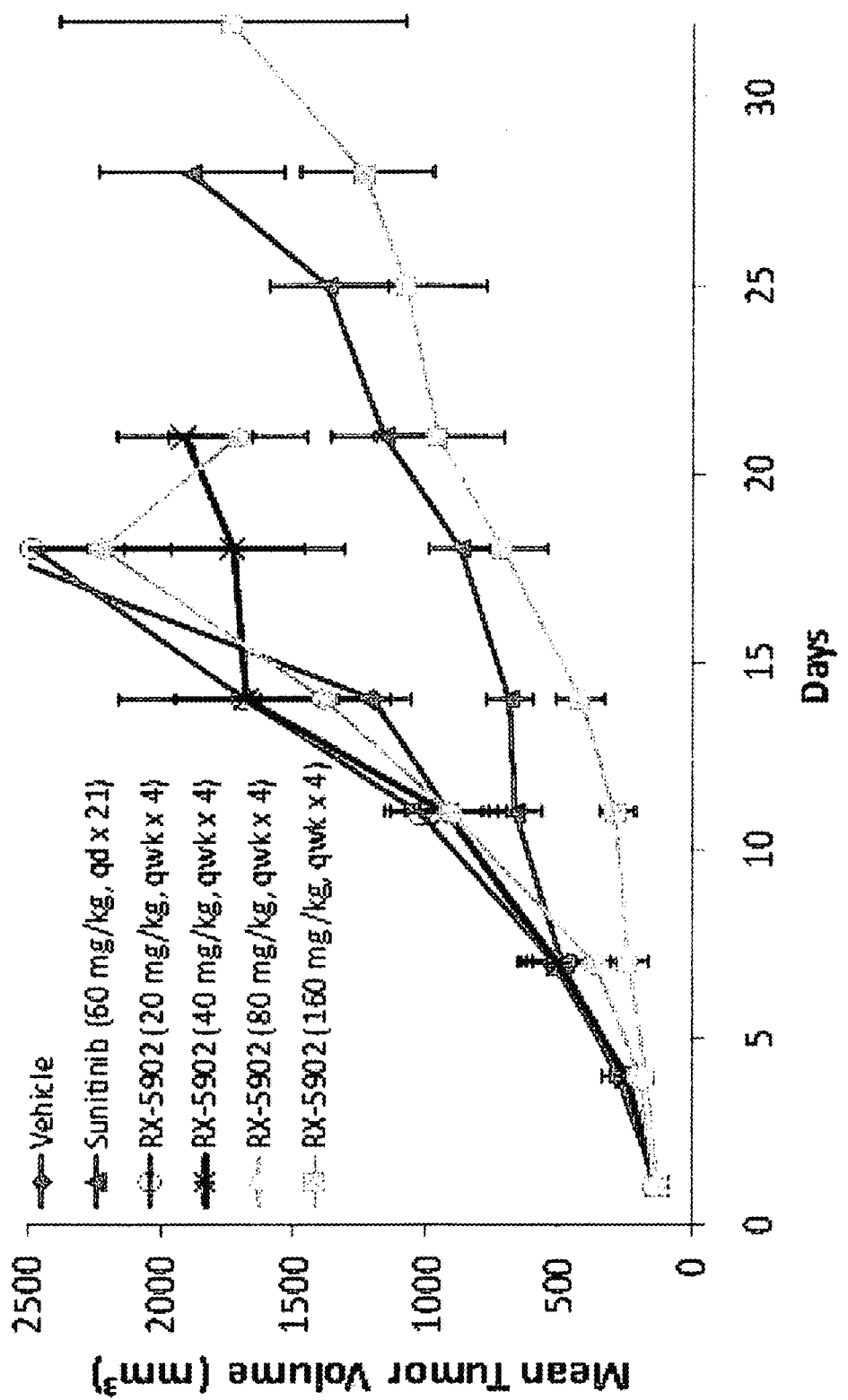
FIG. 3 is a graph showing the mean tumor volume in mice with human renal tumor (Caki-1) xenografts following oral administration of Sunitinib daily at 60 mg/kg for 21 days and RX-5902 at 20, 40, 80 and 160 mg/kg once a week for four weeks.

Following the protocol described in Example 3, the effect of RX-5902 on tumor growth in mice with human renal tumor xenografts (Caki-1) was examined. Tumor growth delay was measured as the increase in median time to the endpoint tumor volume in a treated group compared to a vehicle treated group. Efficacy of RX-5902 was determined using two different dosing schemas: weekly dosing at 20-160 mg/kg for 4 weeks (FIG. 3), or 50-70 mg/kg daily (5 days on/2 days off) for 3 weeks (FIG. 2). Weekly dosing of RX-5902 at 160 mg/kg resulted in a 75% TGD (P<0.001) (FIG. 3). Daily administration of RX-5902 resulted in dose-dependent TGI (80 and 96%; Day 21) and TGD (68 and 104%, P<0.001) (FIG. 2), and extended the overall survival of the animals at both doses (P<0.0001) (data not shown). At the dose of 70 mg/kg daily, 6/10 animals demonstrated partial tumor regressions and 1/10 a complete tumor regressions. RX-5902 did not result in a reduction in body weight gain, treatment related deaths, or clinical observations in either of the dosing schemas. Sunitinib (positive control in this study; 60 mg/kg; daily for 21 days) resulted in TGD for both in vivo studies validating the Caki-1 model herein. These data support the potential therapeutic activity of RX-5902 in renal cell cancers and extending survival. The results also suggest that more frequent dosing, with lower daily doses, in humans may be a more effective administration schedule for RX-5902 in renal cancer.

Results of Xenograft studies (described in Examples 4-9) are summarized in Table 4.

TABLE 4

Anti-tumor Activity of Orally Administered RX-5902 in Mice

| Dose | | Xenograft (TGI %* or TGD^) | | | | | | |
|---|---|---|---|---|---|---|---|---|
| (mg/kg) | Schedule | Caki-1 | MiaPaca-2 | Colo205 | MDA-MB-231 | A2780 | SK-OV3 | A549 |
| 160 | QWK | 75%^ | | 0%* | 44%*; 39%* | 43%* | | 30%* |
| 320 | QWK | | | 13%* | 65%*; 82%* | 43%* | | 26%* |
| 600 | QWK | | | 33%* | 83%*; 165%* | 75%* | | 26%* |
| 40 | 5ON/2OFF | | | | | | 6%^ | |
| 50 | 5ON/2OFF | 68%^ | 83%^ | | | | | |
| 60 | 5ON/2OFF | | | | | | | |
| 70 | 5ON/2OFF | 104%^ | 339%^ | | | | 49%^ | |

^denotes TGD %;
*denotes TGI %.
In some instances both values are reported.

Example 5: Efficacy of RX-5902 in Pancreatic Cancer Xenograft Model

Following the protocol described in Example 3, the effect of RX-5902 on tumor growth in mice with human pancreas tumor xenografts (MiaPaca-2) was examined. Tumor growth was measured in a treated group compared to a vehicle treated group. The results show marked efficacy with 50 or 70 mg/kg RX-5902 administered 5 days a week (See Table 4), suggesting that daily dosing in humans may be an effective treatment schedule for RX-5902 in pancreatic cancer.

Example 6: Efficacy of RX-5902 in Colorectal Cancer Xenograft Model

Following the protocol described in Example 3, the effect of RX-5902 on tumor growth in mice with human colorectal tumor xenografts (Colo205) was examined. Tumor growth was measured in a treated group compared to a vehicle treated group. The results show marked efficacy with 320 and 600 mg/kg weekly RX-5902 administration (See Table 4), suggesting that RX-5902 may be an effective treatment in colorectal cancer.

Example 7: Efficacy of RX-5902 in Breast Cancer Xenograft Model and Role of Phosphorylated P68

Figure 12:
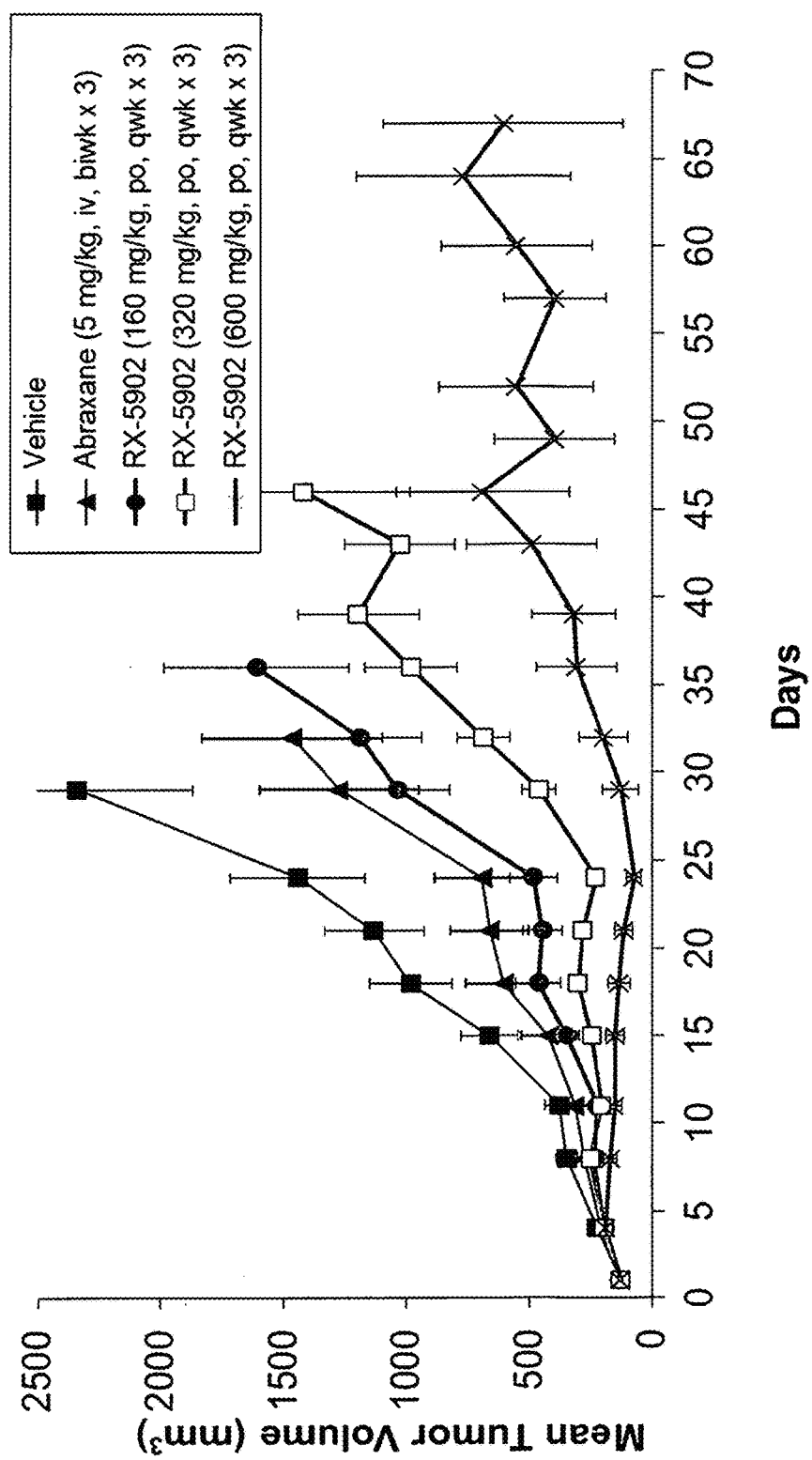
FIG. 12 is graph showing the mean tumor volume in mice with human breast cancer (MDA-MB-231) xenografts following oral administration of RX-5902 at 160 mg/kg, 320 mg/kg, and 600 mg/kg once a week for three weeks, compared to Abraxane® administered intravenously at 5 mg/kg, twice a week for three weeks.
Figure 13:
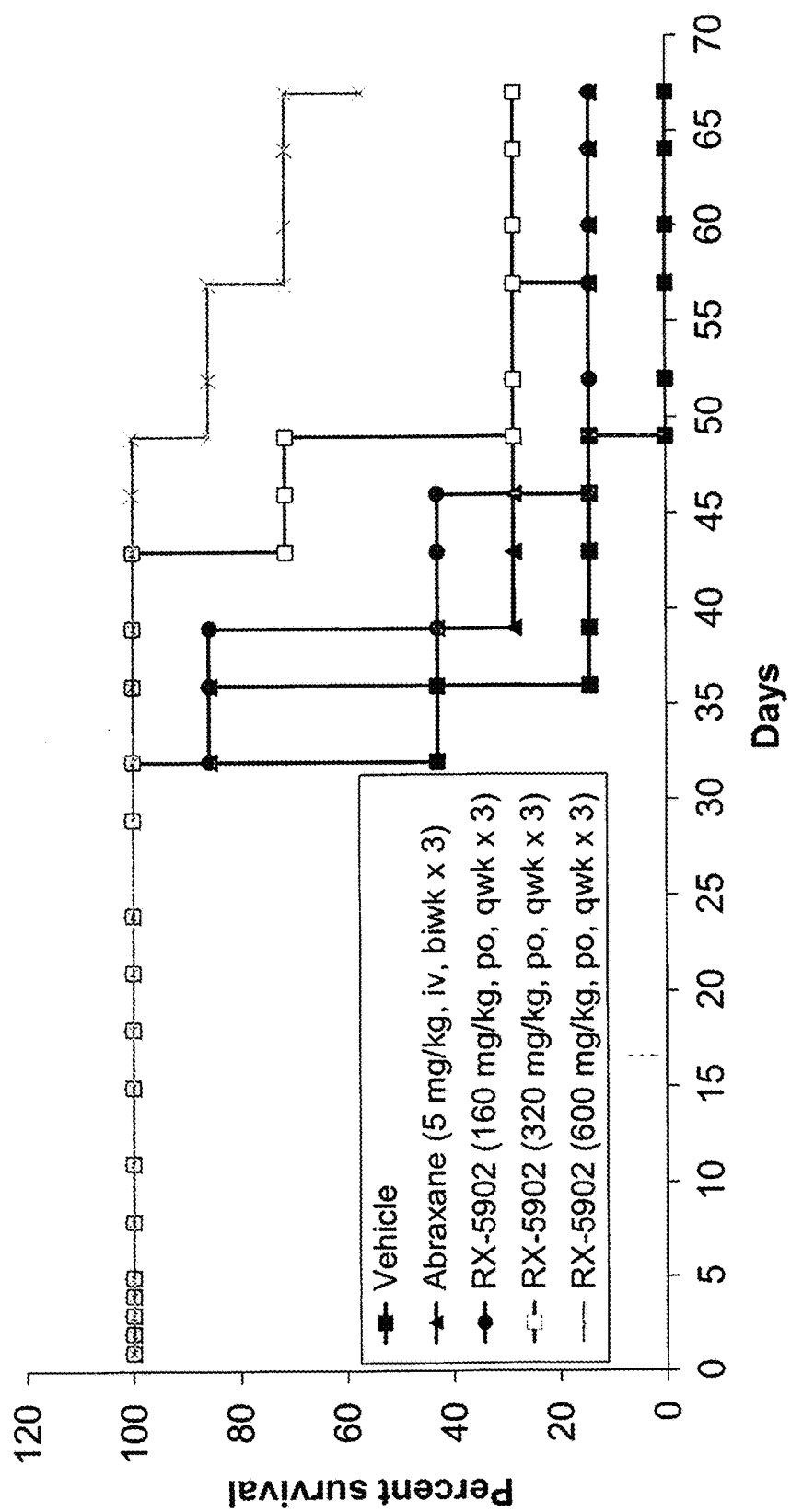
FIG. 13 is graph showing the Kaplan-Meier survival curves in mice with human breast cancer (MDA-MB-231) xenografts following oral administration of RX-5902 at 160 mg/kg, 320 mg/kg, and 600 mg/kg once a week for three weeks, compared to Abraxane® administered intravenously at 5 mg/kg, twice a week for three weeks. These data are from the same study as shown in FIG. 12.

Following the protocol described in Example 3, the effect of RX-5902 on tumor growth in mice with human breast tumor xenografts (MDA-MB-231) was examined. Tumor growth was measured in a treated group compared to a vehicle treated group. The results show marked efficacy with 160, 320, and 600 mg/kg weekly RX-5902 administration (See Table 4; FIG. 12), and extending the survival in treated mice (FIG. 13). These results suggest that RX-5902 may be effective in treating breast cancer and extending survival.

It was also determined whether phosphorylated p68 on Tyr593 played a key role in RX-5902's ability to inhibit cancer cell growth by knocking down p68. p68-siRNA efficiently down-regulated the expression of phosphorylated p68 on Tyr593 as well as p68 in the triple-negative (TN) breast cancer cell line, MDA-MB-231. Exposure of p68-siRNA-transfected cells to the $IC_{50}$ concentration of RX-5902 protected MDA-MB-231 cells from the cytotoxic effects of RX-5902, indicating that phosphorylated p68 on Tyr593 is a key molecule for RX-5902's cytotoxic effects.

Example 8: Efficacy of RX-5902 in Cisplatin-Resistant Ovarian Cancer Xenograft Model Following the protocol described in Example 3, the effect of RX-5902 on tumor growth in mice with human ovarian tumor xenografts (A-2780) was examined. Tumor growth was measured in a treated group compared to a vehicle treated group. The results show marked efficacy with 160, 320, and 600 mg/kg weekly RX-5902 administration (See Table 4). Similar results were obtained in another model of ovarian tumor xenograft (SK-OV3) at 40 and 70 mg/kg RX-5902 given daily (Table 4). These results suggest that RX-5902 may be an effective treatment in human ovarian cancer.

Example 9: Efficacy of RX-5902 in Non-Small Cell Lung Cancer Xenograft Model Following the protocol described in Example 3, the effect of RX-5902 on tumor growth in mice with human non-small cell lung tumor xenografts (A549) was examined. Tumor growth was measured in a treated group compared to a vehicle treated group. The results show efficacy with 160, 320, and 600 mg/kg weekly RX-5902 administration (See Table 4), suggesting that RX-5902 may be an effective treatment in lung cancer.

Example 10: Efficacy of RX-5902 in Syngeneic MC38 Murine Colon Cancer Xenograft Model Following the methods described below, the effect of RX-5902 on tumor growth in a syngeneic model using female C57BL/6 mice with MC38 murine colon cancer was examined. Tumor growth was measured in a treatment group compared to a control (vehicle treated) group (see Table 5 below for dosing schema and treatment regimen). These data demonstrate that the addition of RX-5902 to a programmed death receptor 1 (PD-1) inhibitor, RMP1-14, had an additive effect in the inhibition of tumor growth (90% RX-5902 alone, 93% RMP1-14 alone, versus 99% in combination of two agents [P<0.01 versus control group]. Combination of the two agents also resulted in higher number of mice (6 mice) with partial regression and complete regression with 4 animals showing tumor free survival, compared to 4 animals with partial regression and complete regression in the RMP1-14 alone group with 2 showing tumor free survival. All results were obtained without any adverse effects to the mice in the combination group. This study demonstrates that the combination of RX-5902 and a PD-1 inhibitor result in a significant reduction in tumor growth, resulting in partial and complete responses and tumor free survival in mice, in the absence of any adverse event.

TABLE 5

Drugs and Treatment Schedule:

| | | Regimen 1 | | | | Regimen 2 | | | |
| --- | --- | --- | --- | --- | --- | --- | --- | --- | --- |
| Gr. | N | Agent | mg/kg | Route | Schedule | Agent | mg/kg | Route | Schedule |
| 1# | 10 | Vehicle | — | po | (5/2) x 3 | — | — | — | — |
| 2 | 10 | RX-5902 | 84.34 | po | (5/2) x 3 | — | — | — | — |
| 3 | 10 | anti-PD-1 RMP1-14 | 100* | ip | biwk x 2 | — | — | — | — |
| 4 | 10 | RX-5902 | 84.34 | po | (5/2) x 3 | anti-PD-1 RMP1-14 | 100* | ip | biwk x 2 |

Control Group
*μg/animal

The present study consisted of five groups (n=10 per group) of female C57BL/6 mice bearing subcutaneous MC38 tumors (mean tumor volume range: 66-68 mm3) on Day (D1) of the study, when dosing began. Vehicle was administered orally (p.o.). RX-5902 was administered p.o. at 84.34 mg/kg (70 mg/kg active dose). Anti-PD-1 (RMP1-14) was administered at 100 μg/animal, intraperitoneally (i.p.). Group 1 mice served as controls and received PBS (vehicle) five days on, two days off for three cycles ((5/2)×3). Group 2 received RX-5902 (5/2)×3. Group 3 received anti-PD-1 twice weekly for two weeks (biwk×2). Group 4 received RX-5902 (5/2)×3 and anti-PD-1 biwk×2. The study endpoint was a tumor volume of 1500 mm³ or 45 days, whichever came first. Tumor measurements were taken twice weekly until Day 45 with individual animals exiting the study upon reaching the tumor volume endpoint.

Partial treatment outcome was based on percent tumor growth inhibition (% TGI), defined as the percent difference between Day 28, chosen for the TGI analysis, median tumor volumes (MTVs) of treated and control mice. The results were analyzed and were deemed statistically significant at P≤0.05. A treatment that produced at least 60% TGI was considered to have potential therapeutic activity. Additionally, efficacy was determined from tumor growth delay (TGD), a measure of the increase in the median time to endpoint (TTE) in a treatment, compared to the control group. Response was additionally evaluated based on the number of study survivors, partial regression (PR) and complete regression (CR) responses, and logrank significance of differences in survival. Tolerability of the various treatments was assessed by body weight (BW) measurements and frequent observation for clinical symptoms and treatment-related (TR) side effects.

On Day 28, the median tumor volume for the control Group 1 was 1226 mm³, with an individual tumor range of 14 to 1800 mm³. Seven tumors in the control Group 1 reached the volume endpoint with a median TTE of 29.7 days, establishing a maximum T-C of 15.3 days (52% TGD) in the 45-day study. The control TTE ranged from 26.9 to 45.0 days. The variability of the control group decreased the likelihood of achieving statistical significance. The MTV of the three survivors was 14 mm³ and there were two PRs.

Administration of RX-5902 resulted in a significant 90% TGI (P<0.05, Mann-Whitney). This therapy produced a median TTE of 44.8 days or a non-significant 51% TGD. Five animals remained on D45 with an MTV of 14 mm³ and there were three PRs. Treatment with anti-PD-1 led to a significant 93% TGI (P<0.05, Mann-Whitney). This therapy resulted in in six survivors and an assigned TTE of 45.0 days and the maximum possible 52% TGD. Results were not significant. The MTV on D45 was 14 mm³ and there was one PR and three CRs; two animals with the latter ended the study as tumor-free survivors (TFS).

Combination therapy with RX-5902 and anti-PD-1 resulted in a 99% TGI. This outcome was significant compared to the control group (P<0.01, Mann-Whitney), but did not significantly differed from anti-PD-1 monotherapy. This dual therapy was assigned a median TTE of 45.0 days or the maximum possible 52% TGD. All ten animals survived with an MTV of 14 mm³. There was one PR and five CRs, four of which were TFS. Results were significant when compared to controls (P<0.01, log rank) as well as monotherapy (P<0.05 for both comparisons, log rank).

Example 11: Effect of Rx-5902 on β-Catenin Dependent ATPase Activity of Y593 Phosphorylated P68 and Expression of Genes Regulated by β-Catenin Materials and Methods
Cell Culture and Antibodies
MDA-MB-231, SK-MEL-28, and WI-38 cells were obtained from ATCC (Manassas, Va., USA) and were cultured according to the vendor's instructions. Anti-p68 antibody and antiY593-p68 antibody were purchased from Cell Signaling (Danvers, Mass.) and Abcam (Cambridge, Mass.), respectively. Antibodies against β-actin, cyclin D1, p-c-Jun and c-Myc, were purchased from Santa Cruz (Dallas, Tex.). Anti-phospho-tyrosine antibody and HRP conjugated GAPDH antibody were obtained from Cell Signaling (Danvers, Mass.). Recombinant β-catenin and p68 protein were purchased from Creative Biomart (Shirley, N.Y.) and Origene (Rockville, Md.), respectively.

Recombinant Proteins
Recombinant β-catenin was used without further treatment whereas recombinant p68 protein was either used as p68 or phosphorylated by c-Abl for filter binding assay. Recombinant c-Abl was obtained from Abcam (Cambridge, Mass.).

Drug Treatment
RX-5902 was dissolved in DMSO to prepare a stock solution of 2 mM. The stock solution was stored at -20° C. and diluted with medium to prepare working concentrations.

Identification of RX-5902 Binding Proteins
MDA-MB-231 cells were plated onto 6 well plates and treated with RX-5902 at various concentrations (0, 0.1, 1 and 10 μM) for one hour. Cells were lysed with p-MER buffer containing protease/phosphatase inhibitors on ice. Cell lysates were treated with thermolysin protease (1:1,500 ratio) for 10 min at RT and the reaction was stopped by addition of 0.5 M EDTA solution. The reaction mixtures were separated on a 10% SDS-PAGE visualized by Coomassie staining. After identifying several candidate proteins from mass spectrometry sequencing analysis, the protein which interacted with RX-5902 was confirmed by western blot analysis.

Filter Binding Analyses
Filter binding studies have been previously described elsewhere (Coombs et al., *Proc. Natl. Acad. Sci. USA*, 75:5291-5295 (1978). Briefly, recombinant p68 RNA helicase with/without tyrosine phosphorylation was added to the ³H-labeled RX-5902 (10 Ci/mmol) with PBS. ³H-labeled RX-5902 was synthesized from Quotient Bioresearch (Cardiff, UK). After incubation at room temperature for 30 minutes, the binding mixtures were loaded onto a nitrocellulose membrane. The membrane was washed five times with PBS, and then dried by vacuum. The amounts of RX-5902 bound to p68 with/without phosphorylation of p68 were determined by ³H scintillation counting. The same procedure was done with ³H-labeled RX-5902 alone without addition of p68 RNA helicase and sample p68 RNA helicase alone without addition of the ³H-labeled RX-5902 as background ³H scintillation counting. The binding percentages of p68 to the compound were calculated and plotted against concentrations. The dissociation constant (Kd) was estimated by the concentration at 50% of p68 bound to RX-5902 and calculated by linear regression analysis.

ATPase Assay
ATPase activity was determined by measuring the released inorganic phosphate during ATP hydrolysis using a direct colorimetric assay (Shin et al., *Cancer Res.*, 67:7572-7578 (2007); Yang et. al., *Cell*, 127:139-155 (2006)). A typical ATPase assay was carried out in 50 μl reaction volumes, containing 20 mM Tris-HCl pH 7.5, 200 mM NaCl, 1 mM MgCl$_2$, 5 mM DTT, ~1-2 of appropriate substrate, 4 mM ATP, and 10 μl of helicase. The ATPase reactions were incubated at 37° C. for 30 minutes. After incubation, 1 ml of malachitegreen-molybdenum reagent was added to the reaction mixture, and reactions were further incubated at room temperature for exactly 5 minutes. The absorption (A) at 630 nm was then measured. The concentrations of inorganic phosphate were determined by matching the $A_{630nm}$ in a standard curve of $A_{630nm}$ vs. known phosphate concentrations. The proteins, p68 or phospho-p68, used for this assay were prepared in-house similar to the procedure reported previously (Yang et al., *Protein Expr. Purif.*, 35:327-333 (2004)). The percentage of inhibition by defining the ATPase activity of phospho-p68 without RX-5902 as zero percent inhibition was calculated and $IC_{50}$ of RX-5902 was calculated by non-linear regression analysis using Kaledia Graph software program (Synergy Software, Reading, Pa.).

Western Blotting

Protein mix or cell lysates were separated by SDS-PAGE and transferred to PVDF membrane. The membrane was blocked by blocking buffer (1×TBST containing 5% BSA) at room temperature for 1 hour. After a brief wash, the membrane was incubated with primary antibody in blocking buffer at 4° C. overnight. After incubation in primary antibody, the membrane was washed with 1×TBST three times and subsequently incubated with HRP conjugated secondary antibody in blocking buffer at room temperature for 1 hour. The membrane was again washed three times and visualized by ECL system (Thermo Scientific, Rockford, Ill.).

Results

Figure 4:
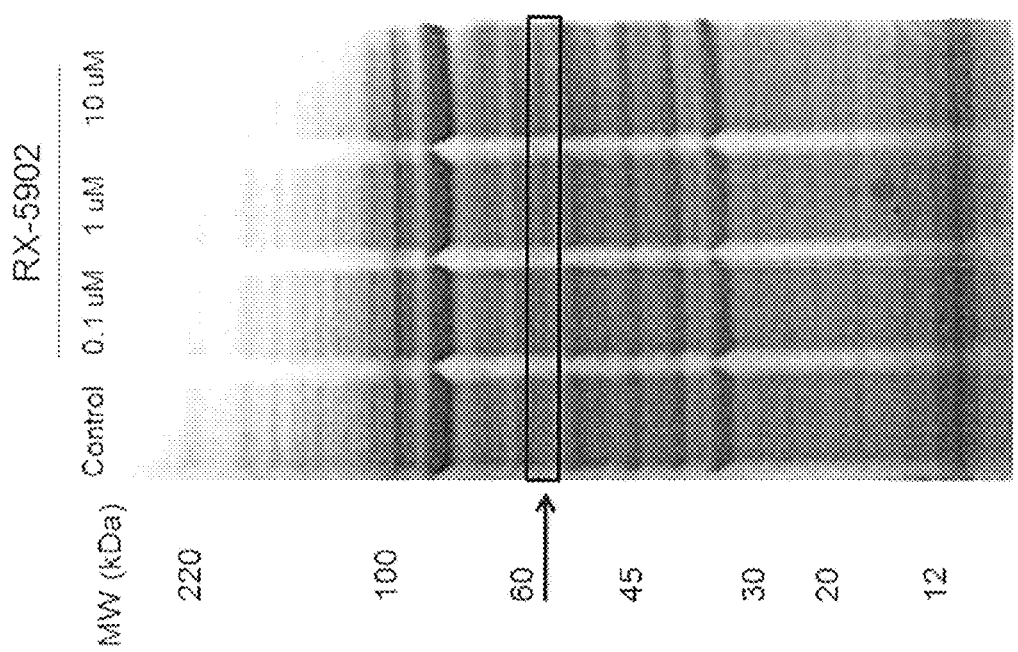
FIG. 4 is a Western blot showing the interaction of RX-5902 with MDA-MB-231 cells, in particular a band with mobility around 60 kDa protected from protease cleavage.
Figure 5:
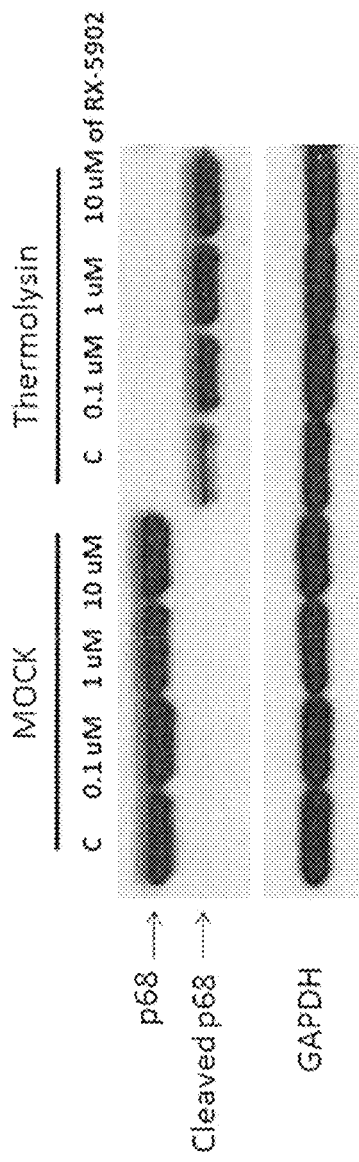
FIG. 5 is a Western blot showing that the protected band of FIG. 4 was recognized by the antibody against p68 RNA helicase.
Figure 6:
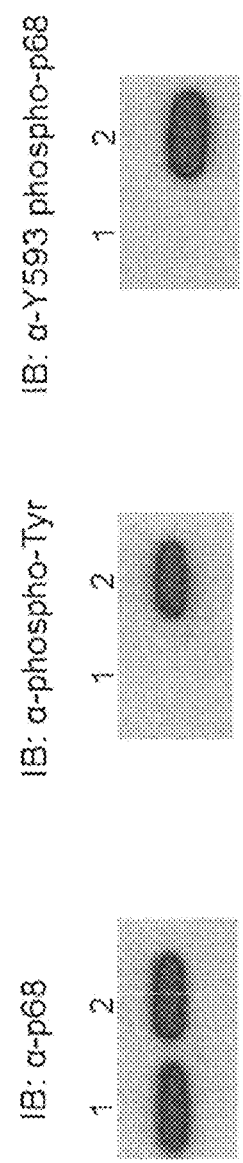
FIG. 6 is a Western blot confirming that p68 was phosphorylated on a tyrosine residue.

Well-established target identification method DARTS assay (Lomenick et al., *Proc. Natl. Acad. Sci. USA*, 106: 21984-21989 (2009)) was used to find target proteins that would interact with RX-5902 in cancer cells. DARTS method indicated that a band with mobility around 60 kDa was protected from the protease cleavage upon interaction with RX-5902 (FIG. 4). To identify this protected protein, the bands along with control were sliced out, and analyzed with LC-MS/MS by ProtTech (Phoenixville, Pa.). Western blot analysis was carried out using antibodies against several potential candidates from LC-MS/MS analysis that have a similar mobility in SDS-PAGE to confirm the protected protein by RX-5902 treatment. Clearly, this protected band was recognized by the antibody against p68 RNA helicase (FIG. 5), indicating that RX-5902 may interact with p68 RNA helicase in cells and protect p68 from degradation by thermolysin. To verify the interaction of RX-5902 with p68, $^3$H-labeled RX-5902 was used. The interaction of $^3$H-labeled RX-5902 with recombinant p68 protein and the in vitro tyrosyl phosphorylated recombinant p68 protein was probed by filter binding assays (Coombs et al., supra). Through western blot analysis, it was confirmed that p68 was phosphorylated on a tyrosine residue (FIG. 6). A filter binding assay clearly showed RX-5902 interacted with the Y593 phospho-p68 with an estimated Kd around 19 nM, but RX-5902 did not interact with unphosphorylated p68 in the filter binding studies (FIG. 7; squares and triangles represent duplicate experiments).

Figure 7:
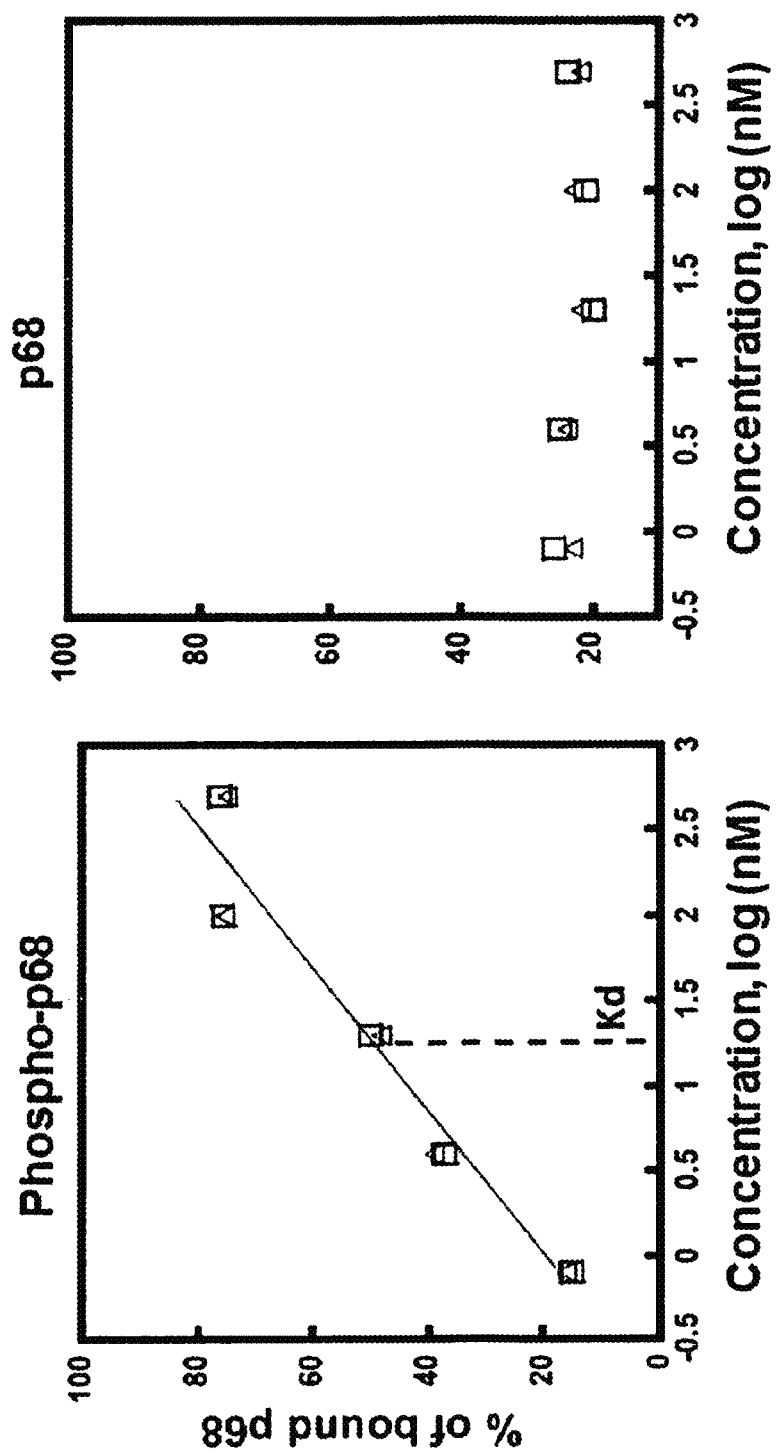
FIG. 7 are graphs showing the percentage of phospho-p68 and unphosphorylated p68 bound to $^3$H-labeled RX-5902 in filter binding assays. The Kd is estimated by 50% of p68 bound to RX-5902.
Figure 8:
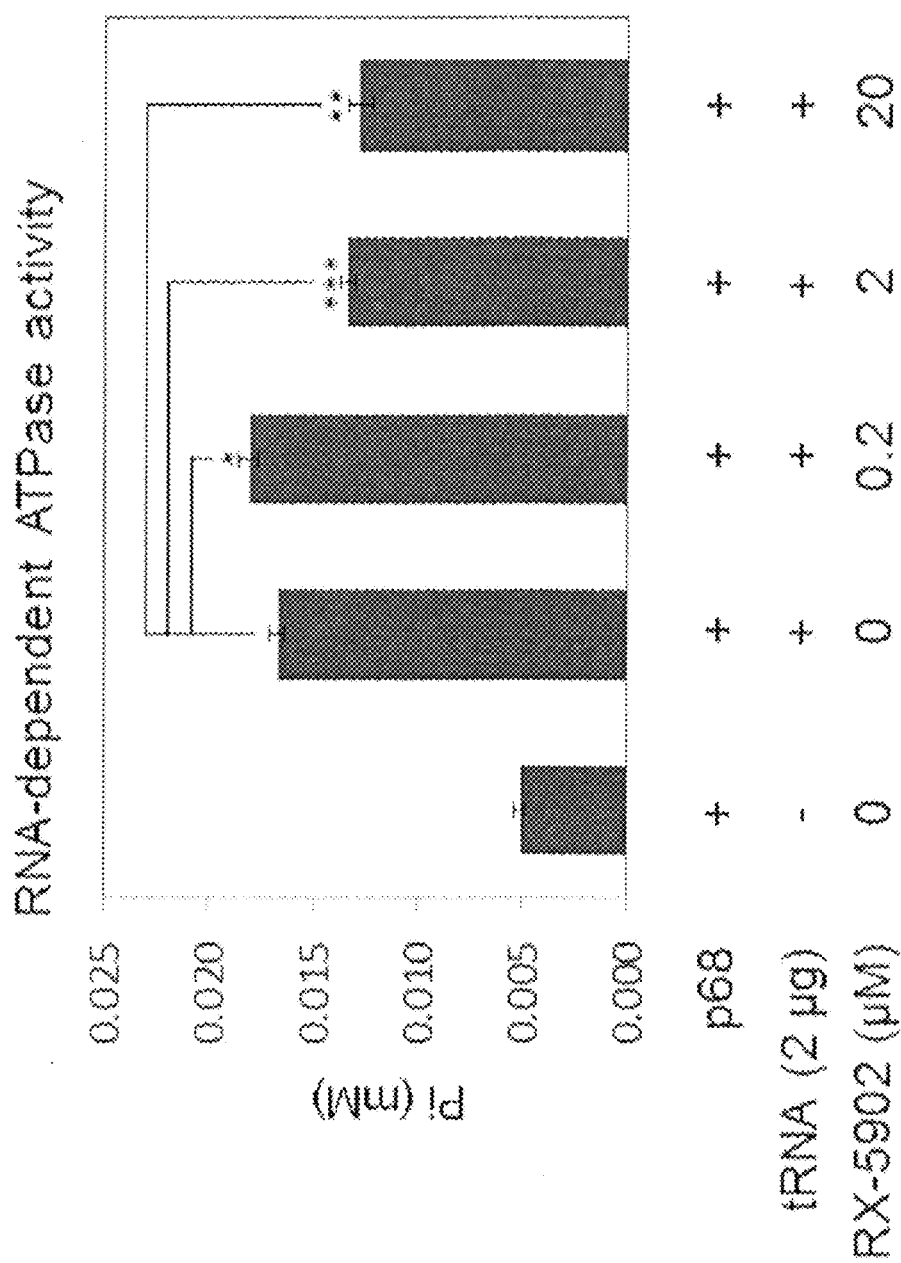
FIG. 8 is a bar graph showing the RNA-dependent ATPase activity of p68 in the presence of 0 to 20 μM RX-5902 and total RNA extracted from 2 μg yeast.

The effect of RX-5902 on ATPase activity of p68 was investigated. To do this, ATPase activity of recombinant p68 in the presence of RX-5902 and total RNA extracted from yeast were measured. RX-5902 did not affect RNA-dependent ATPase activity of p68 RNA helicase at 0.2 µM and even at high concentrations such as 20 µM, RNA-dependent ATPase activity was inhibited by less than 30% (FIG. 8), indicating RX-5902 had very little effect on RNA-dependent ATPase activity of p68. This data could confirm that RX-5902 did not interact with unphosphorylated p68 in the filter binding assay (FIG. 7).

Figure 9:
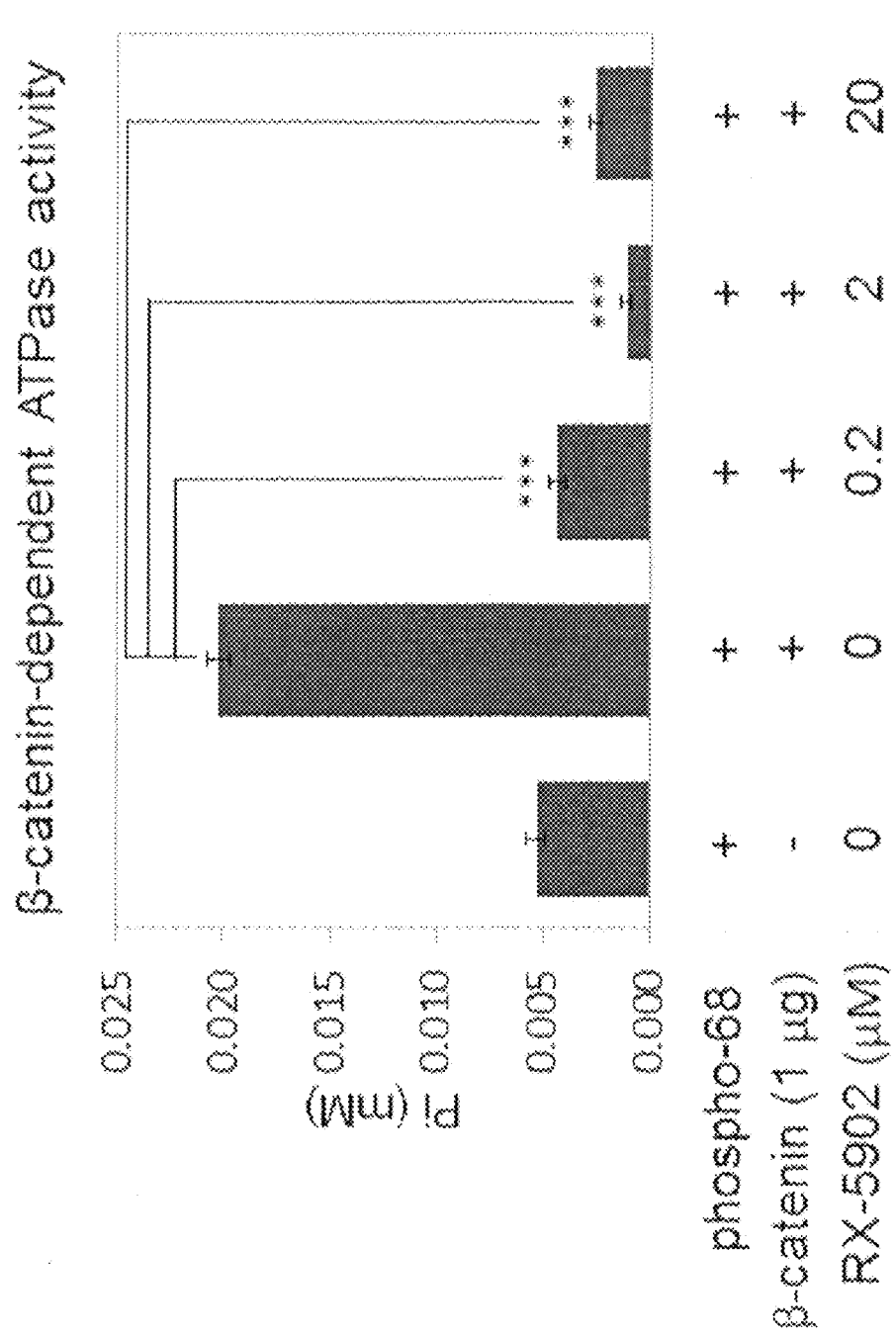
FIG. 9 is a bar graph showing the β-catenin-dependent ATPase activity of p68 in the presence of 0 to 20 μM RX-5902 and 1 μg β-catenin.
Figure 10:
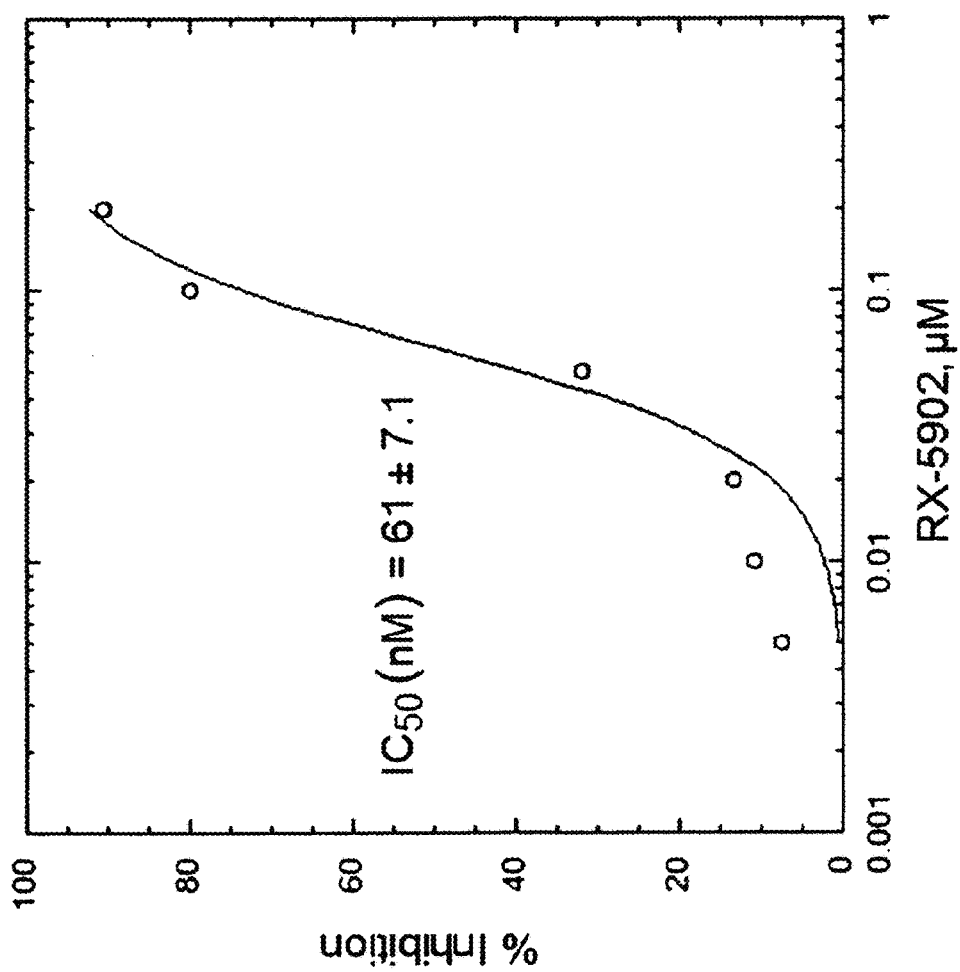
FIG. 10 is a graph showing the $IC_{50}$ determination of RX-5902 for the inhibition of β-catenin dependent ATPase activity of phospho-p68. $IC_{50}$ was determined to be 61±7.1 nM.

The results show that the β-catenin dependent ATPase activity of phospho-p68 was largely diminished in the presence of RX-5902 at 0.2 µM (FIG. 9). The experiment was repeated at lower concentrations of RX-5902 to calculate $IC_{50}$. The $IC_{50}$ of RX-5902 for the inhibition of β-catenin dependent ATPase activity was calculated to be 61 nM (FIG. 10); indicating that RX-5902 potentially disrupts the phospho-p68/β-catenin interaction.

Figure 11:
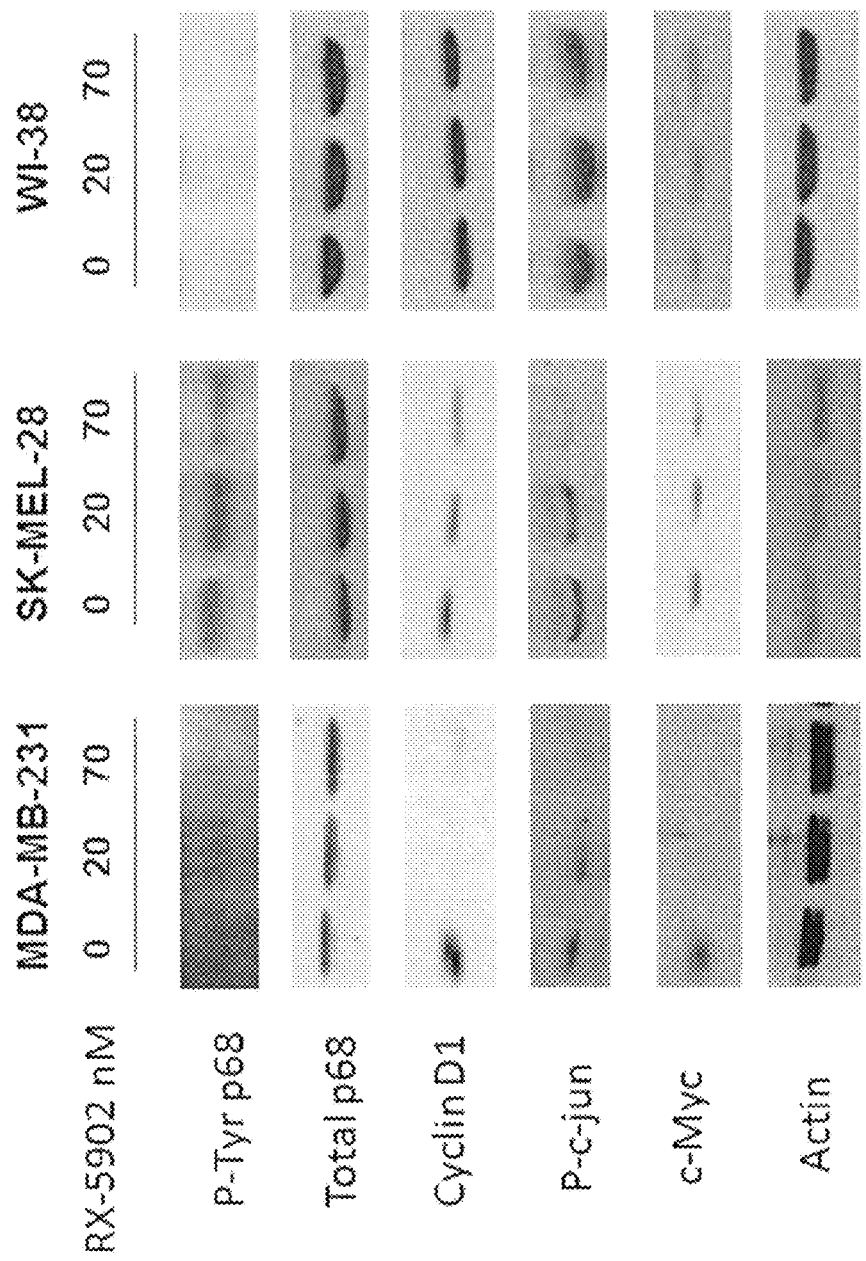
FIG. 11 are Western blots showing the suppression of the expression of cyclin D1, c-Myc, and p-c-Jun by RX-5902.

Since RX-5902 directly binds to Y593 phospho-p68, it was hypothesized that treatment of cells with RX-5902 would interfere with the phospho-p68/β-catenin interaction and consequently affect the expression of several growth associated genes, including p-c-Jun, c-Myc and cyclin D, which are regulated by phospho-p68/β-catenin interaction. Thus, cyclin D1 and c-Myc expression, as well as phosphorylation of c-Jun in cells treated with RX-5902, were analyzed. Cancer cell lines, SK-MEL-28 and MDA-MB-231, and normal fetal lung fibroblasts, WI-38, were used. Although 20 nM RX-5902 did not change protein levels, 70 nM RX-5902 led to a decrease in expression of both cyclin D1 and c-Myc and a decrease in c-Jun phosphorylation in SK-MEL-28 without changing the level of total p68 protein. Similar changes in protein levels were detected in MDA-MB-231 with both 20 nM and 70 nM RX-5902. RX-5902 did not result in any significant change in cyclin D1 or c-Myc expression or c-Jun phosphorylation in WI-38 cells (FIG. 11), even at 70 nM. The results demonstrate that treatment of cancer cells with RX-5902 resulted in the downregulation of the expression of certain genes which are known be regulated by the β-catenin pathway, such as c-Myc, cyclin D1 and p-c-Jun. Therefore, the study indicates that inhibition of Y593 phospho-p68 helicase-β-catenin interaction by direct binding of RX-5902 to Y593 phospho-p68 RNA helicase may contribute to the anti-cancer activity of this compound.

Example 12: Efficacy, Safety and Tolerability of Rx-5902 in Humans

The efficacy, safety and tolerability of RX-5902 at various doses and frequencies are evaluated. In the Phase 1 portion of the study, subjects with advanced solid tumor malignancies are enrolled. During the Phase 1 portion of the study, the maximum tolerated dose (MTD) or recommended phase 2 dose (RP2D) and schedule are determined and the pharmacokinetics of RX-5902 characterized in eligible subjects. Subjects with advanced malignant tumors are administered capsules containing RX-5902 at doses of 125-1050 mg/day 1, 3, 5, or 7 day(s) a week for 3 weeks with 1 week off during each 4 week cycle, or 4 weeks without a week off during the 4 week cycle. Dose escalation begins with an accelerated design treating 1 subject per dose (Simon et al., *J. Natl. Cancer Inst.*, 89(15):1138-47 (1997) followed by a standard 3+3 design using a modified Fibonacci sequence after the occurrence of a single related Grade 2 or greater adverse event.

In the Phase 2 portion, subjects are enrolled in 1 of 2 diagnosis groups: triple negative breast cancer or platinum resistant/refractory/relapsed ovarian cancer. The Phase 2 portion of the study uses the dose and schedule identified in the Phase 1 and follows a 2-stage design. An interim analysis is conducted when 10 response evaluable subjects in each tumor indication are enrolled and have had the opportunity to complete a minimum of 4 cycles of therapy or have discontinued therapy due to progressive disease. In the second stage of Phase 2, enrollment for a disease group proceeds if at least 2 responses are observed within the first 10 response-evaluable patients enrolled in that disease group. Approximately 40 additional subjects are enrolled in each of the disease indications. In the second stage of Phase 2, overall response rate and progression free survival rate is further evaluated in the disease groups that continue beyond the first stage. Table 6 summarizes the potential dose and schedule, but this schedule may change based on safety and tolerability data.

TABLE 6

Dosing Schedule

| Dose Group | Doses per Week | Daily dose (mg) | Total weekly dose (mg) | Weeks of Dosing* |
|---|---|---|---|---|
| 1 | 5 | 150 | 750 | 3 |
| 2 | 3 | 250 | 750 | 3 |
| 3 | 3 | 300 | 900 | 3 |
| 4 | 5 | 150 | 750 | 3 or 4 |
| 5 | 5 | 200 | 1000 | 3 or 4 |
| 6 | 5 | 250 | 1250 | 3 or 4 |
| 7 | 5 | 300 | 1500 | 3 or 4 |
| 8 | 5 | 350 | 1750 | 3 or 4 |
| 9 | 5 | 400 | 2000 | 3 or 4 |
| 10 | 7 | 200 | 1400 | 3 or 4 |
| 11 | 7 | 300 | 2100 | 3 or 4 |
| 12 | 7 | 350 | 2450 | 3 or 4 |
| 13 | 7 | 400 | 2800 | 3 or 4 |

*indicates weeks of dosing out of a 4-week cycle

Example 13: Small Scale Production of RX-5902 (Preparation of Batch 35444A)

Example 13A Production of Compound A

A 100-L reactor was charged with 1,2-diamino-4-fluorobenzene (1.75 kg, 13.8 mol, ChemiK), oxalic acid (1.25 kg, 13.9 mol), 11.4 kg water and 3.8 kg conc. hydrochloric acid (3 M HCl solution, 3.28 equiv HCl). The dark mixture was heated at reflux (95-100° C.) for ~25 h. An aliquot (1 mL) was taken while stirring and neutralized with saturated NaHCO$_3$ solution (30 mL) to a pH of 8. HPLC analysis showed that the starting material was completely consumed.

The mixture was removed from heating, allowed to cool to room temperature, and then cold water (14 kg) was added. A dark solid precipitated and was collected by vacuum filtration. The filter cake was washed with cold water (12 kg), followed by isopropyl alcohol (IPA, 9.4 kg). The wet caked (3.4 kg) was then dried overnight in a vacuum oven (50° C.) to give 2.38 kg (96% molar yield) of 6-fluoro-1,4-dihydroquinoxaline-2,3-dione (Compound A) as a blue-gray solid with an HPLC purity of 97.0%.

Example 13B Production of Compound B

To a 100-L reactor was added Compound A (2.38 kg, 13.2 mol), dimethylformamide (DMF, 0.25 kg) and CHCl$_3$ (37.0 kg). Then, thionyl chloride (SOCl$_2$, 4.9 kg, 41.2 mol) was added to maintain temperature <25° C. The mixture was then refluxed at 55-60° C. After 23 h, a sample was taken for HPLC analysis. HPLC analysis showed complete consumption of starting material but what appeared to be ~2% of an intermediate, in addition to 98% 2,3-dichloro-6-fluoroquinoxaline (Compound B). An additional amount of SOCl$_2$ (494 g) and DMF (25 g) was added and the mixture refluxed an additional 1 h. The HPLC was unchanged so the reaction mixture was cooled to room temperature and deionized (DI) water (8.8 kg) was added slowly into the reaction mixture, which resulted in evolution of heat and gas. This was followed by slow addition of 0.5 M NaOH (8 kg). The entire quench was stirred 13 h to help decompose the excess SOCl$_2$. The organic layer was washed with 4×8 kg water followed by 8×16 kg water washes.

The organic phase (in a 50 L reactor) was treated with 40 g of activated carbon and agitated for 35 minutes. The activated carbon was removed by filtration and the batch was concentrated to dryness. The resulting solid was dried in a vacuum oven (46° C.) to give 2.62 kg (94% molar yield) of Compound B with an HPLC purity of 98.0%.

Example 13C Production of Compound 1

To a 100-L reactor was added 2,3-dichloro-6-fluoroquinoxaline (Compound B, 1.30 kg, 6.00 mol), acetonitrile (32.0 kg) and ammonium hydroxide (11.9 kg). The mixture was stirred at 50° C. for 28 h. Approximately 4% of unreacted Compound B was observed. An additional 1.2 kg of ammonium hydroxide was added and the mixture was stirred an additional 20 h at 50° C. HPLC analysis showed no remaining starting material. The batch was cooled to 20° C. and the solids were vacuum filtered using Buchner filter, rinsed with ACN/water and dried in a vacuum oven overnight at 50° C. to yield 972 g of crude 3-amino-2-chloro-6-fluoroquinoxaline (Compound 1). The reaction was repeated at the same scale a second time, affording 954 g of crude Compound 1. The combined crops (1.92 kg) were slurried in 27 kg water for 30 min, then filtered and dried at 50° C. in a vacuum for ~40 h, affording 1.90 kg of desalted, crude Compound 1. A portion of the material (0.63 kg) was recrystallized by dissolution in acetonitrile (55 kg) at 75-80° C. and cooling to ambient temperature. The cake was isolated by filtration and dried in a vacuum oven at 5° C. for ~20 h. A 0.286 kg portion of purified Compound 1 was obtained (HPLC: 98.9%, 1.0% regioisomer). A large percentage of solids were left in the reactor for the next iteration of the recrystallization process. Starting again from 0.63 kg of crude material and this time utilizing 76 kg acetonitrile (to account for solids from the first portion), a recovery of 0.686 kg was obtained (HPLC: 98.8%, 0.9% regioisomer). Finally, the last portion (0.63 kg) was recrystallized as before from 55 kg acetonitrile to afford 0.505 kg of isolated product (HPLC: 98.8%, 0.9% regioisomer). The total yield was 1.48 kg (62% overall yield) of Compound 1.

Example 13D Production of Compound 2

Toa 100-L round bottom flask was added 3-amino-2-chloro-6-fluoroquinoxaline (Compound 1, 1.48 kg, 7.49 mol) and THF (26.7 kg). Then 25 wt % NaOCH$_3$ in MeOH (12.1 kg, 56.0 mol, 7.5 equiv) was added so as to maintain temperature of 20±10° C. The mixture was stirred at room temperature for 2 h. HPLC showed the starting material was consumed. The solution was concentrated under reduced pressure to approximately 21 L and then partitioned overnight between dichloromethane (DCM, 34 kg) and water (34 kg). The aqueous layer was separated and then the organic layer was further diluted with another portion of DCM (34 kg). The organic layer was washed with water until the pH of the aqueous layer reached 5 (4×19 kg washes). The organic layer was concentrated to give a solid. The solids were slurried in DCM (2.1 kg), filtered and the wet cake was washed with DCM (1×5 kg). The wet cake was dried under vacuum at 44° C. overnight to afford 1.06 kg (73.3% yield) of 3-amino-6-fluoro-2-methoxyquinoxaline (Compound 2), HPLC: 97.0% (0.7% regioisomer).

Example 13E Production of Compound 3

To a 100-L reactor was added 3-amino-6-fluoro-2-methoxyquinoxaline (Compound 2, 1.06 kg, 5.48 mol), DCM (21.4 kg) and pyridine (0.63 kg, 7.97 mol). The mixture was stirred at room temperature and then ethyl chloroformate (872 g, 8.0 mol, 1.46 equiv) was slowly added while maintaining the temperature below 30° C. After 18.5 h at room temperature, the reaction was found to be incomplete. More ethyl chloroformate (174 g, 1.6 mol) and pyridine (126 g, 1.6 mol) were added. The reaction was then complete by HPLC analysis after an additional 28.5 h mixing at room temperature. The organic phase was extracted with deionized water until a pH of 5.8 was obtained (4×16.1 kg). The organic layer was dried with magnesium sulfate (970 g), filtered and concentrated to dryness. Ethyl acetate (3.2 kg) was then charged and the resulting solids were collected via vacuum filtration. The wet cake was washed with ethyl acetate (1.3 kg) and dried overnight under vacuum at 43° C. to yield ethyl-N-(6-fluoro-2-methoxyquinoxaline-3-yl) carbonate (Compound 3) (HPLC purity 100%, 1.116 kg, 76.7% yield).

Example 13F Production of RX-5902

To a 100-L reactor was added 1-(3,5-dimethoxyphenyl) piperazine HCl (DMPP, 1.588, 6.14 mol), ethyl-N-(6-fluoro-2-methoxyquinoxaline-3-yl) carbonate (Compound 3, 1.12 kg, 4.22 mol) and THF (30.6 kg). The mixture was stirred at ambient temperature for 15 mins and 1,8-diazabicycloundec-7-ene (DBU, 2.444 kg, 14.7 mol) was added. The mixture was mixed at reflux (~66° C.) for ~4 h, then sampled for reaction completion (HPLC result: 1.1% Compound 3 remaining). The reaction was deemed complete. The mixture was concentrated under vacuum to ~11 L volume. The solution was diluted with DCM (20.2 kg) and washed with ~12 kg of 1M HCl. The organic layer was further washed with 4×10 kg portions of water until the pH of the aqueous waste layer was 5-6. The organic layer was dried over anhydrous magnesium sulfate (1.2 kg) and the filtered through a Buchner funnel. The cake was rinsed with 5 kg of DCM and the filtrate was concentrated under vacuum to a final volume of 6 L. Heptane (0.868 kg) was then added and the slurry mixed at 10-15° C. for ~16 h. The slurry was filtered and washed with heptane (2.62 kg). The wet cake (2.45 kg) was then dried in a vacuum oven. After ~48 h at 66° C., IP (In Process) testing showed THF (4506 ppm) and DCM (3250 ppm) to be above the limits After an additional 96 h at 66° C., only the THF (1141 ppm) was still above the limit. After an additional 24 h at 66° C., the residual THF dropped to 770 ppm. Finally, after another 24 h at 67° C., the THF level dropped to a passing level (679 ppm). The material was then removed from the oven to afford RX-5902 as an off-white solid (1.514 kg, 81.2% yield). HPLC: RRT 0.57 impurity of 0.82% above the spec limit of NMT 0.50%.

RRT 0.57 as identified by mass spectrometry is believed to correspond to a demethylated form of RX-5902.

Example 13G Purification of RX-5902

To a 100-L reactor was added RX-5902 from Example 13F (1.318 kg, 2.99 mol) and DCM (17.5 kg). The solution was washed with ~7 kg of 0.5 M NaOH (aq). The organic layer was further washed with 4×5.3 kg portions of water until the pH of the aqueous waste layer was 5-6. The organic layer was dried over anhydrous magnesium sulfate (0.6 kg) and then filtered through a Büchner funnel. The cake was rinsed with 2 kg of DCM and the filtration was concentrated under vacuum to a final volume of 4 L. Heptane (2.70 kg) was added and the slurry mixed at 10-15° C. from ~15 h. The slurry was filtered and washed with heptane (1.86 kg). The wet cake was then dried in a vacuum oven. After ~48 h at 55° C., IP (In Process) testing showed passing levels of all solvents. The material was removed from the oven to afford RX-5902 as an off-white solid (1.14 kg, 86.5% recovery).

Example 14: Fixed Reactors/Large Scale Production of RX-5902 (Preparation of Batch 35921A)

Below details the production of 10.96 kg of cGMP batch for RX-5902 was conducted under the following improved process conditions using fixed 35, 100, 124, 200 and 300 gallon glass, stainless and Hastelloy lined reactors and stainless steel or Hastelloy Aurara filters.

Example 14A Production of Compound A

A 35 gallon reactor was charged with 1,2-diamino-4-fluorbenzene (7.50 kg, 59.46 mol, ChemiK), oxalic acid (5.35 kg, 59.42 mol) and 3 M HCl solution (95.8 kg water and 37.8 kg conc. hydrochloric acid). The dark mixture was heated at reflux (100±5° C.) for ~21 h. An aliquot (1 mL) was taken while stirring and neutralized with saturated $NaHCO_3$ solution (30 mL) to a pH of 8. HPLC analysis showed that the starting material was completely consumed.

The mixture was removed from heating, allowed to cool to ambient temperature and then cold water (55 kg) was added. A dark solid precipitated and was collected by vacuum filtration. The filter cake was washed with cold water (50.0 kg) followed by Isopropyl Alcohol (IPA, 39.14 kg). The wet cake (11.43 kg) was then dried overnight in a vacuum oven (50±5° C.) to give 10.3 kg (96% molar yield) of 6-fluoro-1,4-dihdryoquinoxaline-2,3-dione (Compound A) as a blue-gray solid with an HPLC purity of >99%). The process was repeated on the identical scale to provide 9.95 kg (>99%).

Example 14B Production of Compound B

To a 200 gallon reactor was added 6-fluoro-1,4-dihdryoquinoxaline-2,3-dione (Compound A, 20.25 kg, 112.41 mol), DMF (2.20 kg) and chloroform (310.3 kg). Thionyl chloride (40.95 kg) was added while maintaining the temperature <25° C. The mixture was refluxed at 50-55° C. After 21 h, a sample was taken for HPLC analysis. HPLC analysis showed complete consumption of starting material with 97.7% (by area) of Compound B. The reaction mixture was cooled to ambient temperature (25±5° C.) and DI water (64.7 kg) was added slowly into the reaction mixture, which resulted in evolution of heat and gas. Next, 0.5 M NaOH (64.7 kg) was added slowly. The entire quench was stirred for 13 h to help decompose the excess $SOCl_2$. The organic layer was washed with 8×32.8 kg water.

The organic phase (in a 200 gallon reactor) was concentrated by atmospheric distillation until approximately 3 gallon remained. As distillation was progressing, heptane (69.5 kg) was added to the distillation pot. Distillation continued until pot temperature exceeded 70° C. (70.3° C.). The pot was cooled to 10-15° C. and stirred for 12 h. The slurry was filtered and washed with heptane (2×16.0 kg). The resulting wet solid (20.65 kg) was dried in a vacuum oven without heat for 25 h at 45±5° C. to give 14.80 kg (64.5% yield) of 2,3-dichloro-6-fluoroquinoxaline (Compound B) with an HPLC purity of 97.7%.

Due to the low yield, the mother liquor was reprocessed. The mother liquor was distilled under vacuum until approximately 30 gallons had been removed (~12 gallons remained in the pot). The jacket was set to 40° C. Once distillation was complete, the suspension was cooled to 10-15° C. (actual 13.2° C.) and stirred for over 3 h. The slurry was filtered and washed with heptane (2×16.0 kg). The resulting wet solid (10.50 kg) was dried in a vacuum oven at 45±5° C. for over 18 h to give 3.62 kg of 2,3-dichloro-6-fluoroquinoxaline (Compound B, second lot) with an HPLC purity of 98.4%. The total yield was 75.5% (18.45 kg).

Example 14C Production of Compound 1

To a 200 gallon reactor was added 2,3-dichloro-6-fluoroquinoxaline (Compound B, 18.45 kg, 85.01 mol), acetonitrile (448.60 kg) and ammonium hydroxide (169.80 kg). The mixture was stirred at 50° C. for nearly 24 h. HPLC analysis showed no remaining starting material. The batch was tooled to 45±5° C. and stirred for nearly 25 h. The solids were vacuum filtered, washed with water (2×14.0 kg) and acetonitrile (2×36.1 kg). The wet cake (16.70 kg) was dried in a vacuum overnight at 50° C. for 49 h to yield 3-amino-2-chloro-6-fluoroquinoxaline (Compound 1, 12.20 kg, 72.7% yield). Compound 1 was obtained (HPLC: 97.86%, 1.83% regioisomer).

Example 14D Production of Compound 2

To a 200 gallon glass-lined reactor was added 3-amino-2-chloro-6-fluoroquinoxaline (Compound 1, 12.10 kg, 61.23 mol) and THF (212.20 kg) followed by 25 wt % NaOCH$_3$ in MeOH (91.80 kg) so as to maintain the temperature at 20±10° C. The mixture was stirred at ambient temperature for ~4 h. HPLC showed the starting material was consumed. Water (43.50 gal) was added while keeping the internal temperature <35° C. The solution was concentrated through atmospheric distillation until ~55 gallons remained (~63 gallons were removed). The solution temperature was cooled to 15-20° C. and stirred for ~18 h. The slurry was filtered and washed with water (2×8.0 gallon). The resulting wet solid was dried in a vacuum oven at 50±5° C. for almost 96 h to afford 7.40 kg (62.6% yield) of 3-amino-6-fluoro-2-methoxyquinoxaline (Compound 2) with an HPLC purity of 99.1%; regioisomer was not detected.

Example 14E Production of Compound 3

To a 100 gallon reactor was added 3-amino-6-fluoro-2-methoxyquinoxaline (Compound 2, 7.40 kg, 3.8.30 mol), DCM (144.6 kg) and pyridine (3.6 kg). The mixture was stirred at ambient temperature and then ethyl chloroformate (6.9 kg, 63.58 mol) was slowly added while maintaining the temperature <30° C. After 21.5 h at ambient temperature, the reaction was found to be complete. The organic phase was washed with DI water until a pH of 5.8 was obtained (3×16.4 gallons). The organic layer was distilled under atmospheric pressure until ~16 gallons remained. Ethyl acetate (47.4 kg) was added during the distillation. The suspension was cooled to 10-15° C. and stirred for 22 h. The solids were collected by vacuum filtration and washed with ethyl acetate (2×8.3 kg) and dried (7.8 kg wet) overnight under vacuum at 40±5° C. to afford ethyl-N-(6-fluoro-2-methoxyquinoxaline-3-yl) carbonate Compound 3 (7.30 kg, 71.8% yield). HPLC: 100%; regioisomer was not detected.

Due to the low recovery, the mother liquor from above was concentrated under vacuum to approximately half of its original volume (17 L). The solids were filtered and rinsed with ethyl acetate (2×1.5 L). The wet cake (1.6 kg) was dried at 40±5° C. for 36 h to afford additional 1.35 kg of Compound 3 (E-166). The total yield was 85:1% (8.65 kg).

Example 14F Production of RX-5902

To a 200 gallon reactor was added 1-(3,5-dimethoxyphenyl) piperazine HCl (DMPP) (12.50 kg, 48.31 mol), ethyl-N-(6-fluoro-2-methoxyquinoxaline-3-yl) carbonate (Compound 3, 8.65 kg, 32.61 mol) and THF (249.6 kg). The mixture was stirred at ambient temperature for 15 minutes and DBU (17.60 kg, 115.6 mol) was added. The mixture was mixed at reflux (~66° C.) for ~4 h and cooled to 20±10° C. A sample analyzed by HPLC showed the reaction was complete (HPLC result: 0.6% Compound 3 remaining versus IP test limit of NMR 2.0%). The mixture was concentrated under vacuum to ~86 L volume. The solution was diluted with DCM (159.70 kg) and washed with 1M HCl (8.9 kg conc. HCl in 24.1 gallon water). The organic layer was further washed with water (4×30.0 gallons) until the pH of the aqueous waste layer was 5-6. The organic layer was further washed with) 0.5 N sodium hydroxide (2.9 kg of 50% sodium hydroxide and 18.6 gallon of water) and washed with water (3×25.0 gallons) until the pH of the aqueous waster layer was 5-6. The organic layer was dried over magnesium sulfate (9.5 kg) and filtered through a Buchner funnel. The cake was rinsed with DCM (19.5 kg) and the filtrate was then concentrated under vacuum with DCM (19.5 kg). The filtrate was concentrated under vacuum to a final volume of 47 L. Heptane (7 kg) was added and the slurry was mixed at 10-15° C. for ~16 h. The slurry was filtered and washed with heptane (21 kg). The wet cake (15 kg) was dried in a vacuum over at 60° C. for ~48 h. IP testing showed THF (10,800 ppm) and DCM (15,395 ppm) to be above the spec limits After an additional 86 h at 60° C., all solvent levels passed the residual solvent specifications. The material was removed from the oven to afford RX-5902 as an off-white solid (10.965 kg, 76.2% yield).

Example 15: RX-5902 Nanoformulation Process for 1.3 Kg Batch-Reprocessing of Previously Prepared RX-5902

Example 15A 100 mg/g Nanosuspension of RX-5902

Example 15A1 Sub-Batch 1

YTZ® Grinding Media (9 kg) was washed with cleanser solution (Alconox) and rinsed with purified water (Ricca Chemical Company). The cleanser solution was prepared by mixing 5 mL of cleanser and 500 mL of purified water. The media was evenly divided between three heat-resistant containers. Each container was enclosed in an autoclave bag with the permeable side of the bag covering the opening of the container. A Tuttnauer 2540EA Electronic Table-Top Autoclave was sterilized using a validated sterilization cycle (250° F. for 45 minutes with 35 minutes drying time, see PSSOP 50042 "Operation, Maintenance and Clearing of the Tuttnauer 2540EA Electronic Table-Top Autoclave) and the containers of media were placed in the oven to dry at 110° C. overnight.

The following supplies and labware was cleaned with the cleanser solution and transferred into the cleanroom: Milling vessels (×3), Stir plates, Funnels, Disposable spatulas, Weigh containers, Magnetic stirrers, Magnetic stirrer retriever and Transfer pipettes. A hydrothermograph was set up in the manufacturing suite and the humidity and temperature were recorded. A balance was set up in the isolator and the daily verification was conducted.

Poloxamer 407, NF (Spectrum) was weighed out and charged to each of the containers. To vessel A was charged 10.68 g, to vessel B was charged 10.64 g and to vessel C was charged 10.70 g. To each of the three vessels was charged Water for Injection, USP (WFI). To vessel A was charged 299.57 g, to vessel B was charged 300.62 g and to vessel C was charged 301.19 g. A stir bar was placed into each of the three vessels and a stir plate was used to mix until the Poloxamer 407, NF was visibly dissolved into the WFI.

To each of the three containers was added by funnel RX-5902 (Pfanstiehl). To vessel A was charged 133.16 g, to vessel B was charged 133.19 g and to vessel C was charged 133.41 g. The stir plate was employed to mix the contents of the containers until RX-5902 was visibly dispersed. The stir bar was removed from each of the three containers employing a magnetic retriever. The contents of one container was charged by funnel into a milling vessel. The threads of the milling vessel were inspected to ensure the threads are free from the milling media. The lid of the milling vessel was tightened and sealed to prevent leakage.

The exterior of the milling vessel was decontaminated and removed from the isolator. A piece of reflective material was attached to the milling vessel, and the milling vessel was attached to the roller mill. The mill was activated and the rotational speed was adjusted until the cascading media inside of the vessel achieved an angle-of-break of between 45 to 60 degrees from the horizontal (visually determined). A tachometer was employed to measure the rotational speed of the milling vessel. Each of the three containers was transferred to a milling vessel and prepared using the same general procedure as described above.

Each of the three milling vessels was roller milled for 18.75 hours at 90 RPM (rotations per minute). After the roller milling was complete, the exterior of the vessels were decontaminated and transferred into the laminar-flow hood. The hydrothermograph was transferred into the same manufacturing suite to accompany the milling vessels. A sterile pipette was employed to take a 1 mL sample from each milling vessel and the samples were transferred to vials.

The three samples were analyzed for particle-size distribution by laser diffraction. The acceptance criteria for the sample was D90<1 µm (replicates and average) and a monomodal distribution profile (i.e. the distribution contains one main peak with only a slight secondary peak allowed). The results for each of the vessels were as follows:

| Vessel | D90 (replicate 1) | D90 (replicate 2) | D90 (replicate 3) | D90 (Average) |
| --- | --- | --- | --- | --- |
| A | 0.21355 µm | 0.21216 µm | 0.20778 µm | 0.21116 µm |
| B | 0.16276 µm | 0.16996 µm | 0.17200 µm | 0.16824 µm |
| C | 0.16087 µm | 0.16628 µm | 0.16291 µm | 0.16335 µm |

Each of the three vessels met the accepted criteria. The three vessels from sub-batch 1 were closed and stored at 2 to 8° C. until the extraction could be performed.

Example 15A2 Sub-Batch 2

A second sub-batch was made in an identical manner. Vessels were charged as follows:

| Vessel | Poloxamer 407, NF (Spectrum) | WFI | RX-5902 |
| --- | --- | --- | --- |
| D | 10.64 g | 299.95 g | 132.94 g |
| E | 10.62 g | 300.61 g | 133.32 g |
| F | 10.65 g | 299.73 g | 133.32 g |

Each of the three milling vessels was roller milled for 19.25 hours at 90 RPM (rotations per minute). After the roller milling was complete, the exterior of the vessels were decontaminated and transferred into the laminar-flow hood. The hydrothermograph was transferred into the same manufacturing suite to accompany the milling vessels. A sterile pipette was employed to take a 1 mL sample from each milling vessel and the samples were transferred to a vials.

The three samples were analyzed for particle-size distribution by laser diffraction. The acceptance criteria for the sample was D90<1 µm (replicates and average) and a monomodal distribution profile (i.e. the distribution contains one main peak with only a slight secondary peak allowed). The results for each of the vessels were as follows:

| Vessel | D90 (replicate 1) | D90 (replicate 2) | D90 (replicate 3) | D90 (Average) |
| --- | --- | --- | --- | --- |
| D | 0.26110 µm | 0.25660 µm | 0.25724 µm | 0.25831 µm |
| E | 0.30640 µm | 0.29270 µm | 0.32984 µm | 0.30965 µm |
| F | 0.43902 µm | 0.42497 µm | 0.43438 µm | 0.43279 µm |

Each of the three vessels met the accepted criteria. The three vessels from sub-batch 2 were closed and stored at 2 to 8° C. until the extraction could be performed.

Example 15A3—Sub-Batch 3

A third sub-batch was made in an identical manner. Vessels were charged as follows:

| Vessel | Poloxamer 407, NF (Spectrum) | WFI | RX-5902 |
| --- | --- | --- | --- |
| G | 10.68 g, | 300.63 g | 133.89 g |
| H | 10.65 g | 300.48 g | 133.04 g |
| I | 10.71 g | 300.90 g. | 116.19 g |

Each of the three milling vessels was roller milled for 19.5 hours at 90 RPM (rotations per minute). The roller milling was stopped, and the exteriors of the vessels were decontaminated and transferred into the laminar-flow hood. The hydrothermograph was transferred into the same manufacturing suite to accompany the milling vessels. A sterile pipette was employed to take a 1 mL sample from each milling vessel and the samples were transferred to a vials.

The three samples were analyzed for particle-size distribution by laser diffraction. The acceptance criteria for the sample was D90<1 µm (replicates and average) and a monomodal distribution profile (i.e. the distribution contains one main peak with only a slight secondary peak allowed). The results for each of the vessels were as follows:

| Vessel | D90 (replicate 1) | D90 (replicate 2) | D90 (replicate 3) | D90 (Average) |
| --- | --- | --- | --- | --- |
| G | 66.69387 μm | 0.18573 μm | 55.32641 μm | 40.73534 μm |
| H | 0.29842 μm | 236.23581 μm | 64.05984 μm | 100.19800 μm |
| I | 75.35052 μm | 61.63898 μm | 51.83522 μm | 62.94151 μm |

None of the three vessels met the accepted criteria.

Vessels G, H and I were again sealed and returned to the roller mill. The milling was continued for 22.5 hours. The hydrothermograph was transferred to the same manufacturing suite to accompany the vessel. A sterile pipette was employed to take a 1 mL sample from each milling vessel and the samples were transferred to a vials.

The three samples were analyzed for particle-size distribution by laser diffraction. The acceptance criteria for the sample was D90<1 μm (replicates and average) and a monomodal distribution profile (i.e. the distribution contains one main peak with only a slight secondary peak allowed). The results for each of the vessels after additional milling time were as follows:

| Vessel | D90 (replicate 1) | D90 (replicate 2) | D90 (replicate 3) | D90 (Average) |
| --- | --- | --- | --- | --- |
| G | 0.17129 μm | 0.18762 μm | 0.17109 μm | 0.13000 μm |
| H | 0.17073 μm | 0.17154 μm | 0.17198 μm | 0.17142 μm |
| I | 0.16724 μm | 0.16825 μm | 0.17332 μm | 0.16966 μm |

Each of the three vessels met the accepted criteria. The three vessels from sub-batch 3 were closed and stored at 2 to 8° C. until the extraction could be performed.

Example 15B Extraction of the Sub-Batches

The following supplies and labware for the extraction were prepared: Extraction Vessels (×9), Funnels, Tubing, Hose Clamps, In-line air filter, Transfer pipettes and Filter funnel. The Balance was wiped with 70% isopropanol. These supplies were transferred to the cleanroom.

A nitrogen tank was set up in the cleanroom suite by connecting the air filter to a hose, and the hose was connected to the nitrogen tank. A hydrothermograph was set up in the manufacturing suite and the temperature and humidity were recorded.

Nine sub-batches (A-I) were prepared using the extraction process as follow. An empty collection vessel was weighed and placed under a filter funnel. The contents of milling vessel A were poured into the filter funnel and the suspension was extracted using compressed nitrogen. WFI was charged to the milling vessel. The contents were poured into the filter funnel and extracted using compressed nitrogen. WFI was charged to the milling vessel. The contents were poured into the filter funnel and extracted using compressed nitrogen. The collection vessel was weighed to afford the net suspension weight.

The collection vessel was swirled manually to mix the contents. Using a sterile transfer pipette, a sample for analytical testing was withdrawn as well as a QA sample. The final weight of the collection vessel was recorded.

All sub-batches were stored at 2 to 8° C. until the in-process assay was completed.

The yield of the nine sub-batches and the amount available for release was as follows:

| Sub-batch | Process Yield | Amount for Release |
| --- | --- | --- |
| A | 93% | 1234.94 g |
| B | 94% | 1247.05 g |
| C | 95% | 1265.06 g |
| D | 94% | 1251.18 g |
| E | 93% | 1240.57 g |
| F | 93% | 1239.88 g |
| G | 95% | 1256.83 g |
| H | 96% | 1279.70 g |
| I | 93% | 1241.99 g |

The combined total process weight from the nine sub-batches was 11287.95 g (94% yield) with 11257.21 g the total amount for release.

Example 15C Lyophilization to Afford 83% RX-5902 Nanoformulation Powder

The amount of RX-5902 in each of the nine sub-batches was calculated based on the assay analysis of each sub-batch. The assay amount, final suspension weight and amount of RX-5902 in each of the sub-batches was found to be as follows:

| Sub-batch | % Assay | Suspension Weight | Amount of RX-5902 |
| --- | --- | --- | --- |
| A | 105.6% | 1234.94 g | 130.41 g |
| B | 104.1% | 1247.05 g | 129.82 g |
| C | 101.7% | 1265.06 g | 128.66 g |
| D | 103.8% | 1251.18 g | 129.87 g |
| E | 103.7% | 1240.57 g | 128.65 g |
| F | 108.0% | 1239.88 g | 133.91 g |
| G | 108.3% | 1256.83 g | 136.11 g |
| H | 104.2% | 1279.70 g | 133.34 g |
| I | 94.5% | 1241.99 g | 117.37 g |

The total amount of RX-5902 in the nine sub-batches was 1168.14 g.

The following supplies, raw materials, equipment and labware were prepared for the lyophilization process and transferred to the cleanroom: Balance, Timer, Hydrothermograph, Bulk suspension container, Magnetic stirrer, Stir plate, Magnetic stirrer retriever, Weighing containers, Spatulas and Bulk lyophilization trays. The hydrothermograph was set up in the manufacturing suite and recorded the temperature and humidity conditions.

In the laminar-flow hood, all sub-batches were combined into the bulk container. A stir bar was added and the contents were mixed. To the bulk suspension container was added Poloxamer 407, NF (146.27 g, Spectrum). The contents of the bulk suspension container was mixed until the Poloxamer 407, NF was completely dissolved by visual inspection. The mixing was stopped and the stir bar was removed.

To each of the eight bulk lyophilization trays was added ~1/8$^{th}$ of the contents of the bulk suspension container. The lids on each of the eight trays were closed. The eight trays were transferred to the lyophilizer and the lyophilizer door was closed and sealed. The hydrothermograph was stopped.

The shelf temperature of the lyophilizer was adjusted to −40° C. and the "Freeze Shelf" function was turned on. The trays were allowed to completely freeze over 66.75 hours. The condenser was turned on and allowed to reach −53° C. The shelf temperature was then set to −25° C. and the vacuum setting was set to 250 mTorr for primary drying. After ~18 days, the difference between the last Pirani gauge (284 mTorr) and capacitance manometer (250 mTorr) readings was <1% of the previous Pirani gauge (285 mTorr) and capacitance manometer (250 mTorr) readings. The primary drying was deemed complete.

Over ~30 minute intervals, the shelf temperature setting was increased by +5° C. until the shelf setting was 20° C. After ~4 days, the difference between the last Pirani gauge (486 mTorr) and capacitance manometer (500 mTorr) readings was <1% of the previous Pirani gauge (486 mTorr) capacitance manometer (500 mTorr) readings. The secondary drying was deemed complete. The shelf control and condenser were turned off. The vacuum was turned off and released.

A mortar and pestle were prepared by washing with the cleanser solution and rinsing with purified water (Ricca Chemical Company). The cleanser solution was prepared by mixing 5 mL of cleanser and 500 mL of purified water. The mortar and pestle were placed in an autoclave bag with the permeable side of the bag facing upwards. A Tuttnauer 2540EA Electronic Table-Top Autoclave was sterilized using a validated sterilization cycle (250° F. for 45 minutes with 35 minutes drying time, see PSSOP 50042 "Operation, Maintenance and Clearing of the Tuttnauer 2540EA Electronic Table-Top Autoclave) and the bags containing the mortar and pestle were placed in the oven to dry at 250° C. for ~1 hr. The hydrothermograph was set up in the manufacturing suite and recorded the temperature and humidity conditions.

The dried trays were removed from the lyophilizer and transferred into the manufacturing suite. The holding container was weighed (3911.45 g), sanitized and transferred into a glove-box isolator. The dried lyophilized trays were wiped down and transferred into the glove-box isolator. The mortar and pestle was employed to break apart the lyophilate into freely flowing powder. The powder was transferred into the holding container.

The holding containers were weighed (5508.47 g) and sampled. From the top of the holding container was removed the top sample for homogeneity testing (1.15 g). From the middle of the holding container was removed the sample for testing (4.48 g), a QA retain (8.33 g) and a sample for micro testing (11.00 g). From the bottom of the holding container was removed a sample for the bottom homogeneity testing (1.21 g). The holding container was weighed again (5280.12 g) and the hydrothermograph was turned off.

The process batch size was calculated as 1397.02 g (97% Process yield) with a batch size for release as 1368.67 g. The analytical testing for the batch showed it met all certificate of analysis specifications.

Example 16: High-Energy Milling and Drying

Example 16A Productions of High-Energy Milled Material

The Netzsch DeltaVita agitator mill was assembled using the 150-mL recirculation chamber and a 150-micron outlet screen. About 125 mL (0.5 kg) of 0.5-mm YTZ ceramic milling media was added to the chamber and the chamber was cooled to 10° C. using a recirculating chiller. The chamber was primed for milling by pumping the starting suspension into the mill at about 100 mL per minute (48 rpm using MasterFlex size 15 tubing), and by periodically "jogging" the mill by running the agitator for a few seconds at a time to better disperse the incoming suspension. Once primed, the mill was operated at an agitator speed of 500 rpm, or 1.8 m/s tip speed. This turned out to be insufficient as the back-pressure at the suspension inlet increased to the point at which the mill automatically shut off. This is typically caused by clogging by API particles that either are too large to pass through the screen, or that tend to aggregate in the screen slots. To prevent the pressure build-up, the agitator speed was incrementally increased until the system could run without pressure increase, which was at 2,000 rpm (7 m/s).

Figure 14:
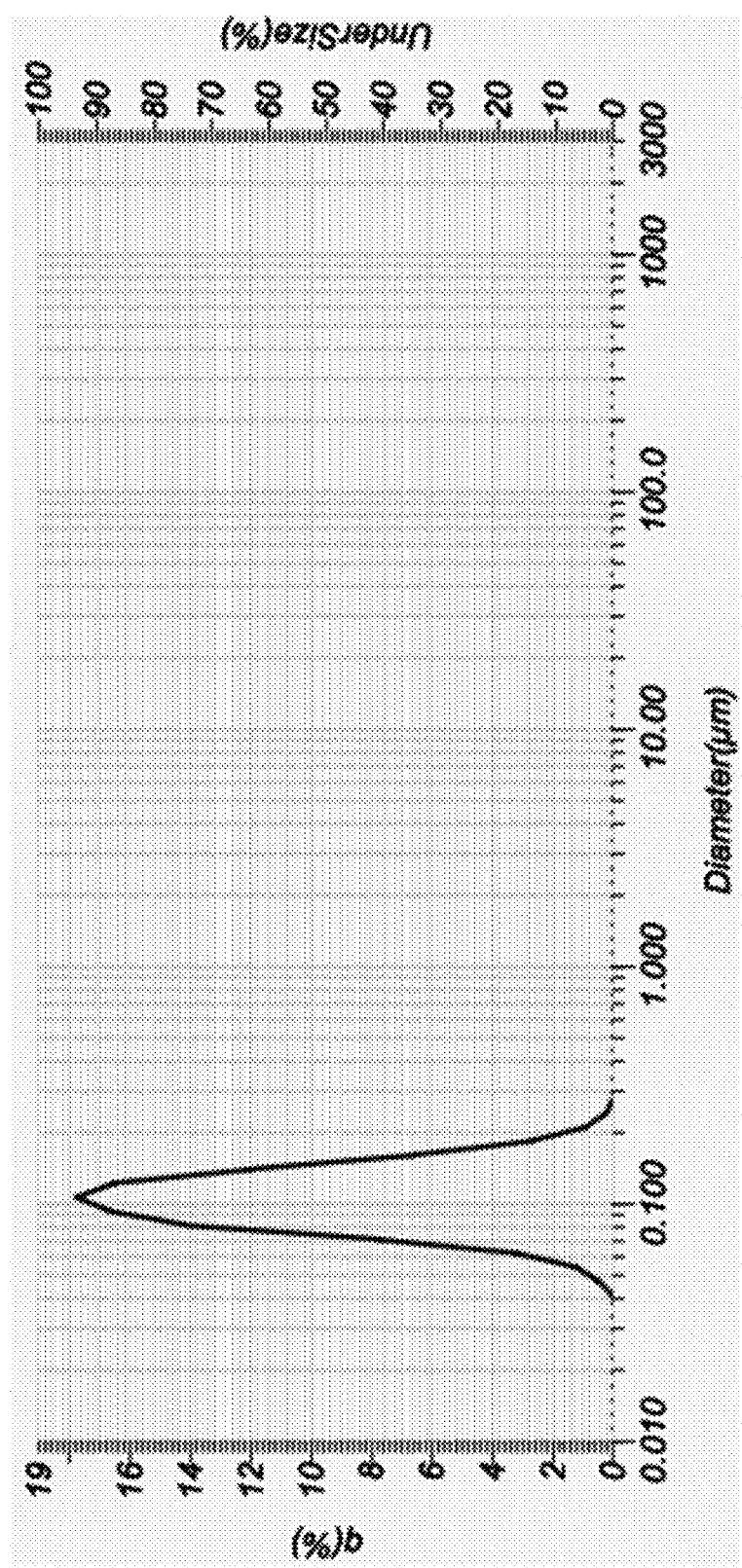
FIG. 14 is a graph showing Particle-Size Distribution of Agitator-Milled Nanosuspension.

After 18 minutes, the D90 of the suspension was reduced to about 1 micron, which is the informal limit that had been previously used as a maximum particle size for the in-process suspension. After 90 minutes of milling, the suspension solidified, an occurrence that is not uncommon when reducing particles into the size range that is typical of colloids. About 150 mL of additional purified water was added to the milling reservoir, which brought the API concentration to 20%, and which liquefied the suspension enough to continue milling. The suspension was milled for a total of 240 minutes, at which point the particle-size distribution showed a uniform, monomodal, submicron population of particles, as shown in FIG. 14. The D10 of the nanosuspension is 0.07284 median size is 0.10526 µm, and D90 is 0.15167 µm. The resulting nanosuspension was fluid and uniform, and showed no signs of discoloration or physical change from that which had been observed in the roller-milled suspensions.

Figure 15:
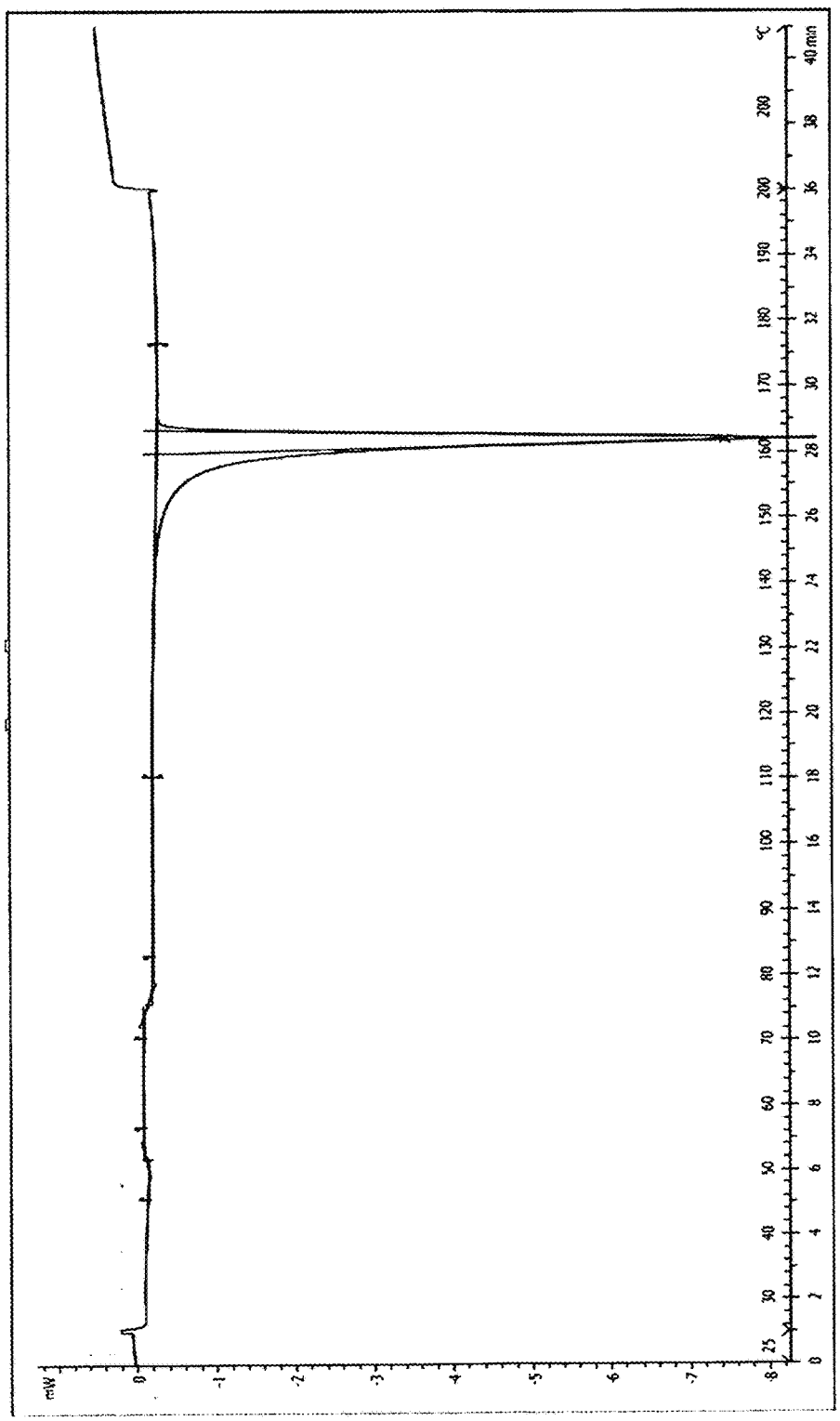
FIG. 15 is a DSC of Extracted RX-5902 Nanoparticles.

To determine if the crystal structure of RX-5902 had been altered during milling, the nanoparticles were tested by DSC and x-ray powder diffraction (XRPD). The nanoparticles were removed from suspension by centrifuge filtration (Vivaspin). The particles were washed three times with purified water in an effort to remove associated poloxamer. After washing, the particles were dried over silica. DSC analysis, pictured in FIG. 15, showed a slight reduction in melting onset (161° C.) as well as a low temperature (50° C.) thermal event, both of which indicate the presence of poloxamer (melting point=56° C.) in the isolated nanoparticles. However, no other thermal events indicative of a different crystal form of the API were observed. XRPFD analysis confirmed that the crystal structures of the milled and unmilled API were comparable.

Example 16B Productions of High-Energy Milled Lyophilized Material

High-energy milled lyophilized material was prepared lyophilizing the high-energy milled material of Example 16A using the lyophilization method of Example 15C.

Example 16C Production of High-Energy Milled Spray-Dried Material

RX-5902 nanosuspension was spray dried with a Büchi B-290 spray dryer using the parameters outlined in Table 7. The suspension was used as it had been extracted from the mill, without the addition of any excipients or purified water.

TABLE 7

| Spray-Drying Parameters | |
|---|---|
| Parameter | Value |
| Nozzle diameter | 1.40 mm |
| Inlet temperature | 100 C. |
| Aspirator | 80% |
| Pump rate | 20% |
| Q-flow | 50 |

Figure 16:
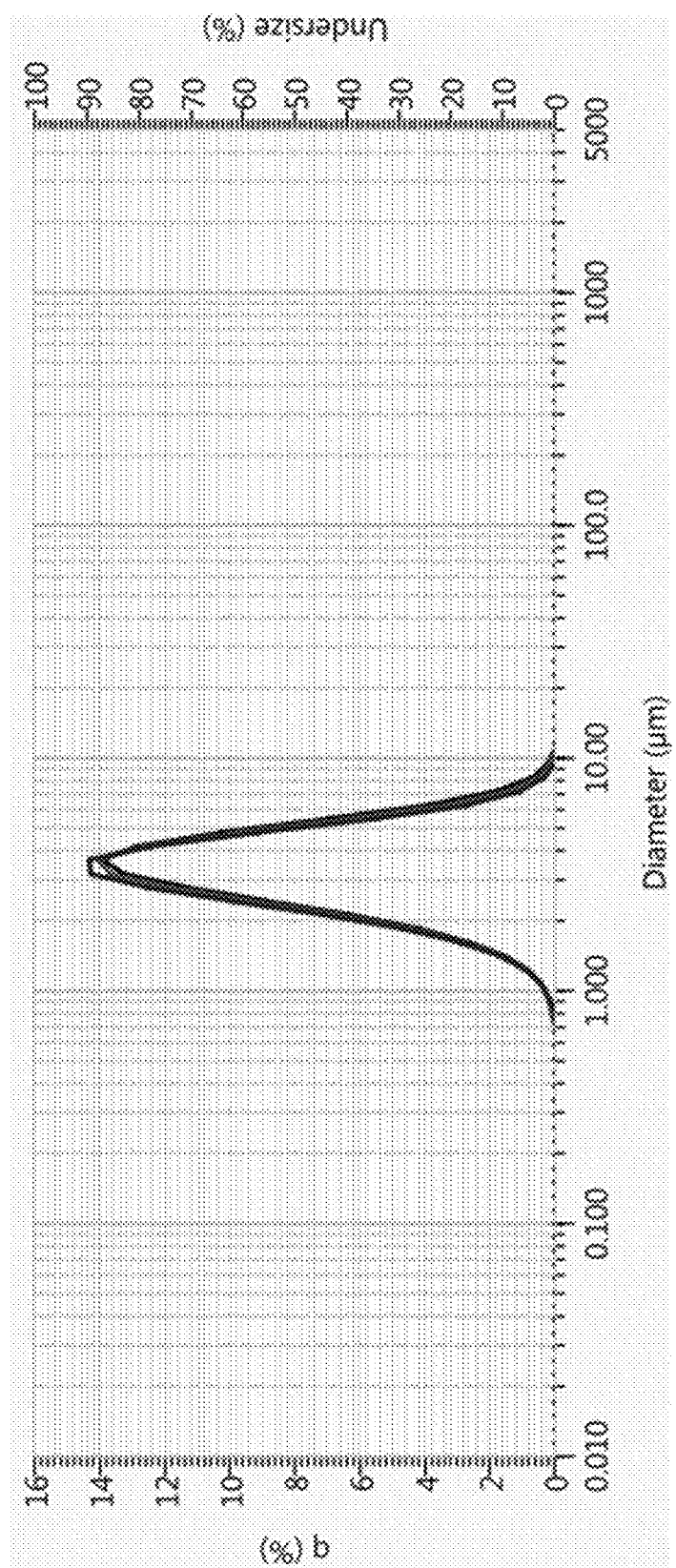
FIG. 16 is a Particle-Size Distribution of Spray-Dried RX-5902 Nanosuspension.

Minimal material loss was observed in the drying chamber of the spray dryer. The collected product was a free-flowing powder that dispersed into purified water. Particle-size measurements by laser diffraction gave a concise, repeatable distribution as shown in FIG. 16 and the measurements are shown in Table 8.

TABLE 8

Sizes of RX-5902 nanoparticles

| Batch | Mean Size | D10 | Median Size | D90 |
|---|---|---|---|---|
| 1 | 3.60752 μm | 1.99298 | 3.42597 | 5.48444 |
| 2 | 3.41835 | 1.93907 | 3.26357 | 5.08637 |
| 3 | 3.51103 | 1.95287 | 3.34039 | 5.30013 |

Figure 17:
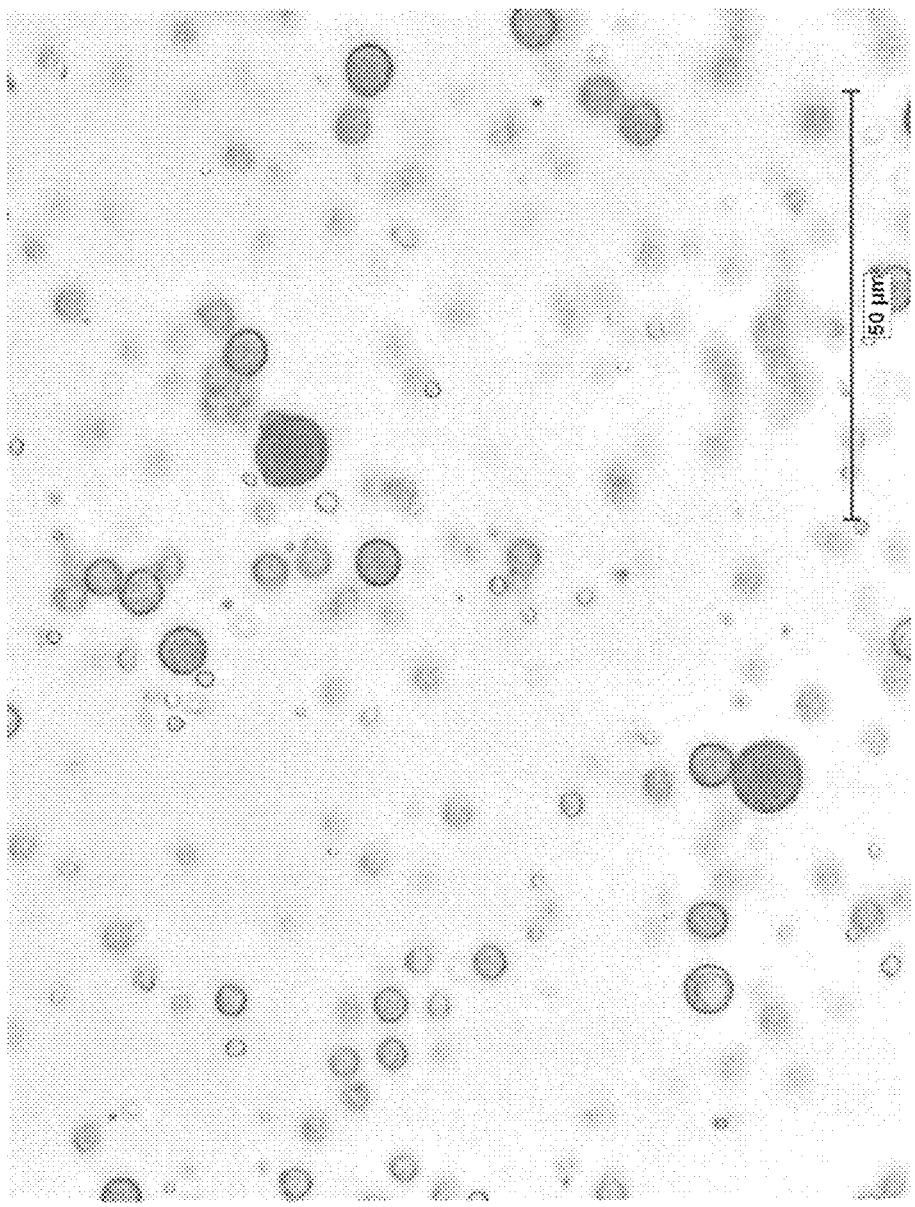
FIG. 17 shows Spray-Dried RX-5902 (1000× magnification, normal light).
Figure 18:
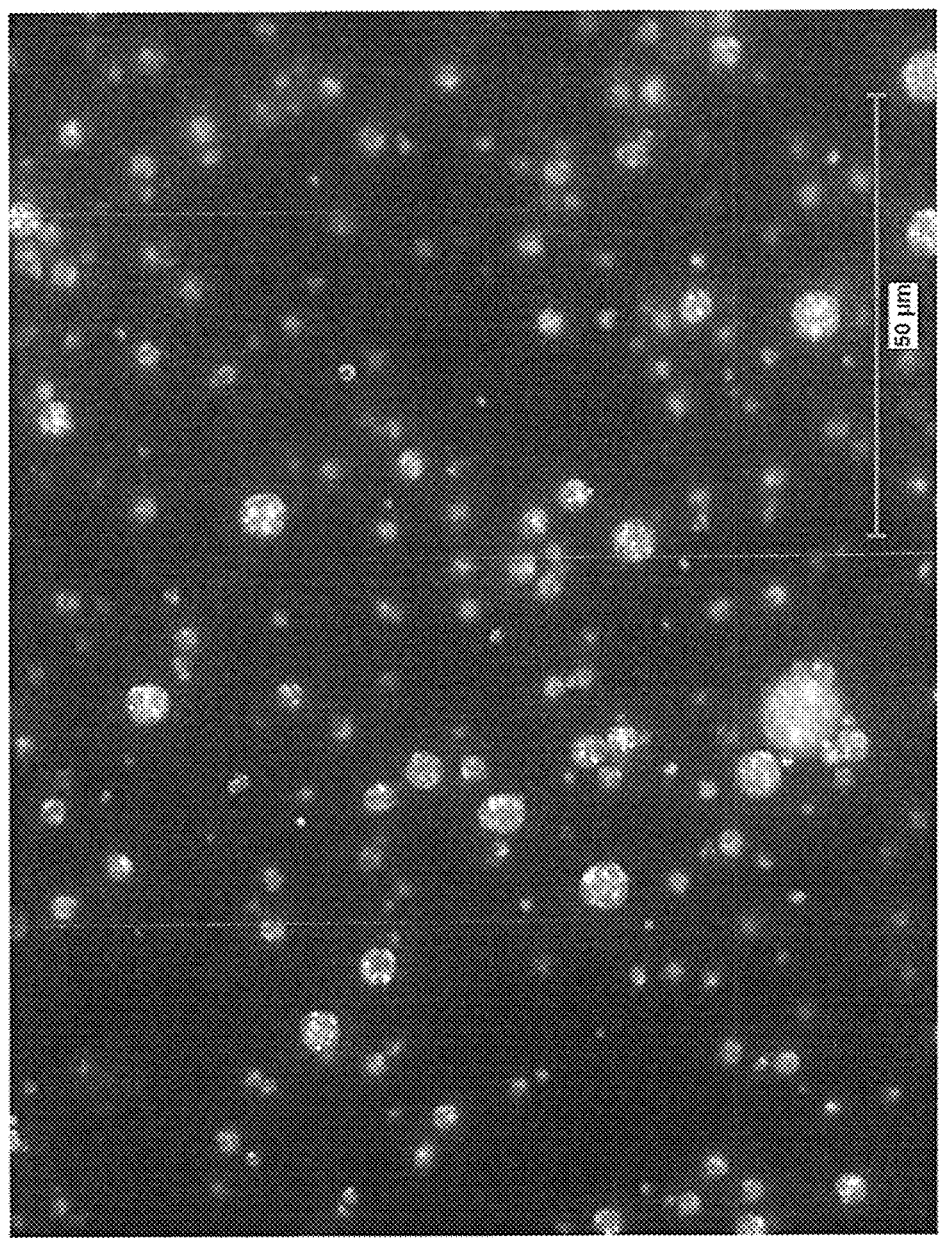
FIG. 18 shows Spray-Dried RX-5902 (1000× magnification, polarized light).

Microscopy showed the presence of crystalline nanoparticles contained in amorphous spherical microparticles as shown in FIG. 17 and FIG. 18. No free crystals or evidence of crystal regrowth was observed, suggesting that no dissolution or precipitation of API was affected by the elevated temperatures of drying.

Example 17: Determination of the Oral Bioavailability of RX-5902 Following Intravenous and Oral Administration In this study, the oral bioavailability of RX-5902 was evaluated in male Sprague-Dawley rats following administration of various formulations. RX-5902 was dosed by intravenous (IV) and oral (PO) routes of administration. Four preparations of powders were received from Particles Sciences (Bethlehem, Pa.) and used to make the dosing solutions: (Preparation A): Unmilled. API (Prepared according to Example 13); (Preparation B) 83% GMP lyophilized (Prepared according to Example 15); (Preparation C) 83% high-energy milled lyophilized (Prepared according to Example 16B); and (Preparation D) 93% spray-dried (Prepared according to Example 16C)

Dose levels for each animal were individually determined based on body weight and amount of test article administered. For each dose, the appropriate amount of formulation powder was weighed, and then 1 mL of the appropriate solvent was added and the total volume was immediately administered, except for the unmilled API where an additional 1 mL of solvent was added and dosed to recover all API remaining in the vial. Following dosing, blood samples were collected up to 24 hours post-dose, and plasma concentrations of the test article was determined by LC-MS/MS. Pharmacokinetic parameters were determined using Phoenix WinNonlin (v6.4).

Following IV dosing at 40.7 mg/kg average dose, RX-5902 (83% GMP Lyophilized Cake; Group 2) had an average half-life of 10.5+2.46 hours. Its average clearance rate was 0.400±0.0263 L/hr/kg. The average volume of distribution was 5.60±1.30 L/Kg.

Following PO dosing of unmilled RX-5902 (Unmilled API in 0.36% Poloxamer 407 in ultrapure water; Group 1) at 68 mg/kg average dose, maximum plasma concentrations (average of 743±199 ng/mL) were observed between 2 and 4 hours post dosing. The average half-life could not be determined; however, the half-life was 3.29 hours for Rat #576. The average exposure based on the dose normalized AUCLast was 151±25.2 hr*kg*ng/mL/mg. The average oral bioavailability for unmilled RX-5902 (also referred to herein as "Unmilled API") was 7.62±1.27% at an average dose of 68 mg/kg.

Following PO dosing of lyophilized RX-5902 (83% GMP Lyophilized Cake: Group 3) at 65.9 mg/kg average dose, maximum plasma concentrations (average of 2027±359 ng/mL) were observed at 2 hours post dosing. The average half-life was 9.70 hours. The average exposure based on the dose normalized AUCLast was 360±129 hr*kg*ng/mL/mg. The average oral bioavailability for RX-5902 (83% GMP Lyophilized Cake) was 18.2±6.53% at an average dose of 65.9 mg/kg.

Following PO dosing of high-energy milled lyophilized RX-5902 (83% High-Energy Milled Lyophilized Cake; Group 4) at 65.9 mg/kg average dose, maximum plasma concentrations (average of 2613±692 ng/mL) were observed at 2 hours post dosing. The average half-life was 7.99 hours. The average exposure based on the dose normalized AUCLast was 456±45.9 hr*kg*ng/mL/mg. The average oral bioavailability for RX-5902 (83% High-Energy Milled Lyophilized Cake) was 23.0±2.32% at an average dose of 65.9 mg/kg.

Following PO dosing of Poloxamer spray dried RX-5902 [93% Spray Dried Cake (SDM)+0.23% Poloxamer 407; Group 5] at 66.2 mg/kg, maximum plasma concentrations (average 1270±185 ng/mL) were observed between 2 and 4 hours post dosing. The average half-life could not be determined; however, the half-life was 3.11 hours for Rat#588. The average exposure based on the dose normalized $AUC_{last}$ was 200±33.8 hr*kg*ng/mL/mg. The average oral bioavailability for RX-5902 (93% Spray Dried Cake (SDM)+0.23% Poloxamer 407) was 10.1±1.71% at an average dose of 66.2 mg/kg.

Following PO dosing of Poloxamer-free spray dried RX-5902 [93% Spray Dried Cake (SDM); Group 6] at 65.6 mg/kg, maximum plasma concentrations (average of 1527±627 ng/mL) were observed between 2 and 4 hours post dosing. The average half-life could not be determined; however, the half-life was 6.89 hours for Rat#589. The average exposure based on the dose normalized $AUC_{last}$ was 293±107 hr*kg*ng/mL/mg. The average oral bioavailability for RX-5902 (93% Spray Dried Cake (SDM) was 14.8±5.40% at an average dose of 65.6 mg/kg.

Oral dosing of high-energy milled lyophilized RX-5902 in Group 4 (83% High-Energy Milled Lyophilized Cake) had the highest oral bioavailability with an average of 23%. The overall rank order of oral bioavailability is Group 4 (83% High-Energy Milled Lyophilize Cake)>Group 3 (83% GMP Lyophilized Cake)>Group 6 [93% Spray Dried Cake (SDM)]>Group 5 [93% Spray Dried Cake (SDM)+0.23% Poloxamer 407]>Group 1 (Unmilled API in 0.36% Poloxamer 407 in ultrapure water). The oral bioavailability of differently nanoformulated materials of RX-5902 is shown in Table 9.

TABLE 9

Oral Bioavailability of Different Nanoformulated Materials of RX-5902

| Group | Material | Oral bio-availability (F) |
|---|---|---|
| 1 | Unmilled API (Preparation A) Dissolved in 0.36% Poloxamer 407 Solution (RX-5902 17.7 mg, 3.6 mg Poloxamer 407) PO Administration | 7.62 ± 1.27% |
| 2 | Low-energy Milled Lyophilized Powder (Preparation B) Dissolved in Water (RX-5902 10.6 mg, 2.1 mg Poloxamer 407) IV Administration | n/a |

TABLE 9-continued

Oral Bioavailability of Different Nanoformulated Materials of RX-5902

| Group | Material | Oral bio-availability (F) |
|---|---|---|
| 3 | Low-energy Milled Lyophilized Powder (Preparation B) Dissolved in Water (RX-5902 17.5 mg, 3.6 mg Poloxamer 407) PO Administration | 18.2 ± 6.53% |
| 4 | High-energy Milled Lyophilized Powder (Preparation C) Dissolved in Water (RX-5902 17.4 mg, 3.6 mg Poloxamer 407) PO Administration | 23.0 ± 2.32% |
| 5 | High-energy Milled Spray-dried Powder (Preparation D) Dissolved in 0.23% Poloxamer 407 Solution (RX-5902 17.5 mg, 3.6 mg Poloxamer 407) PO Administration | 10.1 ± 1.71% |
| 6 | High-energy Milled Spray-dried Powder (Preparation D) Dissolved in Water (RX-5902 17.4 mg, 1.3 mg of Poloxamer 407) PO Administration | 14.8 ± 5.40% |

For reference, the average oral bioavailability for RX-5902 (nanomilled suspension) in fasted male and female dogs was 29.4% and 21.4%, respectively.

Example 18: RX-5902 API and Regioisomer Impurity

Summary:

A comparison of the analytical data for RX-5902 with the RRT 0.975 Impurity was performed. The analytical data consisted of $^1$H, $^{19}$F, $^{13}$C NMR, UV-Vis absorbance, and mass spectrometry (by LC-MS). All available analytical data strongly suggests that the RRT 0.975 Impurity is a regioisomer of RX-5902.

Background:

In some earlier batches of RX-5902, it was discovered that an unknown impurity was not resolved completely from the main product peak as analyzed using the HPLC method. A new HPLC method was developed which was able to resolve the unknown impurity ("RRT 0.975 Impurity") from the main RX-5902 product peak.

In order to determine the identity of the RRT 0.975 Impurity, 15 grams of a production batch of RX-5902 was separated using supercritical fluid chromatography (SFC). A RX-5902 fraction and RRT 0.975 Impurity fraction were obtained. Using the new HPLC method with the Synergi HydroRP column, the RX-5902 fraction was analyzed and found to be 97.7 area % of RX-5902 with a major impurity of 1.5 area %. The RRT 0.975 Impurity fraction was also analyzed and found to be 79.0 area % of the RRT 0.975 Impurity with 0.7 area % of RX-5902; there were, also 4 impurities each >1 area %.

$^1$H, $^{19}$F, $^{13}$C NMR Data $^1$H and $^{19}$F spectra were obtained on the RX-5902 fraction and the RRT 0.975 Impurity fraction. The $^{13}$C NMR spectrum was obtained on only the RRT 0.975 Impurity fraction and compared with the $^{13}$C NMR spectrum of a previous RX-5902 reference standard lot.

Based on an earlier synthetic step which likely generated a regioisomeric intermediate, it is speculated that the RRT 0.975 Impurity is also the regioisomer of RX-5902, whereby the fluorine atom is on the adjacent aromatic carbon. RX-5902 has the molecular formula $C_{22}H_{24}FN_5O_4$.

Proposed Structure for RRT 0.975 Impurity

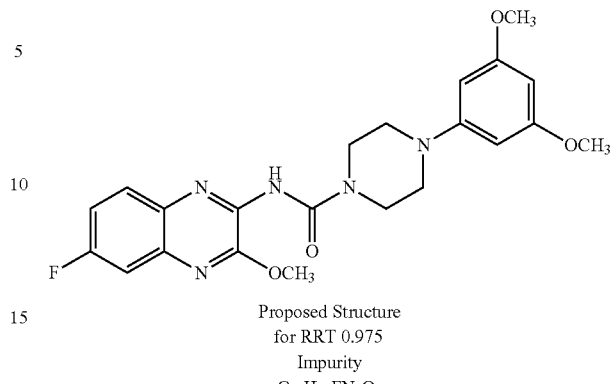

Proposed Structure
for RRT 0.975
Impurity
$C_{22}H_{24}FN_5O_4$
Mol. Wt.: 441.46

Figure 19:
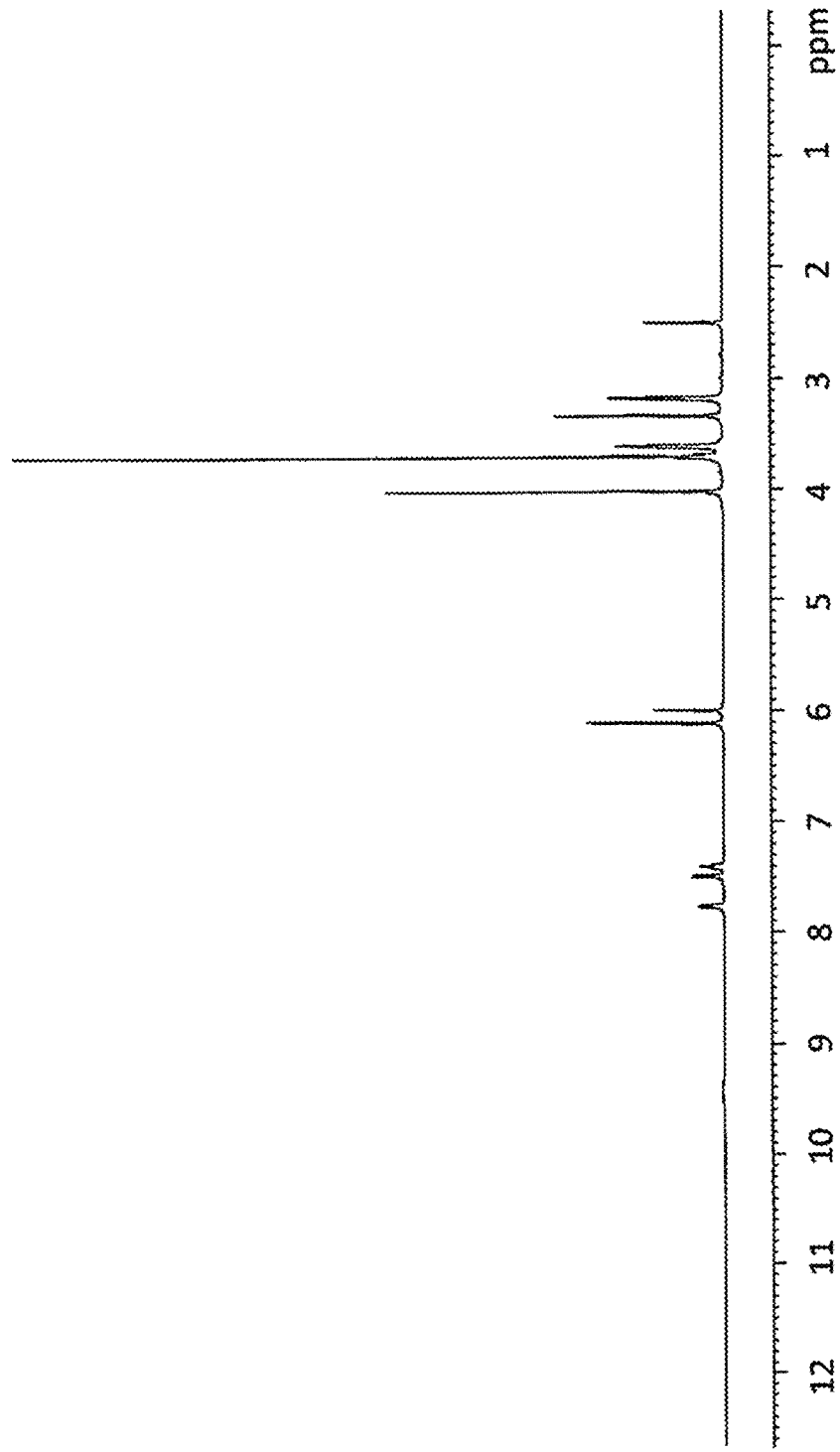
FIG. 19 shows $^1$H NMR spectrum of RX-5902.
Figure 20:
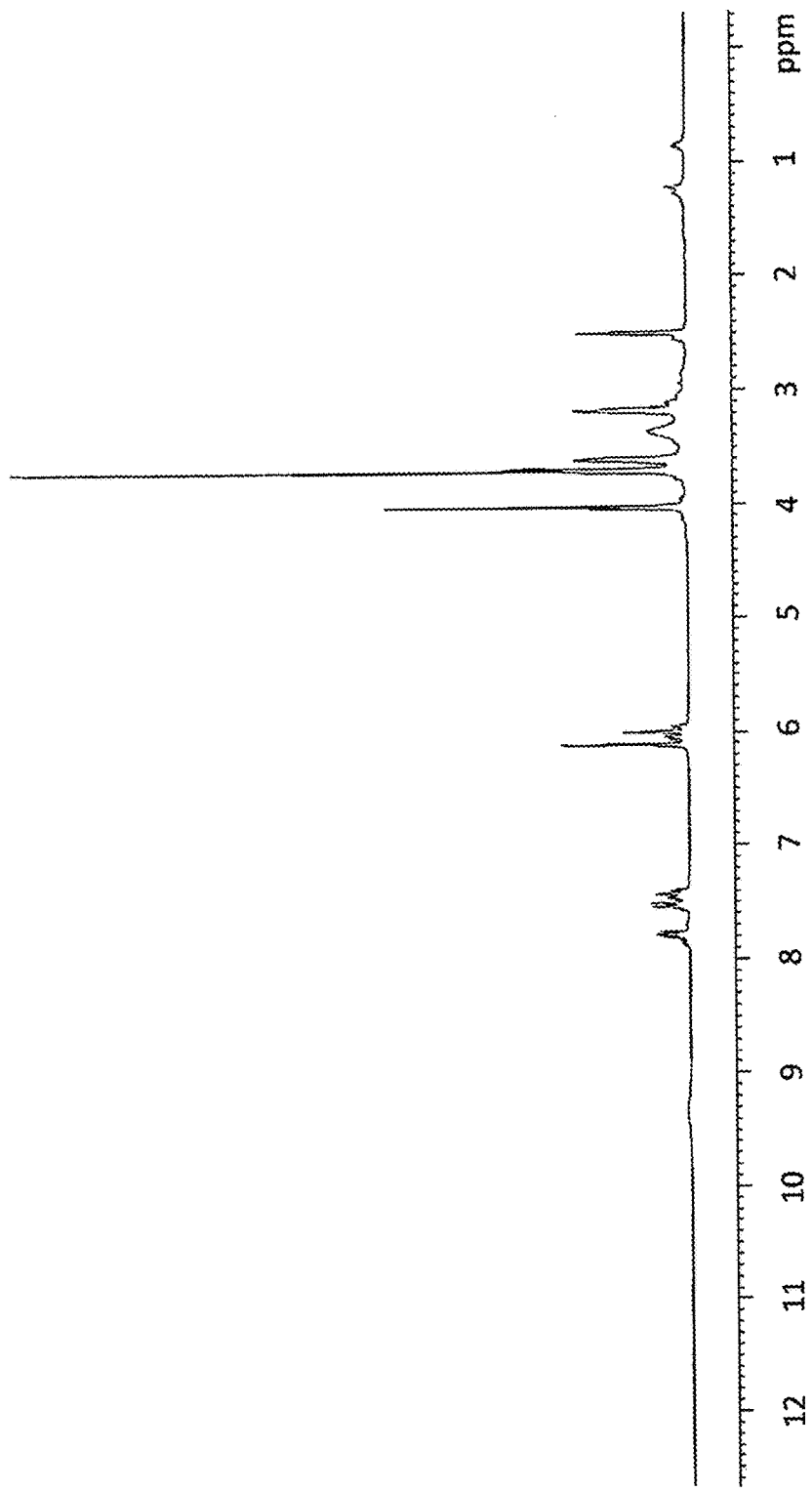
FIG. 20 shows $^1$H NMR spectrum of RRT 0.975 Impurity.
Figure 21:
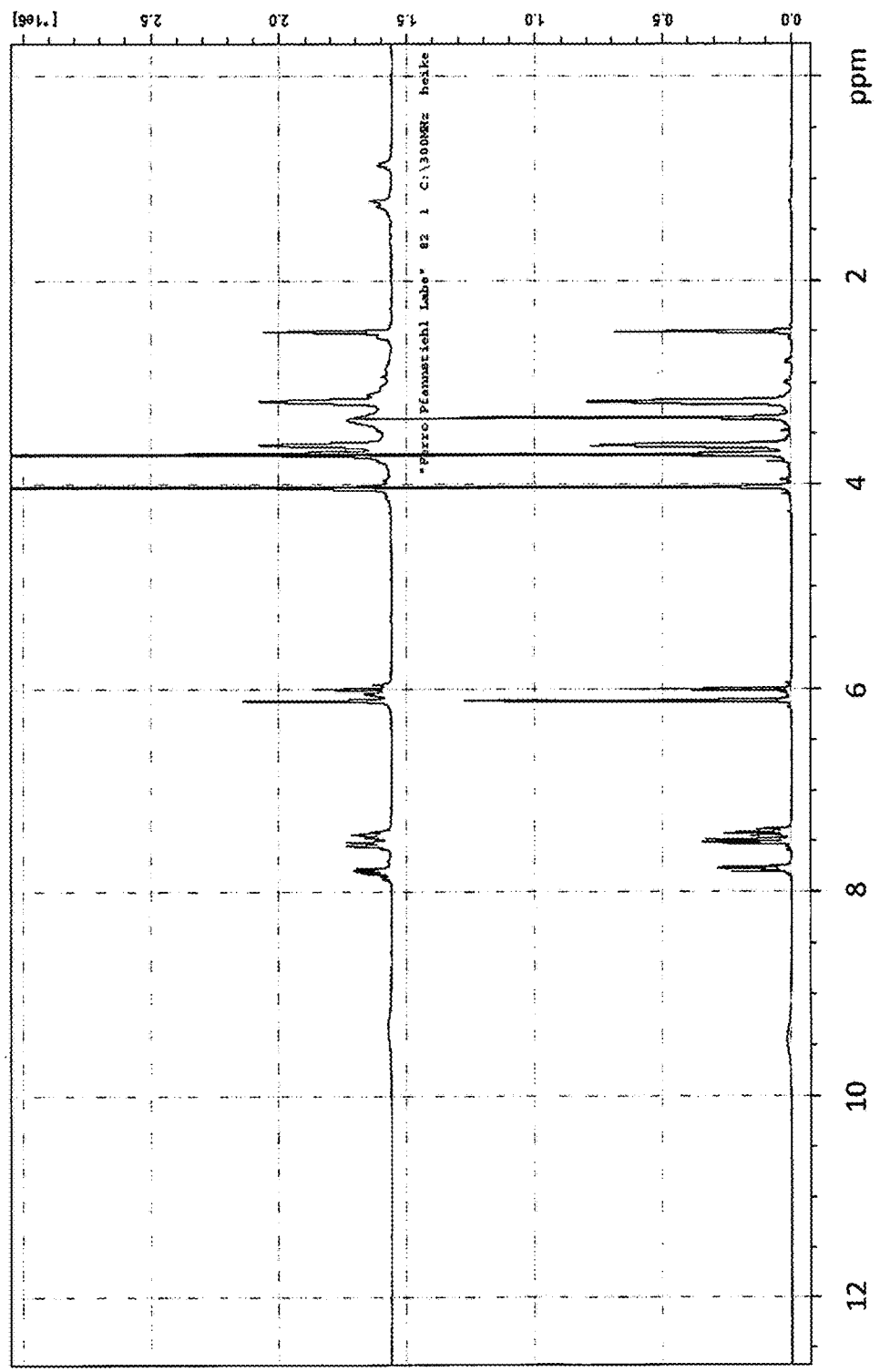
FIG. 21 shows overlay of $^1$H NMR spectra of RRT 0.975 Impurity (top) and RX-5902 (bottom).
Figure 22:
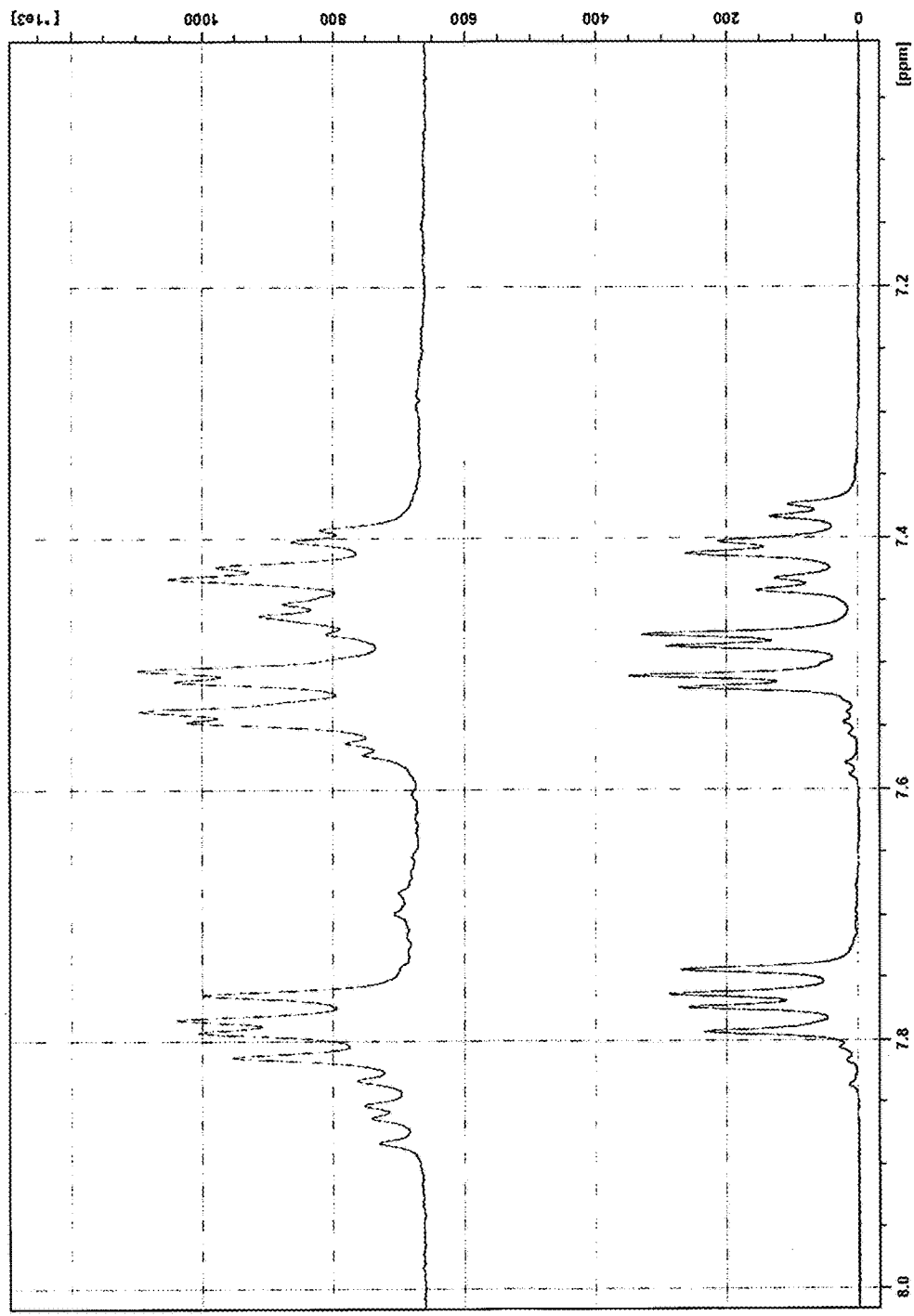
FIG. 22 shows overlay of 7.0-8.0 ppm region of $^1$H NMR spectra of RRT 0.975 Impurity (top plot) and RX-5902 (bottom plot).

FIG. 19 shows $^1$H NMR spectrum of RX-5902; FIG. 20 shows $^1$H NMR spectrum of RRT 0.975 Impurity; FIG. 21 shows overlay of $^1$H NMR spectra of RRT 0.975 Impurity (top) and RX-5902 (bottom); and FIG. 22 shows overlay of 7.0-8.0 ppm region of $^1$H NMR spectra of RRT 0.975 Impurity (top plot) and RX-5902 (bottom plot).

It can be seen that the two $^1$H NMR spectra are very similar (especially the splitting patterns), with minor chemical shifts observed for the signals in the 7.0-8.0 ppm region, and this observation strongly suggests that the RRT 0.975 Impurity is a regioisomer of RX-5902.

Figure 23:
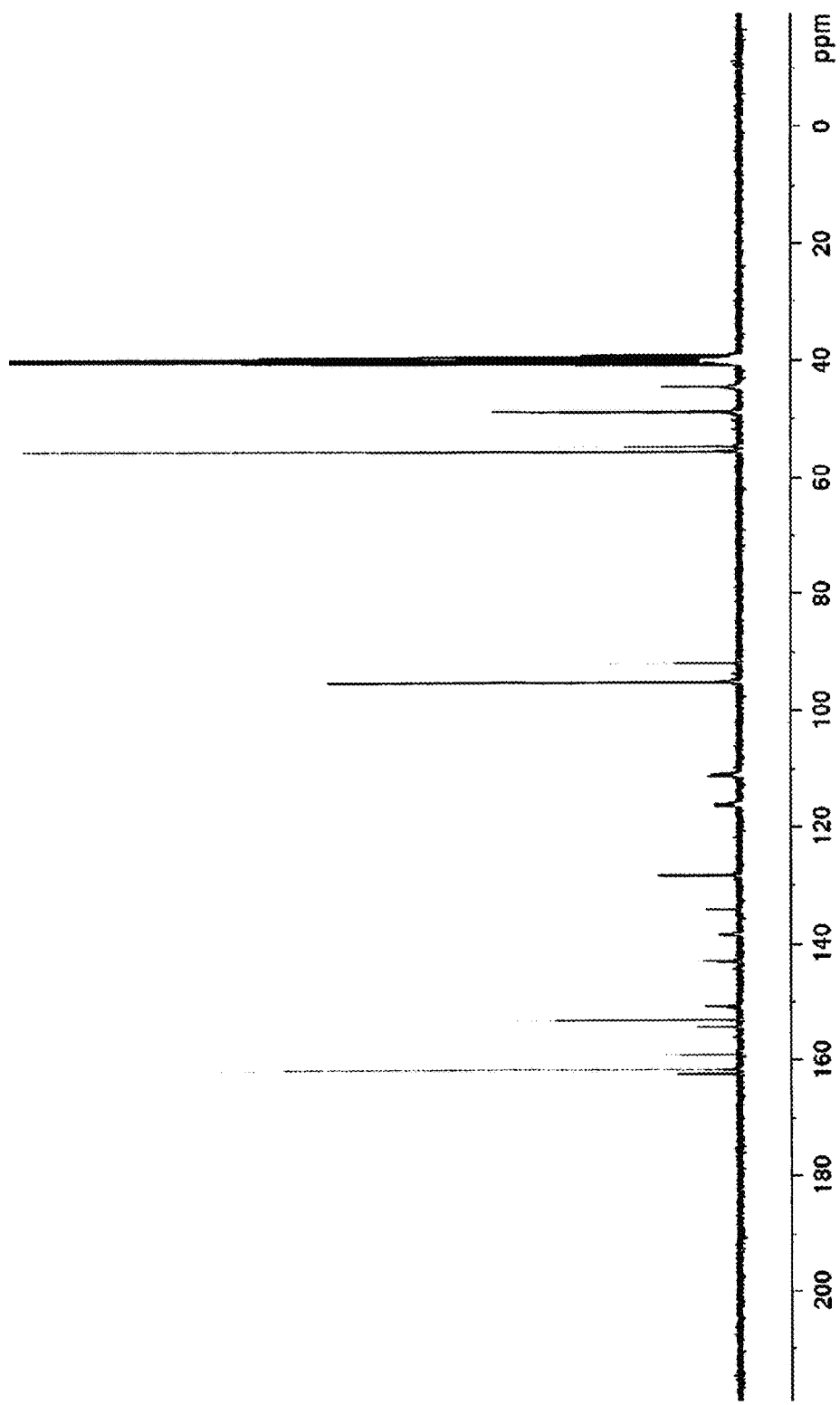
FIG. 23 shows $^{13}$C NMR spectrum RX-5902.
Figure 24:
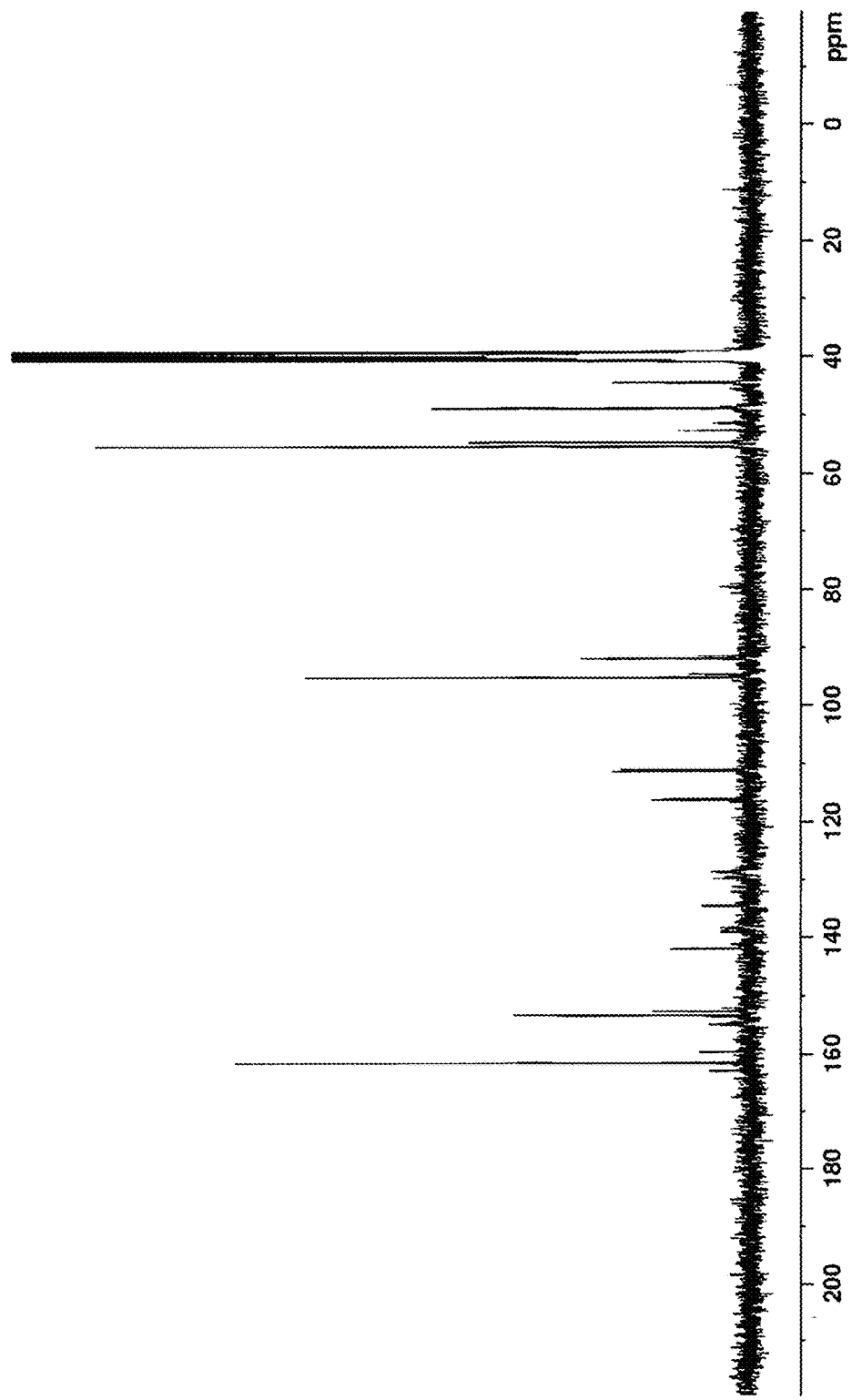
FIG. 24 shows $^{13}$C NMR spectrum of RRT 0.975 Impurity.
Figure 25:
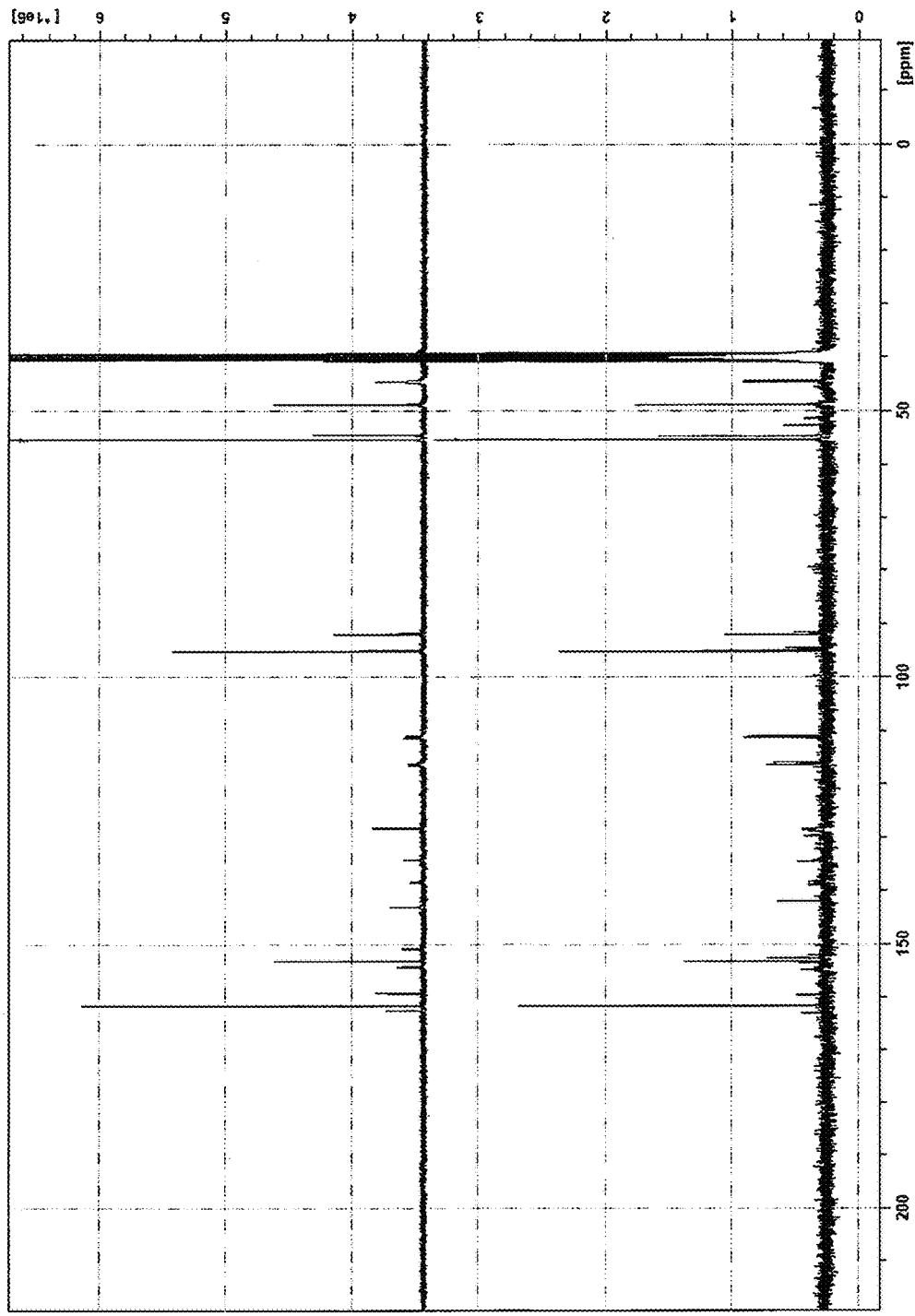
FIG. 25 shows overlay of $^{13}$C NMR spectra of RX-5902 (top plot) and RRT 0.975 Impurity (bottom plot).
Figure 26:
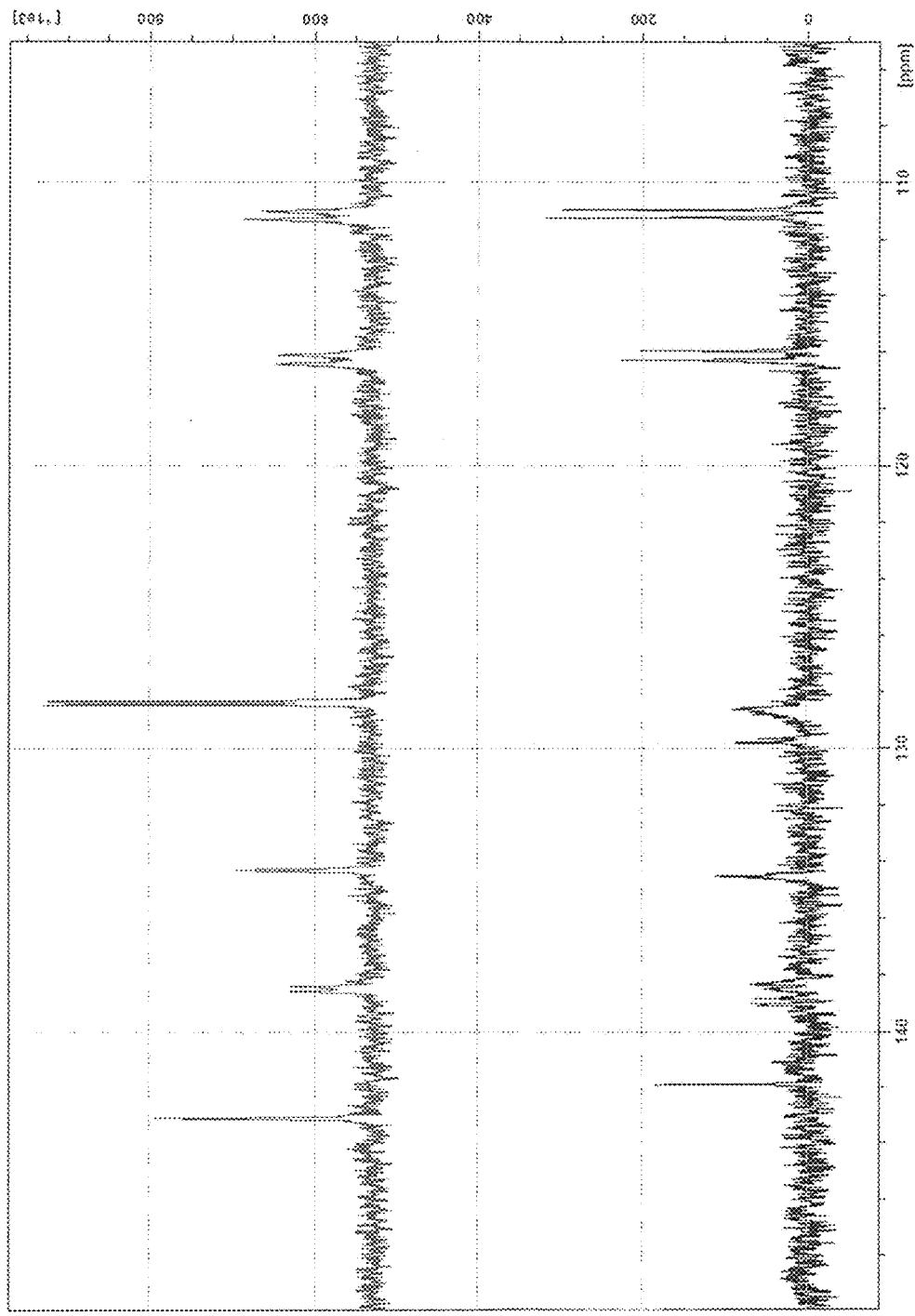
FIG. 26 shows of 108-150 ppm region of $^{13}$C NMR spectra of RX-5902 (top plot) and RRT 0.975 Impurity (bottom plot).

FIG. 23 shows $^{13}$C NMR spectrum of RX-5902; FIG. 24 shows $^{13}$C NMR spectrum of RRT 0.975 Impurity; FIG. 25 shows overlay of $^{13}$C NMR spectra of RX-5902 (top plot) and RRT 0.975 Impurity (bottom plot); and FIG. 26 shows of 108-150 ppm region of $^{13}$C NMR spectra of RX-5902 (top plot) and RRT 0.975 Impurity (bottom plot).

It can be seen that the two $^{13}$C NMR spectra are very similar, which strongly supports the possibility that the RRT 0.975 Impurity is a regioisomer of RX-5902.

Figure 27:
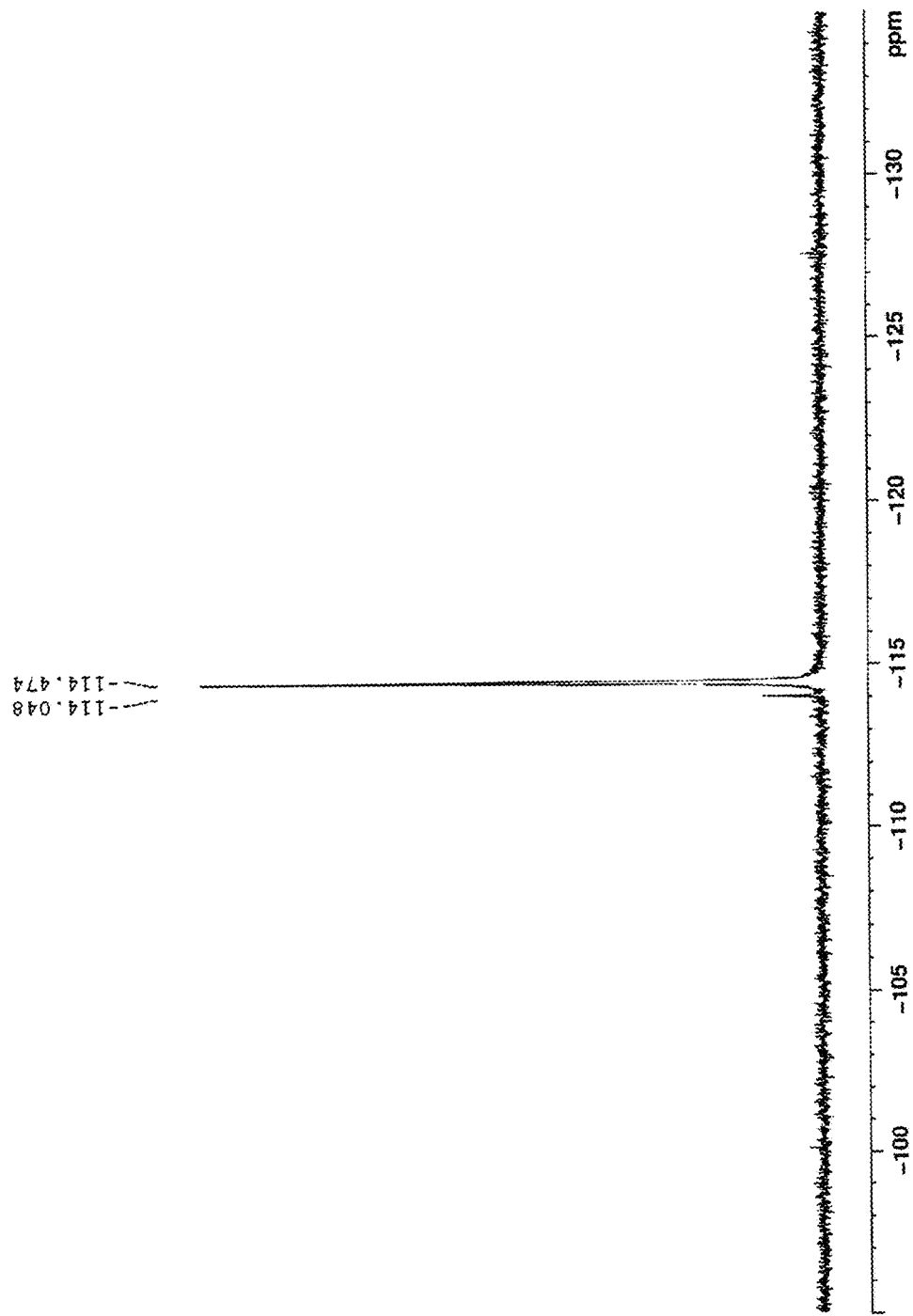
FIG. 27 shows $^{19}$F NMR spectrum of RX-5902.
Figure 28:
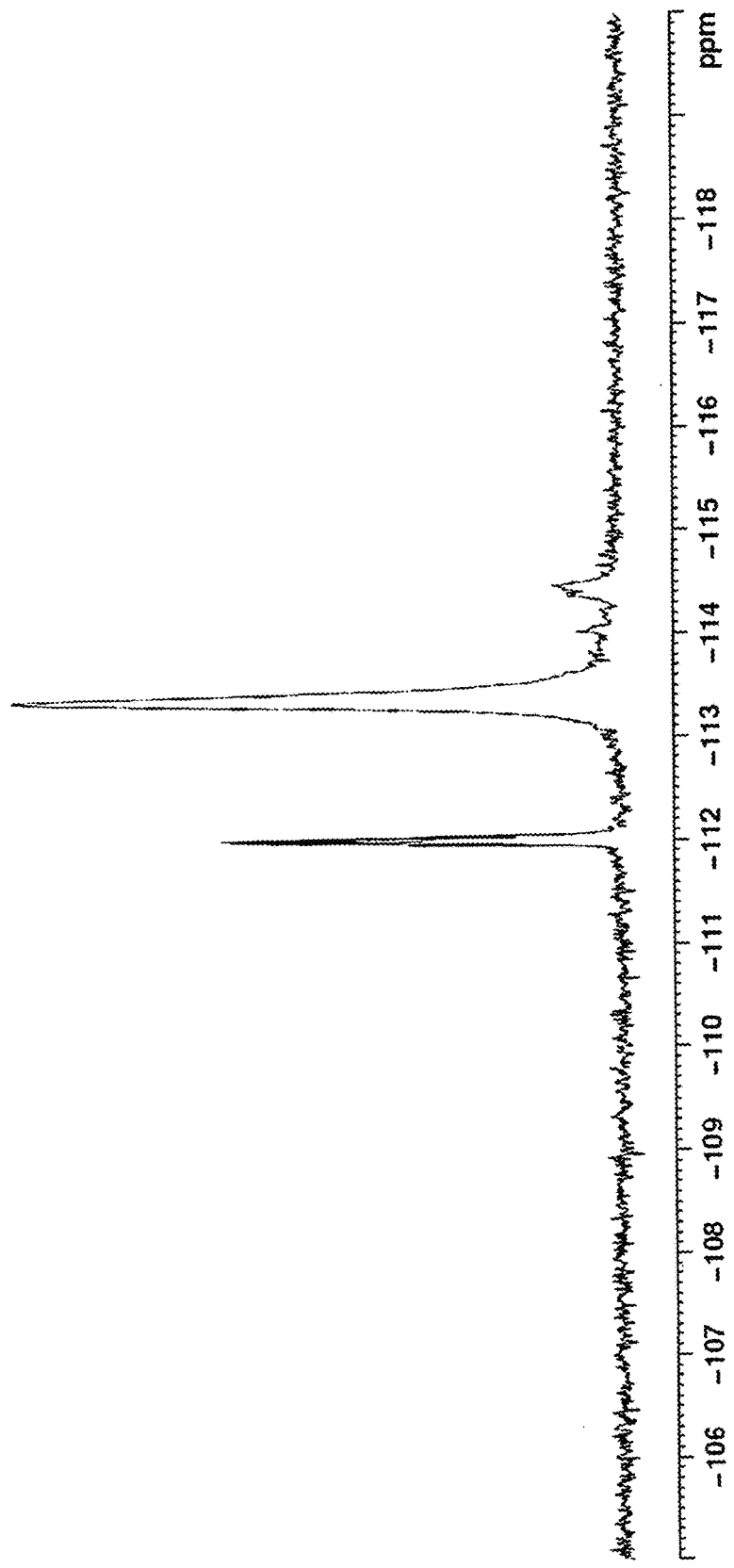
FIG. 28 shows $^{19}$F NMR spectrum of RRT 0.975 Impurity.

FIG. 27 shows $^{19}$F NMR spectrum of RX-5902; FIG. 28 shows $^{19}$F NMR spectrum of RRT 0.975 Impurity.

As shown in FIGS. 27 and 28, the two $^{19}$F NMR spectra are quite different. The $^{19}$F chemical shift is −114.5 ppm for RX-5902 while it is −112.0 ppm (appearing as a quartet) for the RRT 0.975 Impurity. This indicates that the fluorine atom is in a slightly different environment and again strongly supports the possibility that the RRT 0.975 Impurity is a regioisomer of RX-5902.

UV-Vis Absorbance Data

Figure 29:
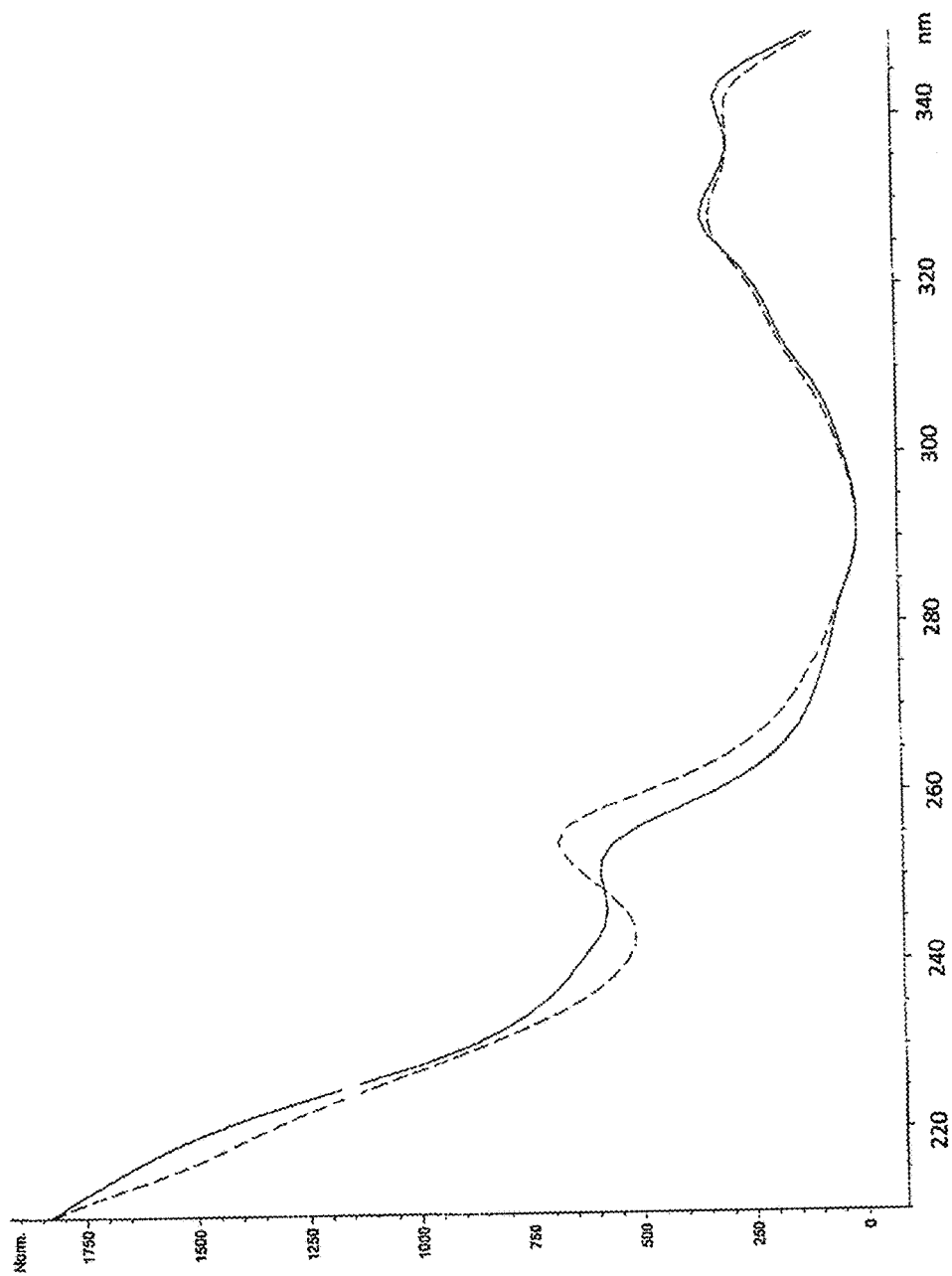
FIG. 29 shows UV-Vis absorbance data of RX-5902 (solid line) and the RRT 0.975 Impurity (dashed line).

UV-Vis absorbance data was gathered on a production batch of RX-5902 separated using the same HPLC method. As shown in FIG. 29, the graph indicates that both RX-5902 (solid line) and the RRT 0.975 Impurity (dashed line) have very similar absorbance spectra. This again strongly supports the possibility that the RRT 0.975 Impurity is a regioisomer of RX-5902.

LC-MS Data

Figure 30:
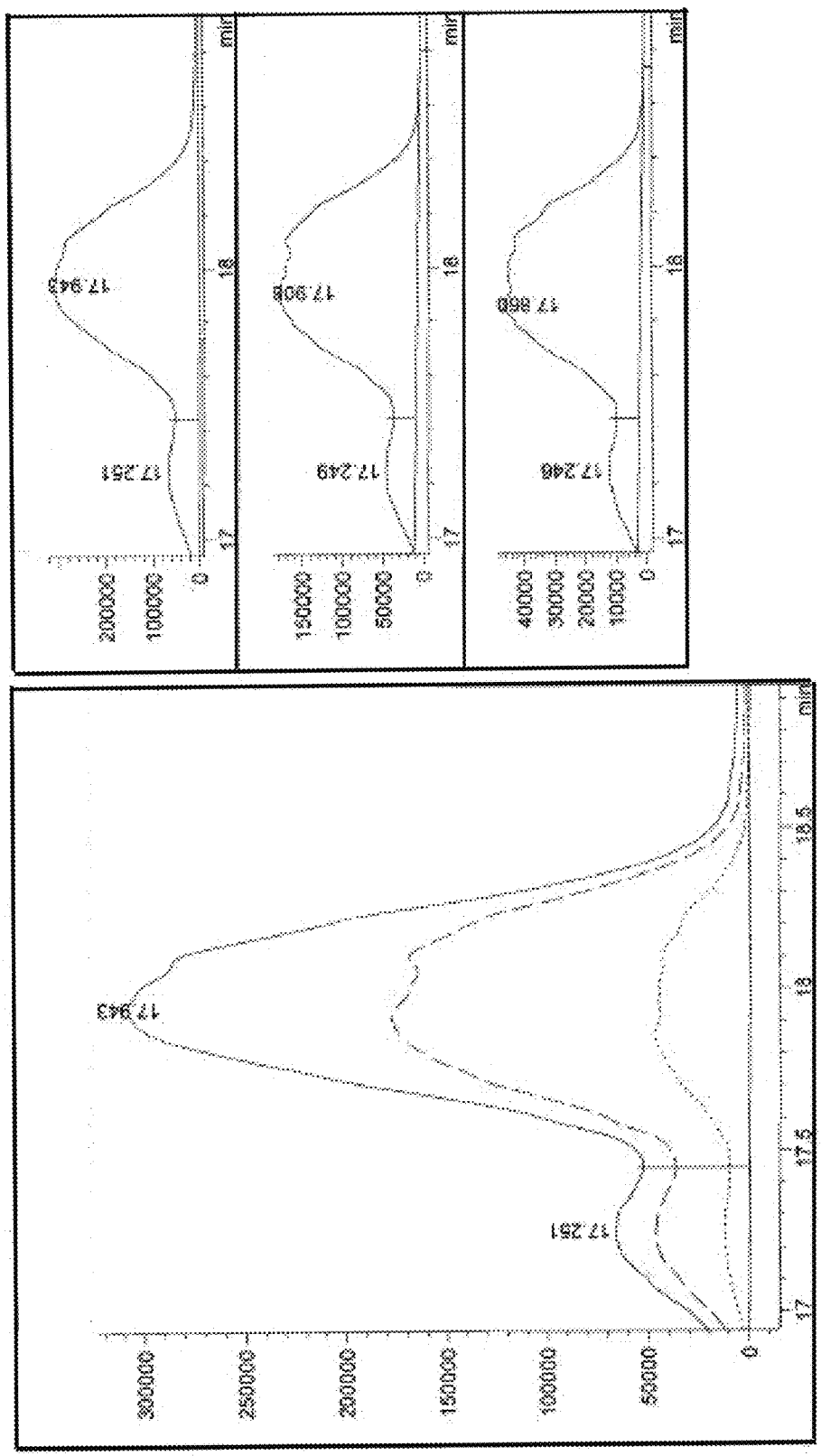
FIG. 30 shows Liquid Chromatography-Mass Spectrometry (LC-MS) of 17.9 min peak corresponding to the main RX-5902 product.
Figure 31:
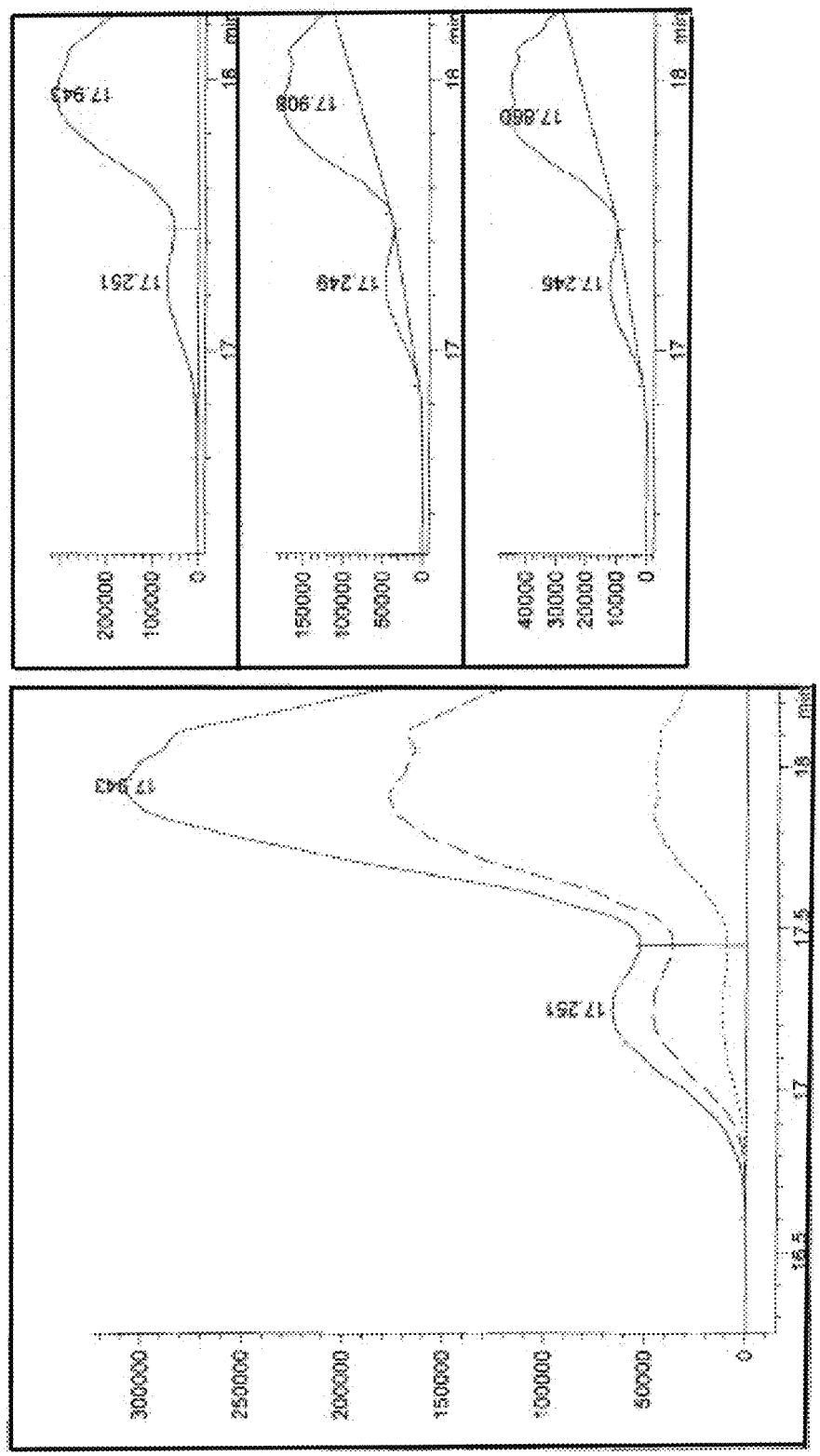
FIG. 31 shows LC-MS of 17.2 min peak corresponding to the RRT 0.975 Impurity.

FIG. 30 shows LC-MS of 17.9 min peak corresponding to the main RX-5902 product (the graph on the left overlaps of the three graphs from the right); FIG. 31 shows LC-MS of 17.2 min peak corresponding to the RRT 0.975 Impurity (the graph on the left overlaps of the three graphs from the right); and FIG. 32 shows LC-MS data indicating that both RX-5902 and the RRT 0.975 Impurity have the exact [M+Na]$^+$ mass of 464, again supporting the conclusion that the RRT 0.975 Impurity is a regioisomer of RX-5902.

Conclusion:

A comparison of the analytical data (consisting of $^1$H, $^{19}$F, $^{13}$C NMR, UV-Vis absorbance, and mass spectrometry) strongly indicate that the RRT 0.975 Impurity is a regioisomer of RX-5902.

Example 19: X-Ray Crystal Structure of RX-5902

Method of Analysis

The single crystal X-ray structure of RX-5902 was determined at 100 K in the triclinic, space group P-1 using a crystal as grown. There is one fully ordered API molecule in the asymmetric unit. The final R1 [I>2σ(I)]=4.77%. An XRPD pattern was calculated from the crystal structure, which shows that the single crystal structure is representative of the supplied material.

For XRPD analysis, a PANalytical (X'Pert$^3$ Powder) X-ray powder diffractometer and Si zero background holder were used. The parameters used are listed in Table 10.

TABLE 10

Parameters for XRPD test

| Parameter | Value |
| --- | --- |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.16 |
| Total time (min) | 4 min |

Example 19A XRPD of RX-5902 Nanoformulation

Figure 33:
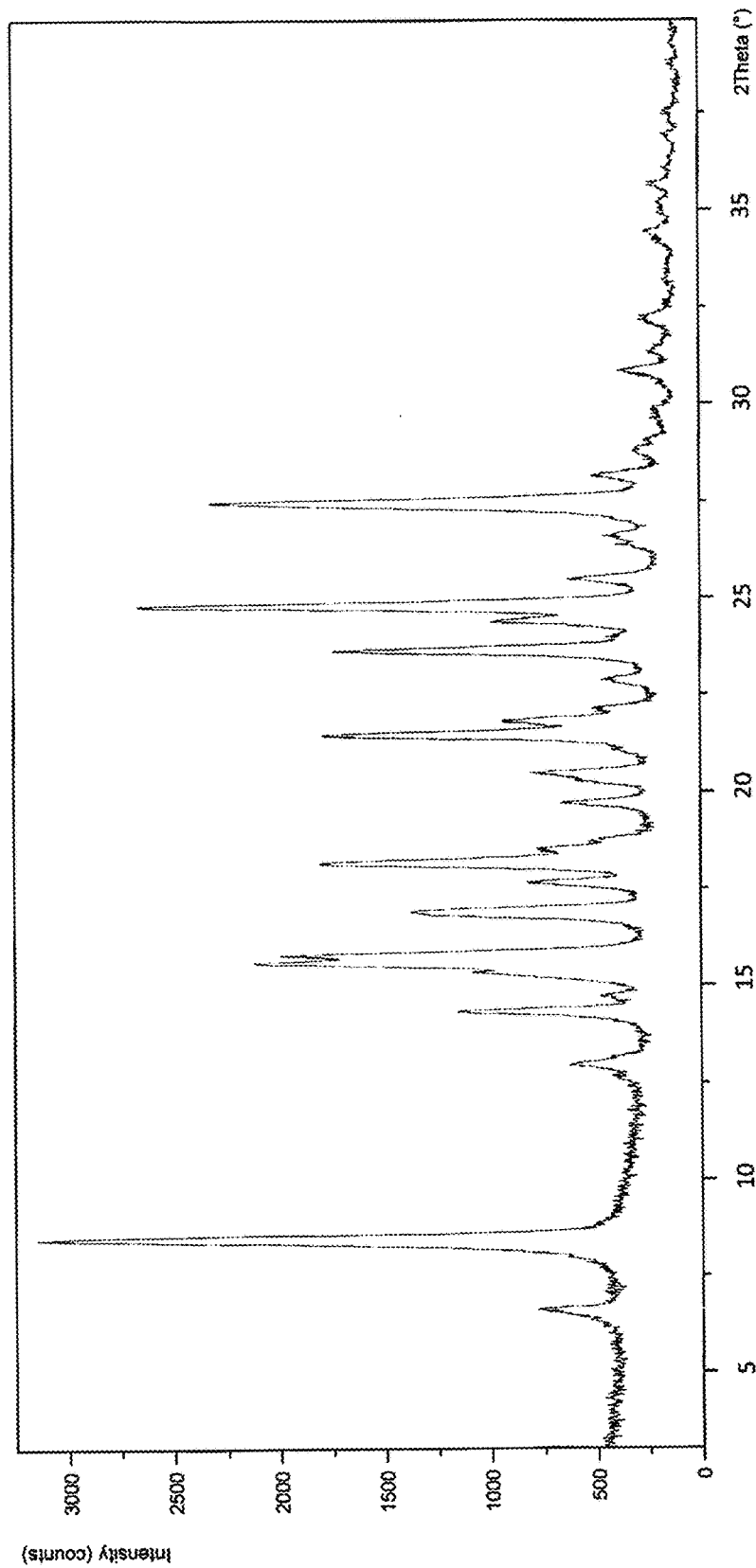
FIG. 33 is an X-Ray Powder Diffraction (XRPD) of crystalline RX-5902 nanoformulation.

The XRPD of particles from a RX-5902 nanoformulation prepared according to the method of Example 16B was determined. As shown in FIG. 33, RX-5902 is crystalline. Detailed XRPD peak identification are found in Table 11.

TABLE 11

XRPD peak selection of RXN1490A-001-4 (B004194-12-A)

| Pos. [°2Th.] | Height [cts] | FWHM Left [°2Th.] | d-spacing [Å] | Rel. Int. [%] |
| --- | --- | --- | --- | --- |
| 6.642046 | 348.056300 | 0.230256 | 13.30800 | 15.42 |
| 8.558004 | 2079.155000 | 0.204672 | 10.33244 | 92.11 |
| 12.968890 | 320.995500 | 0.127920 | 6.82647 | 14.22 |
| 14.346660 | 876.465800 | 0.102336 | 6.17385 | 38.83 |
| 14.753260 | 178.574600 | 0.102336 | 6.00460 | 7.91 |
| 15.328680 | 765.607200 | 0.153504 | 5.78046 | 33.92 |
| 15.574780 | 1790.413000 | 0.153504 | 5.68967 | 79.32 |
| 15.850830 | 1411.945000 | 0.102336 | 5.59121 | 62.55 |
| 16.970760 | 1003.171000 | 0.281424 | 5.22467 | 44.44 |
| 17.671800 | 539.593000 | 0.153504 | 5.01896 | 23.90 |
| 18.141790 | 1518.727000 | 0.076752 | 4.88998 | 67.28 |
| 18.544620 | 513.062700 | 0.102336 | 4.78466 | 22.73 |
| 19.727840 | 402.150200 | 0.153504 | 4.50028 | 17.82 |
| 20.506980 | 529.090300 | 0.089544 | 4.33102 | 23.44 |
| 21.479630 | 1569.747000 | 0.051168 | 4.13705 | 69.54 |
| 21.837050 | 709.123000 | 0.102336 | 4.07014 | 31.41 |
| 22.167590 | 269.386500 | 0.127920 | 4.01019 | 11.93 |
| 22.923880 | 215.980500 | 0.204672 | 3.87957 | 9.57 |
| 23.658390 | 1493.694000 | 0.115128 | 3.76076 | 66.17 |
| 24.417090 | 761.980500 | 0.102336 | 3.64560 | 33.76 |
| 24.852430 | 2257.320000 | 0.191880 | 3.58272 | 100.00 |
| 25.533150 | 377.178100 | 0.102336 | 3.48872 | 16.71 |
| 26.636410 | 222.121300 | 0.153504 | 3.34668 | 9.84 |
| 27.474790 | 2110.269000 | 0.153504 | 3.24643 | 93.49 |
| 28.174960 | 326.430600 | 0.179088 | 3.16733 | 14.46 |
| 28.796790 | 137.265100 | 0.153504 | 3.10033 | 6.08 |
| 29.856940 | 54.482390 | 0.153504 | 2.99262 | 2.41 |
| 30.860610 | 212.309100 | 0.153504 | 2.89754 | 9.41 |
| 31.366870 | 81.582460 | 0.153504 | 2.85192 | 3.61 |
| 32.276590 | 111.028900 | 0.281424 | 2.77359 | 4.92 |
| 34.449570 | 122.052000 | 0.153504 | 2.60345 | 5.41 |
| 35.664690 | 93.923380 | 0.204672 | 2.51749 | 4.16 |
| 36.904290 | 45.109600 | 0.153504 | 2.43572 | 2.00 |
| 37.463500 | 34.154410 | 0.307008 | 2.40064 | 1.51 |
| 38.747700 | 19.893850 | 0.307008 | 2.32399 | 0.88 |

Example 19B XRPD of RX-5902 API

Figure 34:
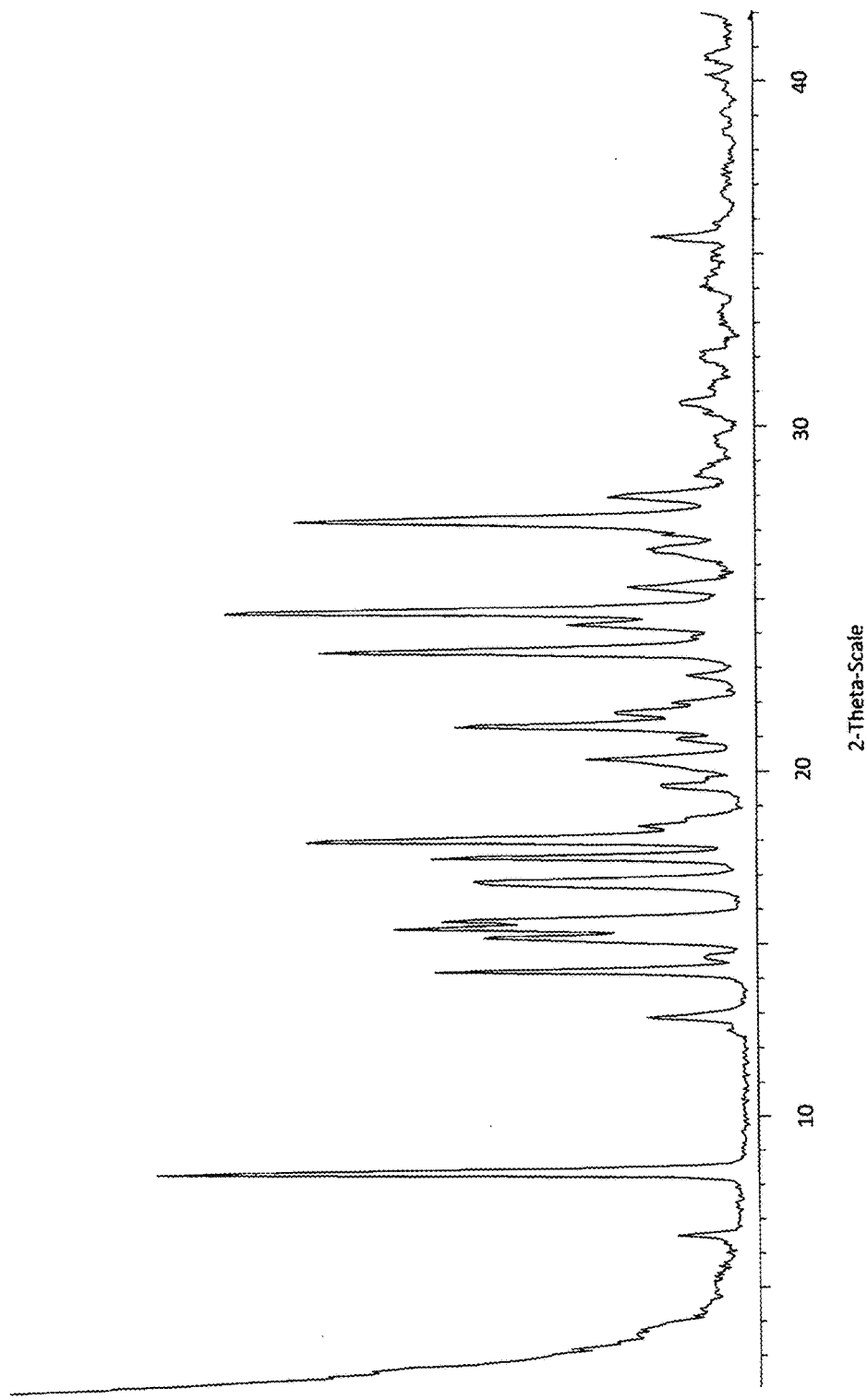
FIG. 34 is a detailed XRPD pattern of RX-5902 API.

FIG. 34 shows XRPD pattern of RX-5902 API prepared according to the method of Example 14.

Example 19B1—Solubility Assessment, Slow Cooling and Slow Evaporation

RX-5902 (ca. 2 mg) was weighed in a 1.5 ml clear glass vials. An aliquot of the corresponding solvent or solvent mixture was added at RT and solubility was assessed after 10 min as shown in Table 12. Solutions and suspensions were then placed into a shaking chamber at 50° C. for 10 more minutes. If no dissolution was observed, another aliquot of solvent was added and samples were placed in the shaking chamber at 50° C. for 10 more minutes. This procedure was repeated until dissolution was achieved or a maximum of 400 vol was added.

TABLE 12

Solubility Assessment of RX-5902

| Solvent | Solubility at RT (mg/ml) | Solubility at 50° C. (mg/ml) | Result after slow cooling | Result after evaporation |
| --- | --- | --- | --- | --- |
| Methanol | <100 | ≥2.5 | Solution | Solution |
| Ethanol | <100 | ≥2.5 | Solution | Suspension, needles |
| Acetone | <100 | ≥12.5 | plate-like crystals | n/a |
| MEK | <100 | ≥12.5 | plate-like crystals | n/a |
| MIBK | <100 | ≥6.25 | Suspension, needles | n/a |
| Ethyl Acetate | <100 | ≥12.5 | plate-like crystals | n/a |
| THF | <100 | ≥25 | Solution | Dry white solid |
| Acetonitrile | <100 | ≥12.5 | plate-like crystals | n/a |
| DMSO | <100 | ≥100 | Solution | Solution |
| Isopropanol-10% water | <100 | ≥2.5 | Solution | Suspension, needles |

Legend: n/a, not applicable

Depending on the results obtained from the solubility assessment samples were treated as follows: (1) solutions obtained at RT were allowed to slowly evaporate at RT by piercing a needle on the vial cap, (2) solutions obtained at 50° C. were cooled at 0.25° C./min to 5° C. Solutions obtained after cooling were allowed to slowly evaporate at RT. Any suspensions obtained with crystals potentially suitable for SCXRD were assessed by PLM microscopy and the most promising crystals were used for SCXRD analyses.

Example 19B2—Single Crystal Structure Determination

Figure 35:
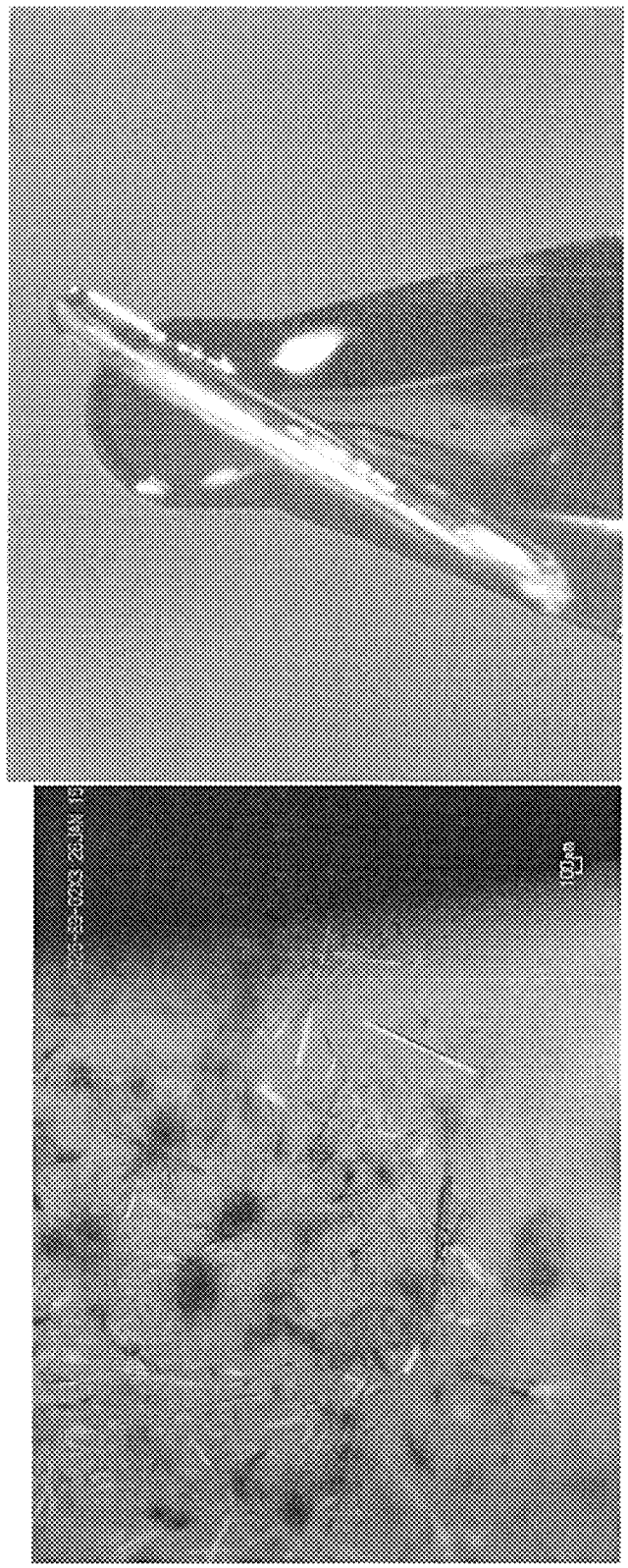
FIGS. 35A and 35B are optical micrograph of the crystalline batch (left) and the crystal (right) used for the XRPD data collection.

Crystals of RX-5209 were crystallized from ethanol by slow evaporation (ca. 2 mg in 400 vol. (0.8 ml) of solvent). The crystals obtained were of needle morphology. A crystal of sufficient size and quality for analysis by single crystal X-ray diffraction was isolated with approximate dimensions 0.650×0.080×0.070 mm. Optical micrographs of the crystals as received and the single crystal used for the data collection are shown in FIGS. 35A and 35B. Parameters and results of the measurement are shown in Tables 13-21.

Crystallographic Tables

TABLE 13

Sample and crystal data.

| | |
|---|---|
| Crystallization solvents | Ethanol |
| Crystallization method | Slow evaporation |
| Empirical formula | $C_{22}H_{24}FN_5O_4$ |
| Formula weight | 441.46 |
| Temperature | 100(2) K |
| Wavelength | 1.54178 Å |
| Crystal size | 0.650 × 0.080 × 0.070 mm |
| Crystal habit | Colorless Needle |
| Crystal system | Triclinic |
| Space group | P−1 |
| Unit cell dimensions | a = 6.7439(3) Å   α = 67.972(5)° |
| | b = 11.4634(5) Å   β = 86.247(4)° |
| | c = 14.5456(8) Å   γ = 86.663(4)° |
| Volume | 1039.48(9) Å3 |
| Z | 2 |
| Density (calculated) | 1.410 Mg/m$^3$ |
| Absorption coefficient | 0.880 mm$^{-1}$ |
| F(000) | 464 |

TABLE 14

Data collection and structure refinement.

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 9.018 to 74.481° |
| Index ranges | −6 ≤ h ≤ 8, −14 ≤ k ≤ 14, −18 ≤ l ≤ 17 |
| Reflections collected | 9202 |
| Independent reflections | 4227 [R(int) = 0.0459] |
| Coverage of independent reflections | 99.4% |
| Variation in check reflections | n/a |
| Absorption correction | Semi-empirical from equivalents |
| Max. and min. transmission | 1.00000 and 0.72908 |
| Structure solution technique | Direct methods |
| Structure solution program | SHELXTL (Sheldrick, 2013) |
| Refinement technique | Full-matrix least-squares on F$^2$ |
| Refinement program | SHELXTL (Sheldrick, 2013) |
| Function minimized | $\Sigma\ w(F_o^2 - F_c^2)^2$ |
| Data/restraints/parameters | 4227/0/296 |
| Goodness-of-fit on F$^2$ | 1.035 |
| $\Delta/\sigma_{max}$ | 0.000 |
| Final R indices | |
| 3240 data; I > 2σ(I) | R1 = 0.0477, wR2 = 0.1257 |
| all data | R1 = 0.0647, wR2 = 0.1397 |
| Weighting scheme | w =1/[σ$^2$ (F$_o^2$) + (0.0750P)$^2$ + 0.1242P] where P = (F$_o^2$ + 2F$_c^2$)/3 |
| Extinction coefficient | n/a |
| Largest diff. peak and hole | 0.249 and −0.273 eÅ-3 |

Refinement Summary:
Ordered Non-H atoms, XYZ Freely refining
Ordered Non-H atoms, U Anisotropic
H atoms (on carbon), XYZ Idealized positions riding on attached atoms
H atoms (on carbon), U Appropriate multiple of U(eq) for bonded atom
H atoms (on hetero atoms), XYZ Freely refining
H atoms (on heteroatoms), U Isotropic
Disordered atoms, OCC No disorder
Disordered atoms, XYZ No disorder
Disordered atoms, U No disorder

TABLE 15

Atomic coordinates and equivalent isotropic atomic displacement parameters, (Å$^2$).

| | x/a | y/b | z/c | U(eq) |
|---|---|---|---|---|
| F1 | 0.33930(18) | 0.50175(11) | −0.12020(9) | 0.0282(3) |
| O1 | 0.23176(18) | 0.04077(12) | 0.47864(10) | 0.0214(3) |
| O2 | −0.31711(18) | 0.09001(12) | 0.30184(10) | 0.0207(3) |
| O3 | 1.02089(19) | 0.70023(13) | 0.38735(10) | 0.0232(3) |
| O4 | 0.6086(2) | 0.87007(13) | 0.10089(11) | 0.0278(3) |
| C1 | 0.2064(3) | 0.42287(17) | −0.05502(14) | 0.0220(4) |
| N1 | 0.1173(2) | 0.26781(14) | 0.21122(12) | 0.0176(3) |
| N2 | −0.2182(2) | 0.19787(14) | 0.13777(12) | 0.0196(3) |
| N3 | −0.0078(2) | 0.15134(14) | 0.37225(12) | 0.0179(3) |
| N4 | 0.2561(2) | 0.25262(14) | 0.40644(11) | 0.0168(3) |
| N5 | 0.4667(2) | 0.47744(14) | 0.36062(11) | 0.0166(3) |
| C2 | 0.0448(3) | 0.38960(18) | −0.09454(14) | 0.0222(4) |
| C3 | −0.0951(3) | 0.31417(18) | −0.02920(14) | 0.0224(4) |
| C4 | −0.0741(3) | 0.27209(16) | 0.07350(14) | 0.0189(4) |
| C5 | −0.1907(2) | 0.16298(16) | 0.23162(14) | 0.0173(3) |
| C6 | −0.0189(2) | 0.19765(16) | 0.27046(13) | 0.0163(3) |
| C7 | 0.0921(3) | 0.30631(16) | 0.11079(14) | 0.0179(3) |
| C8 | 0.2363(3) | 0.38315(17) | 0.04389(14) | 0.0210(4) |
| C9 | 0.1691(2) | 0.14402(16) | 0.42264(13) | 0.0165(3) |
| C10 | 0.1522(2) | 0.37615(16) | 0.37214(13) | 0.0172(3) |
| C11 | 0.2900(2) | 0.47736(16) | 0.30681(13) | 0.0172(3) |
| C12 | 0.5727(2) | 0.35405(16) | 0.38973(14) | 0.0182(4) |
| C13 | 0.4403(2) | 0.24899(17) | 0.45586(13) | 0.0176(3) |
| C14 | 0.5861(2) | 0.58318(16) | 0.31906(13) | 0.0165(3) |
| C15 | 0.7508(2) | 0.59303(16) | 0.37003(13) | 0.0174(3) |
| C16 | 0.8660(2) | 0.69848(17) | 0.33020(14) | 0.0177(3) |
| C17 | 0.8272(3) | 0.79508(17) | 0.24001(14) | 0.0191(4) |
| C18 | 0.6636(3) | 0.78338(17) | 0.19067(14) | 0.0197(4) |
| C19 | 0.5428(2) | 0.68034(17) | 0.22955(14) | 0.0191(4) |
| C20 | −0.4913(2) | 0.05379(18) | 0.26809(15) | 0.0225(4) |
| C21 | 1.1247(3) | 0.8144(2) | 0.35825(17) | 0.0308(5) |
| C22 | 0.7554(3) | 0.95587(19) | 0.04173(15) | 0.0266(4) |

U(eq) is defined as one third of the trace of the orthogonalized $U_{ij}$ tensor.

TABLE 16

Selected bond length, (Å).

| | | | |
|---|---|---|---|
| F1—C1 | 1.364(2) | O1—C9 | 1.227(2) |
| O2—C5 | 1.341(2) | O2—C20 | 1.442(2) |
| O3—C16 | 1.382(2) | O3—C21 | 1.427(2) |
| O4—C18 | 1.370(2) | O4—C22 | 1.434(2) |
| C1—C8 | 1.361(3) | C1—C2 | 1.400(3) |
| N1—C6 | 1.302(2) | N1—C7 | 1.378(2) |
| N2—C4 | 1.386(2) | N3—C6 | 1.378(2) |
| N3—C9 | 1.423(2) | N3—C9 | 1.423(2) |
| N3—H3A | 0.89(3) | N4—C9 | 1.340(2) |
| N4—C10 | 1.465(2) | N4—C13 | 1.466(2) |
| N5—C14 | 1.408(2) | N5—C11 | 1.468(2) |
| N5—C12 | 1.471(2) | C2—C3 | 1.379(3) |
| C3—C4 | 1.401(3) | C4—C7 | 1.412(2) |
| C5—C6 | 1.458(2) | C7—C8 | 1.415(2) |
| C10—C11 | 1.515(2) | C12—C13 | 1.522(2) |
| C14—C19 | 1.395(2) | C14—C15 | 1.408(2) |
| C15—C16 | 1.387(2) | C16—C17 | 1.392(3) |
| C17—C18 | 1.394(2) | C18—C19 | 1.389(2) |

TABLE 17

Selected bond angles, (°).

| | | | |
|---|---|---|---|
| C5—O2—C20 | 116.72(14) | C16—O3—C21 | 117.15(15) |
| C18—O4—C22 | 117.38(15) | C8—C1—F1 | 118.53(17) |
| C8—C1—C2 | 124.02(17) | F1—C1—C2 | 117.44(17) |
| C6—N1—C7 | 116.91(15) | C5—N2—C4 | 116.44(15) |
| C6—N3—C9 | 124.41(14) | C6—N3—H3A | 115.5(19) |
| C9—N3—H3A | 112.2(18) | C9—N4—C10 | 124.08(14) |
| C9—N4—C13 | 118.71(14) | C10—N4—C13 | 113.84(14) |
| C14—N5—C11 | 116.47(14) | C14—N5—C12 | 115.86(13) |
| C11—N5—C12 | 109.99(14) | C3—C2—C1 | 117.99(17) |
| C2—C3—C4 | 120.56(17) | N2—C4—C3 | 119.53(17) |
| N2—C4—C7 | 120.53(17) | C3—C4—C7 | 119.94(17) |
| N2—C5—O2 | 122.67(15) | N2—C5—C6 | 123.22(16) |
| O2—C5—C6 | 114.10(16) | N1—C6—N3 | 122.18(16) |
| N1—C6—C5 | 121.17(17) | N3—C6—C5 | 116.65(15) |

TABLE 17-continued

Selected bond angles, (°).

| | | | |
|---|---|---|---|
| N1—C7—C4 | 121.72(16) | N1—C7—C8 | 118.68(16) |
| C4—C7—C8 | 119.59(17) | C1—C8—C7 | 117.87(17) |
| O1—C9—N4 | 123.90(16) | O1—C9—N3 | 119.09(15) |
| N4—C9—N3 | 117.01(15) | N4—C10—C11 | 110.75(13) |
| N5—C11—C10 | 109.96(14) | N5—C12—C13 | 111.35(14) |
| N4—C13—C12 | 109.79(14) | C19—C14—C15 | 118.87(16) |
| C19—C14—N5 | 121.69(15) | C15—C14—N5 | 119.42(16) |
| C16—C15—C14 | 119.45(16) | O3—C16—C15 | 114.76(16) |
| O3—C16—C17 | 122.84(15) | C15—C16—C17 | 122.39(16) |
| C16—C17—C18 | 117.23(16) | O4—C18—C19 | 114.41(16) |
| O4—C18—C17 | 123.79(16) | C19—C18—C17 | 121.80(17) |
| C18—C19—C14 | 120.23(16) | | |

TABLE 18

Selected torsion angles, (°).

| | | | |
|---|---|---|---|
| C8—C1—C2—C3 | 1.5(3) | F1—C1—C2—C3 | -177.32(16) |
| C1—C2—C3—C4 | -0.3(3) | C5—N2—C4—C3 | -179.49(16) |
| C5—N2—C4—C7 | 0.0(2) | C2—C3—C4—N2 | 179.06(16) |
| C2—C3—C4—C7 | -0.4(3) | C4—N2—C5—O2 | -179.28(15) |
| C4—N2—C5—C6 | -0.2(2) | C20—O2—C5—N2 | -1.6(2) |
| C20—O2—C5—C6 | 179.27(14) | C7—N1—C6—N3 | 178.67(15) |
| C7—N1—C6—C5 | -0.6(2) | C9—N3—C6—N1 | -17.9(3) |
| C9—N3—C6—C5 | 161.39(16) | N2—C5—C6—N1 | 0.6(3) |
| O2—C5—C6—N1 | 179.71(15) | N2—C5—C6—N3 | -178.74(16) |
| O2—C5—C6—N3 | 0.4(2) | C6—N1—C7—C4 | 0.4(2) |
| C6—N1—C7—C8 | 179.72(16) | N2—C4—C7—N1 | 0.0(3) |
| C3—C4—C7—N1 | 179.43(16) | N2—C4—C7—C8 | -179.39(16) |
| C3—C4—C7—C8 | 0.1(3) | F1—C1—C8—C7 | 176.99(15) |
| C2—C1—C8—C7 | -1.8(3) | N1—C7—C8—C1 | -178.41(16) |
| C4—C7—C8—C1 | 1.0(3) | C10—N4—C9—O1 | -156.16(17) |
| C13—N4—C9—O1 | 1.8(3) | C10—N4—C9—N3 | 22.9(2) |
| C13—N4—C9—N3 | -179.15(15) | C6—N3—C9—O1 | -119.92(19) |
| C6—N3—C9—N4 | 61.0(2) | C9—N4—C10—C11 | -147.08(16) |
| C13—N4—C10—C11 | 53.99(19) | C14—N5—C11—C10 | -166.06(14) |
| C12—N5—C11—C10 | 59.55(18) | N4—C10—C11—N5 | -56.42(19) |
| C14—N5—C12—C13 | 165.97(15) | C11—N5—C12—C13 | -59.34(19) |
| C9—N4—C13—C12 | 147.35(16) | C10—N4—C13—C12 | -52.49(19) |
| N5—C12—C13—N4 | 54.67(19) | C11—N5—C14—C19 | -2.4(2) |
| C12—N5—C14—C19 | 129.37(18) | C11—N5—C14—C15 | 176.08(15) |
| C12—N5—C14—C15 | -52.2(2) | C19—C14—C15—C16 | -0.1(2) |
| N5—C14—C15—C16 | -178.61(15) | C21—O3—C16—C15 | -170.41(17) |
| C21—O3—C16—C17 | 9.2(3) | C14—C15—C16—O3 | 178.42(15) |
| C14—C15—C16—C17 | -1.2(3) | O3—C16—C17—C18 | -178.51(16) |
| C15—C16—C17—C18 | 1.0(3) | C22—O4—C18—C19 | -160.61(17) |
| C22—O4—C18—C17 | 19.0(3) | C16—C17—C18—O4 | -179.19(17) |
| C16—C17—C18—C19 | 0.4(3) | O4—C18—C19—C14 | 177.97(16) |
| C17—C18—C19—C14 | -1.6(3) | C15—C14—C19—C18 | 1.5(3) |
| N5—C14—C19—C18 | 179.92(16) | | |

TABLE 19

Anisotropic atomic displacement parameters, (Å²).

| | U11 | U22 | U33 | U23 | U13 | U12 |
|---|---|---|---|---|---|---|
| F1 | 0.0346(6) | 0.0267(6) | 0.0213(6) | -0.0068(5) | 0.0082(5) | -0.0096(5) |
| O1 | 0.0171(6) | 0.0164(6) | 0.0245(7) | -0.0004(5) | 0.0012(5) | -0.0043(5) |
| O2 | 0.0168(6) | 0.0221(7) | 0.0226(7) | -0.0070(5) | 0.0007(5) | -0.0078(5) |
| O3 | 0.0222(6) | 0.0215(7) | 0.0257(7) | -0.0071(5) | -0.0044(5) | -0.0081(5) |
| O4 | 0.0278(7) | 0.0216(7) | 0.0261(7) | 0.0020(5) | -0.0061(6) | -0.0076(5) |
| C1 | 0.0249(9) | 0.0164(9) | 0.0239(9) | -0.0074(7) | 0.0054(7) | -0.0037(7) |
| N1 | 0.0157(6) | 0.0163(7) | 0.0204(7) | -0.0062(6) | 0.0000(6) | -0.0028(5) |
| N2 | 0.0199(7) | 0.0162(7) | 0.0225(8) | -0.0066(6) | -0.0026(6) | -0.0020(6) |
| N3 | 0.0148(6) | 0.0173(7) | 0.0201(7) | -0.0044(6) | -0.0006(6) | -0.0060(5) |
| N4 | 0.0131(6) | 0.0156(7) | 0.0204(7) | -0.0050(5) | -0.0016(5) | -0.0017(5) |
| N5 | 0.0130(6) | 0.0147(7) | 0.0215(7) | -0.0054(6) | -0.0022(5) | -0.0027(5) |
| C2 | 0.0285(9) | 0.0196(9) | 0.0184(8) | -0.0069(7) | -0.0030(7) | 0.0009(7) |
| C3 | 0.0249(9) | 0.0209(9) | 0.0223(9) | -0.0087(7) | -0.0041(7) | 0.0007(7) |
| C4 | 0.0192(8) | 0.0147(8) | 0.0235(9) | -0.0078(7) | -0.0001(7) | -0.0015(6) |
| C5 | 0.0163(8) | 0.0120(8) | 0.0244(9) | -0.0072(6) | -0.0024(7) | -0.0023(6) |

TABLE 19-continued

Anisotropic atomic displacement parameters, (Å²).

|     | U11 | U22 | U33 | U23 | U13 | U12 |
|-----|-----|-----|-----|-----|-----|-----|
| C6  | 0.0158(7)  | 0.0125(8)  | 0.0203(8)  | −0.0055(6) | −0.0007(6) | −0.0022(6) |
| C7  | 0.0188(8)  | 0.0140(8)  | 0.0203(8)  | −0.0060(6) | 0.0000(7)  | −0.0015(6) |
| C8  | 0.0201(8)  | 0.0195(9)  | 0.0242(9)  | −0.0091(7) | 0.0022(7)  | −0.0042(7) |
| C9  | 0.0126(7)  | 0.0188(8)  | 0.0169(8)  | −0.0054(6) | 0.0023(6)  | −0.0033(6) |
| C10 | 0.0138(7)  | 0.0157(8)  | 0.0216(8)  | −0.0059(7) | −0.0007(6) | −0.0027(6) |
| C11 | 0.0144(7)  | 0.0156(8)  | 0.0207(8)  | −0.0053(6) | −0.0027(6) | −0.0008(6) |
| C12 | 0.0159(7)  | 0.0147(8)  | 0.0226(9)  | −0.0049(6) | −0.0012(7) | −0.0023(6) |
| C13 | 0.0140(7)  | 0.0183(8)  | 0.0196(8)  | −0.0056(6) | −0.0024(6) | −0.0016(6) |
| C14 | 0.0131(7)  | 0.0166(8)  | 0.0211(8)  | −0.0087(7) | 0.0012(6)  | −0.0017(6) |
| C15 | 0.0158(7)  | 0.0165(8)  | 0.0194(8)  | −0.0063(6) | 0.0013(6)  | −0.0024(6) |
| C16 | 0.0146(7)  | 0.0191(8)  | 0.0226(9)  | −0.0111(7) | −0.0013(6) | −0.0015(6) |
| C17 | 0.0170(7)  | 0.0170(8)  | 0.0225(9)  | −0.0065(7) | 0.0030(7)  | −0.0053(6) |
| C18 | 0.0188(8)  | 0.0182(9)  | 0.0210(9)  | −0.0058(7) | −0.0014(7) | −0.0007(6) |
| C19 | 0.0151(7)  | 0.0193(9)  | 0.0233(9)  | −0.0082(7) | −0.0012(7) | −0.0020(6) |
| C20 | 0.0128(8)  | 0.0237(9)  | 0.0328(10) | −0.0120(8) | −0.0004(7) | −0.0064(6) |
| C21 | 0.0323(10) | 0.0259(10) | 0.0338(11) | −0.0078(8) | −0.0072(8) | −0.0145(8) |
| C22 | 0.0292(9)  | 0.0207(9)  | 0.0250(9)  | −0.0024(7) | 0.0002(8)  | −0.0064(7) |

The anisotropic atomic displacement factor exponent takes the form: $-2\pi^2 [h^2 a^{*2} U_{11} + \ldots + 2 hka^*b^* U_{12}]$

TABLE 20

Hydrogen atom coordinates and isotropic atomic displacement parameters, (Å²).

|      | x/a      | y/b     | z/c     | U        |
|------|----------|---------|---------|----------|
| H3A  | −0.088(4)| 0.089(3)| 0.406(2)| 0.035(7) |
| H2B  | 0.0318   | 0.4181  | −0.1643 | 0.027    |
| H3B  | −0.2067  | 0.2905  | −0.0540 | 0.027    |
| H8A  | 0.3503   | 0.4063  | 0.0672  | 0.025    |
| H10A | 0.1021   | 0.3964  | 0.4301  | 0.021    |
| H10B | 0.0367   | 0.3739  | 0.3343  | 0.021    |
| H11A | 0.3308   | 0.4616  | 0.2458  | 0.021    |
| H11B | 0.2196   | 0.5607  | 0.2872  | 0.021    |
| H12A | 0.6918   | 0.3552  | 0.4256  | 0.022    |
| H12B | 0.6176   | 0.3375  | 0.3294  | 0.022    |
| H13A | 0.5112   | 0.1665  | 0.4697  | 0.021    |
| H13B | 0.4085   | 0.2593  | 0.5199  | 0.021    |
| H15A | 0.7829   | 0.5280  | 0.4312  | 0.021    |
| H17A | 0.9087   | 0.8660  | 0.2132  | 0.023    |
| H19A | 0.4304   | 0.6760  | 0.1950  | 0.023    |
| H20A | −0.5741  | 0.0030  | 0.3255  | 0.034    |
| H20B | −0.4508  | 0.0043  | 0.2273  | 0.034    |
| H20C | −0.5676  | 0.1294  | 0.2284  | 0.034    |
| H21A | 1.2215   | 0.8068  | 0.4078  | 0.046    |
| H21B | 1.0297   | 0.8843  | 0.3535  | 0.046    |
| H21C | 1.1941   | 0.8307  | 0.2936  | 0.046    |
| H22A | 0.7058   | 1.0031  | −0.0244 | 0.040    |
| H22B | 0.8780   | 0.9086  | 0.0356  | 0.040    |
| H22C | 0.7827   | 1.0146  | 0.0736  | 0.040    |

TABLE 21

Selected hydrogen bond information (Å and °).

| D-H . . . A    | d(D-H)  | d(H . . . A) | d(D . . . A) | <(DHA) |
|----------------|---------|--------------|--------------|--------|
| N3—H3A . . . O1#1 | 0.89(3) | 2.02(3)      | 2.8652(19)   | 160(3) |

1 −x, −y, −z + 1

Example 20: Analysis XRPD Data

Figure 36:
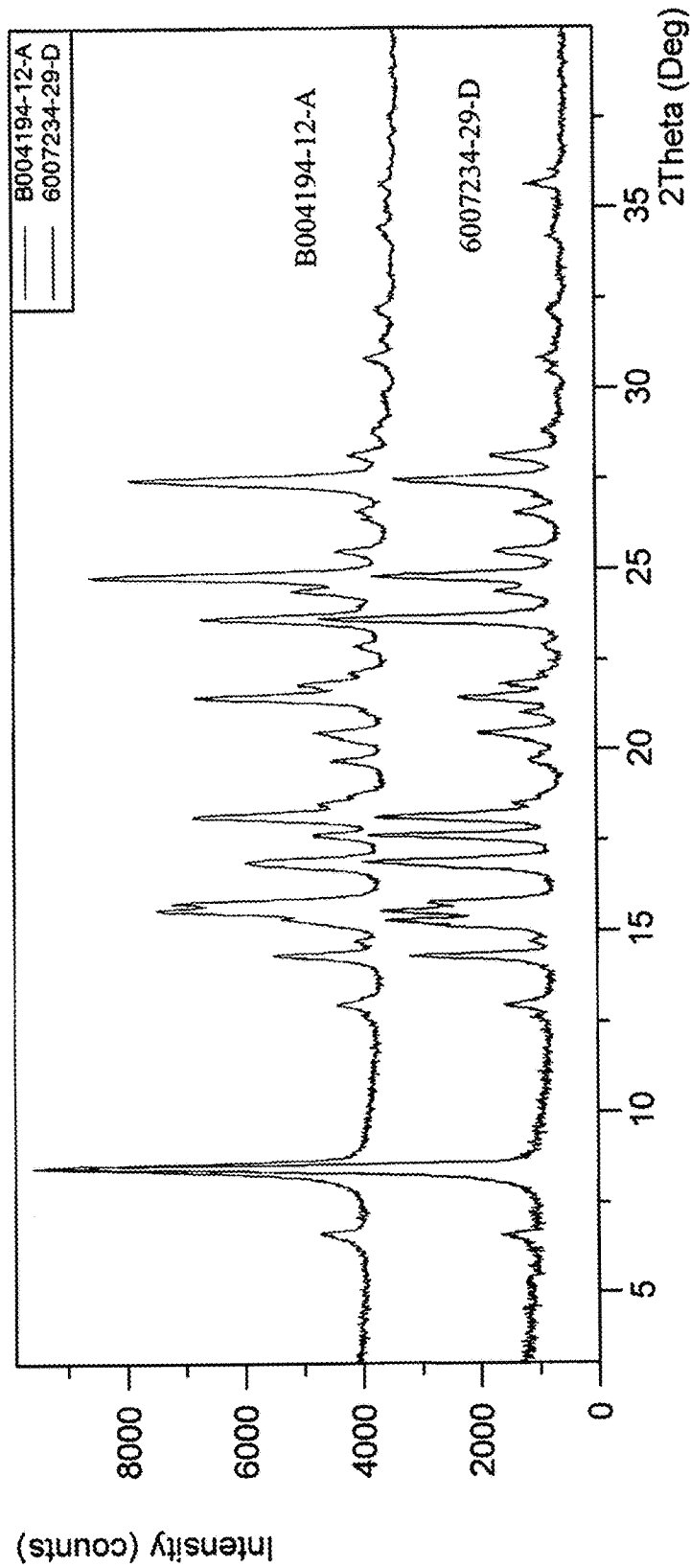
FIG. 36 shows an XRPD pattern overlay of RX-5902 nanoformulation and RX-5902 API.

An overlay comparing the XRPD patterns of RX-5902 nanoformulation (Example 18A (top)) and RX-5902 API (Example 18B (bottom)) is in FIG. 36. Although these samples were analyzed at different times, the same test method was used, which facilitates identification and comparison of peak positions. Review of the sample peak lists shows a good match on almost all of the observed peaks. Variations in peak intensity and peak splitting here are considered less significant and do not affect the match. Note also that Poloxamer 407 reflections may contribute to the nanosuspension pattern. Both patterns are consistent with crystalline material; there is no obvious amorphous component. This data demonstrates that the nanosuspension crystalline structure is consistent with RX-5902 API.

It will be apparent to those skilled in the art that specific embodiments of the disclosed subject matter may be directed to one or more of the above- and below-indicated embodiments in any combination. While the invention has been disclosed in some detail by way of illustration and example, it is apparent to those skilled in the art that changes may be made and equivalents may be substituted without departing from the true spirit and scope of the invention. Therefore, the description and examples should not be construed as limiting the scope of the invention. All references, publications, patents, and patent applications disclosed herein are hereby incorporated by reference in their entirety as if each had been individually incorporated.

What is claimed is:

1. A method of treating a tumor, comprising administering to a human subject in need thereof a solid, oral dosage form comprising a compound of formula (I)

(I)

[chemical structure]

or pharmaceutically acceptable salt thereof,
wherein the solid, oral dosage form provides an AUC$_{0-t}$ (0-24 hours) of about 800-15,000 hr·ng/mL after a single administration, wherein the solid, oral dosage form is administered at a dosage of about 100-500 mg/day, 1-7 days per week, up to about 2,800 mg/week, and wherein the tumor is selected from colorectal, ovarian, lung, breast, pancreatic, and renal cancer.

2. The method of claim 1, wherein the solid, oral dosage form is administered at a dosage of about 150-400 mg/day, 3-7 days per week.

3. The method of claim 1, wherein the solid, oral dosage form is administered at a dosage of about 150-400 mg/day, 5-7 days per week.

4. The method of claim 1, wherein the solid, oral dosage form is a tablet or capsule.

5. The method of claim 1, wherein the solid, oral dosage form provides an $AUC_{0-t}$ (0-24 hours) of about 2,500-9,500 hr·ng/mL after a single administration.

6. The method of claim 1, wherein the solid, oral dosage form provides a $C_{max}$ of about 200-1,200 ng/mL after a single administration.

7. The method of claim 1, wherein the tumor is triple-negative (TN) breast cancer.

8. The method of claim 1, wherein the tumor is platinum-resistant or -refractory ovarian cancer.

9. The method of claim 1, further comprising administering radiation or an anti-tumor agent to the subject.

10. The method of claim 1, further comprising administering to the subject an anti-tumor agent selected from antimetabolites, DNA-fragmenting agents, DNA-crosslinking agents, intercalating agents, protein synthesis inhibitors, topoisomerase I poisons, topoisomerase II poisons, microtubule-directed agents, kinase inhibitors, polyphenols, hormones, hormone antagonists, death receptor agonists, immune checkpoint inhibitors, anti-programmed cell death 1 (PD-1) receptor antibodies and anti-programmed cell death ligand 1 (PD-L1) antibodies.

11. The method of claim 1, further comprising administering to the subject a PD-L1 antibody or PD-1 antibody.

12. A method of treating a tumor in a human subject in need thereof, comprising: (a) determining whether the subject is undergoing treatment with a CYP3A4 or CYP3A5 inhibitor or inducer; and (b) if the subject is not undergoing treatment with a CYP3A4 or CYP3A5 inhibitor or inducer, then administering to the subject a solid, oral dosage form comprising a compound of formula (I)

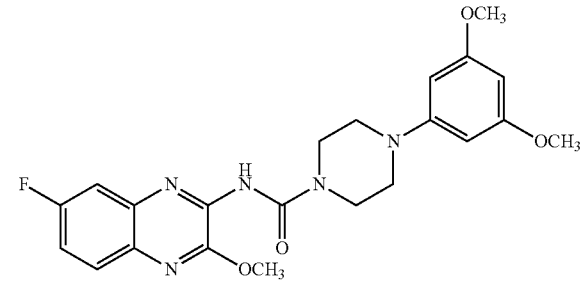

or pharmaceutically acceptable salt thereof, wherein the solid, oral dosage form provides an $AUC_{0-t}$ (0-24 hours) of about 800-15,000 hr·ng/mL after a single administration, wherein the solid, oral dosage form is administered at a dosage of about 100-500 mg/day, 1-7 days per week, up to about 2,800 mg/week, and wherein the tumor is selected from colorectal, ovarian, lung, breast, pancreatic, and renal cancer.

13. The method of claim 1, wherein the solid, oral dosage form is administered to the subject in a fed state.

* * * * *